(12) United States Patent
Makower et al.

(10) Patent No.: US 12,364,794 B2
(45) Date of Patent: Jul. 22, 2025

(54) BREAST PUMP SYSTEM WITH CONTROLLER

(71) Applicant: Willow Innovations, Inc., Mountain View, CA (US)

(72) Inventors: Joshua Makower, Los Altos Hills, CA (US); John Y. Chang, Los Altos, CA (US); Brendan M. Donohoe, Fairfax, CA (US); Sharon Lam Wang, Los Altos Hills, CA (US); Michele Torosis, Los Altos, CA (US); Earl Bright, II, Sunnyvale, CA (US)

(73) Assignee: Willow Innovations, Inc., Mountain View, CA (US)

( * ) Notice: Subject to any disclaimer, the term of this patent is extended or adjusted under 35 U.S.C. 154(b) by 5 days.

(21) Appl. No.: 18/082,620

(22) Filed: Dec. 16, 2022

(65) Prior Publication Data

US 2023/0117214 A1    Apr. 20, 2023

Related U.S. Application Data

(63) Continuation of application No. 16/934,380, filed on Jul. 21, 2020, which is a continuation of application
(Continued)

(51) Int. Cl.
*A61M 1/06* (2006.01)
*A61M 39/24* (2006.01)
(Continued)

(52) U.S. Cl.
CPC .............. *A61M 1/06* (2013.01); *A61M 1/062* (2014.02); *A61M 1/064* (2014.02); *A61M 1/066* (2014.02);
(Continued)

(58) Field of Classification Search
CPC ........ A61M 1/06; A61M 1/062; A61M 1/064; A61M 1/066; A61M 1/068; A61M 1/007;
(Continued)

(56) References Cited

U.S. PATENT DOCUMENTS

| 1,197,011 A | 9/1916 | Cilino |
| 4,263,912 A * | 4/1981 | Adams ................ A61M 1/0697 604/75 |

(Continued)

FOREIGN PATENT DOCUMENTS

| CN | 2628060 Y | 7/2004 |
| CN | 201692384 | 1/2011 |

(Continued)

OTHER PUBLICATIONS

Chiu et a., Development of a piezoelectric polyvinylldene fluoride (PVDF) polymerbased sensor patch for simultaneous heartbeat and respiration monitoring, Sensors and Actuators A: Physical, vol. 189, Jan. 15, 2013, pp. 328-334.
(Continued)

*Primary Examiner* — Kevin C Sirmons
*Assistant Examiner* — William R Frehe

(57) ABSTRACT

Systems and methods for pumping milk from a breast, wherein the milk is expressed from the breast under suction and the milk is expulsed from a pumping mechanism to a collection container under positive pressure. In one approach, a breast pump assembly includes a breast adapter and a receptacle configured to cup the breast adapter, and the breast adapter is removable from the receptacle.

15 Claims, 51 Drawing Sheets

Related U.S. Application Data

No. 16/667,749, filed on Oct. 29, 2019, now Pat. No. 10,722,624, which is a continuation of application No. 15/180,345, filed on Jun. 13, 2016, now Pat. No. 10,688,229, which is a continuation of application No. PCT/US2015/041257, filed on Jul. 21, 2015.

(60) Provisional application No. 62/027,685, filed on Jul. 22, 2014.

(51) Int. Cl.
*A61J 13/00* (2006.01)
*A61M 60/284* (2021.01)

(52) U.S. Cl.
CPC ........ *A61M 1/067* (2021.05); *A61M 1/06935* (2021.05); *A61M 1/0697* (2021.05); *A61M 39/24* (2013.01); *A61J 13/00* (2013.01); *A61M 60/284* (2021.01); *A61M 2205/15* (2013.01); *A61M 2205/3331* (2013.01); *A61M 2205/3334* (2013.01); *A61M 2205/3337* (2013.01); *A61M 2205/3344* (2013.01); *A61M 2205/3379* (2013.01); *A61M 2205/50* (2013.01); *A61M 2205/581* (2013.01); *A61M 2205/583* (2013.01)

(58) Field of Classification Search
CPC .. A61M 2210/1007; A61B 2018/00333; A61J 13/00
See application file for complete search history.

(56) References Cited

U.S. PATENT DOCUMENTS

| | | |
|---|---|---|
| 4,311,141 A | 1/1982 | Diamond |
| 4,768,547 A | 9/1988 | Danby |
| 4,821,580 A | 4/1989 | Jomitsma |
| 5,542,921 A | 8/1996 | Meyers et al. |
| 5,634,468 A | 6/1997 | Platt et al. |
| 5,658,133 A | 8/1997 | Anderson et al. |
| 5,810,772 A | 9/1998 | Niederberger |
| 5,827,191 A | 10/1998 | Rosenfeld |
| 6,273,868 B1 | 8/2001 | Nordvik |
| 6,287,252 B1 | 9/2001 | Lugo |
| 6,328,082 B1 | 12/2001 | Lafond |
| D459,233 S | 6/2002 | Young |
| 6,440,100 B1 | 8/2002 | Prentiss |
| 6,547,756 B1 * | 4/2003 | Greter ............... A61M 1/06935 604/74 |
| 6,579,258 B1 | 6/2003 | Atkin et al. |
| 6,712,785 B2 | 3/2004 | Morton et al. |
| 6,840,918 B1 | 1/2005 | Britto et al. |
| 7,201,735 B2 | 4/2007 | Atkin et al. |
| 7,223,255 B2 | 5/2007 | Myers et al. |
| 7,621,797 B1 | 11/2009 | Hershkovich |
| 7,824,363 B2 | 11/2010 | Myers |
| 7,972,297 B2 | 7/2011 | Bryan et al. |
| 7,988,661 B2 | 8/2011 | Silver et al. |
| 8,057,425 B1 | 11/2011 | Myers et al. |
| 8,070,715 B2 | 12/2011 | Quackenbush et al. |
| 8,070,716 B2 | 12/2011 | Sutrina et al. |
| 8,262,606 B2 | 9/2012 | Greter et al. |
| 8,282,596 B2 | 10/2012 | Greter et al. |
| 8,353,865 B2 | 1/2013 | Thilwind et al. |
| 8,357,116 B2 | 1/2013 | Simdon |
| 8,376,986 B2 | 2/2013 | Van Schijndel et al. |
| 8,579,874 B1 * | 11/2013 | Barack ............... A61M 1/06 604/74 |
| 8,671,701 B2 | 3/2014 | McKendry |
| 8,684,961 B2 | 4/2014 | Gottenbos et al. |
| 8,801,495 B1 | 8/2014 | Guindon |
| 9,050,404 B2 | 6/2015 | Silver et al. |
| 9,162,016 B2 | 10/2015 | Geddes |
| 9,173,587 B2 | 11/2015 | Van Schijndel et al. |
| 9,199,017 B2 | 12/2015 | Greter |
| 9,278,167 B2 | 3/2016 | Aalders et al. |
| 10,722,624 B2 * | 7/2020 | Makower ............... A61M 1/064 |
| 2003/0191433 A1 | 10/2003 | Prentiss |
| 2004/0024351 A1 | 2/2004 | Greter et al. |
| 2004/0101414 A1 | 5/2004 | Gharib et al. |
| 2004/0127845 A1 | 7/2004 | Renz et al. |
| 2005/0059928 A1 | 3/2005 | Larsson |
| 2005/0131332 A1 | 6/2005 | Kelly et al. |
| 2005/0234370 A1 | 10/2005 | Beal et al. |
| 2005/0245860 A1 * | 11/2005 | Britto ............... A61M 1/066 604/74 |
| 2006/0106334 A1 | 5/2006 | Jordan et al. |
| 2008/0045887 A1 * | 2/2008 | Larsson ............... A61M 1/0697 604/74 |
| 2008/0045888 A1 | 2/2008 | Edwards et al. |
| 2008/0177224 A1 | 7/2008 | Kelly et al. |
| 2008/0243059 A1 | 10/2008 | Yamashita et al. |
| 2009/0024080 A1 | 1/2009 | Rohrig |
| 2010/0106082 A1 | 4/2010 | Zhou |
| 2010/0217148 A1 | 8/2010 | Binder |
| 2010/0324478 A1 * | 12/2010 | Kazazoglu ............... A61M 1/06 604/74 |
| 2011/0004154 A1 * | 1/2011 | Van Schijndel ....... A61M 1/732 604/74 |
| 2011/0071466 A1 | 3/2011 | Silver et al. |
| 2011/0196291 A1 | 8/2011 | Vischer et al. |
| 2011/0245763 A1 | 10/2011 | Myers |
| 2011/0270162 A1 | 11/2011 | Guo |
| 2012/0101575 A1 | 4/2012 | Horne et al. |
| 2012/0277636 A1 | 11/2012 | Blondheim et al. |
| 2012/0277728 A1 * | 11/2012 | Weber .................. A61M 1/064 604/74 |
| 2013/0023821 A1 * | 1/2013 | Khalil .................. A61M 1/064 604/74 |
| 2013/0123688 A1 | 5/2013 | Bosman et al. |
| 2013/0131588 A1 | 5/2013 | Silver et al. |
| 2013/0177455 A1 | 7/2013 | Kamen et al. |
| 2014/0066734 A1 | 3/2014 | Zdeblick |
| 2014/0135683 A1 * | 5/2014 | Hradisky ................. A61M 1/06 604/74 |
| 2014/0142501 A1 * | 5/2014 | Clark .................... A61M 1/062 604/74 |
| 2014/0263611 A1 * | 9/2014 | Bauer .................... A61M 1/062 604/74 |
| 2014/0378895 A1 | 12/2014 | Barack |
| 2014/0378946 A1 | 12/2014 | Thompson et al. |
| 2015/0065994 A1 | 3/2015 | Fridman et al. |
| 2015/0100016 A1 | 4/2015 | Liao |
| 2015/0148709 A1 | 5/2015 | Mardiks et al. |
| 2015/0196247 A1 | 7/2015 | Lau |
| 2015/0292500 A1 | 10/2015 | Girard et al. |
| 2016/0015876 A1 | 1/2016 | Tattersfield et al. |
| 2016/0256618 A1 | 9/2016 | Embleton |

FOREIGN PATENT DOCUMENTS

| | | |
|---|---|---|
| EP | 2456482 B1 | 11/2016 |
| EP | 3151876 B1 | 11/2017 |
| GB | 2342446 A | 4/2000 |
| JP | 2005279044 | 10/2005 |
| RU | 2012 107356 | 5/2012 |
| WO | WO1996022116 | 7/1996 |
| WO | WO 2000/57934 | 10/2000 |
| WO | WO2001054488 | 8/2001 |
| WO | WO2011010255 | 1/2011 |
| WO | WO2011144984 A | 11/2011 |
| WO | WO2012037848 | 3/2012 |
| WO | WO2012037848 A1 | 3/2012 |
| WO | WO 2013076055 | 5/2013 |
| WO | WO2013088310 | 6/2013 |
| WO | WO 2013/187763 | 12/2013 |

(56) References Cited

FOREIGN PATENT DOCUMENTS

| WO | WO2013184004 | 12/2013 |
|----|--------------|---------|
| WO | WO2015120321 | 8/2015  |

OTHER PUBLICATIONS

Double Electric Breast Pump/Dr. Brown's, http://www.drbrownsbaby.com/breastfeeding-product/breast-pumps/double-electric, May 15, 2014.

* cited by examiner

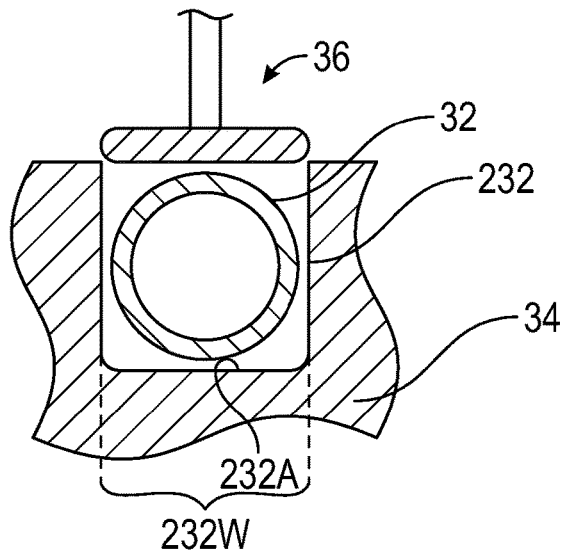
FIG. 17C
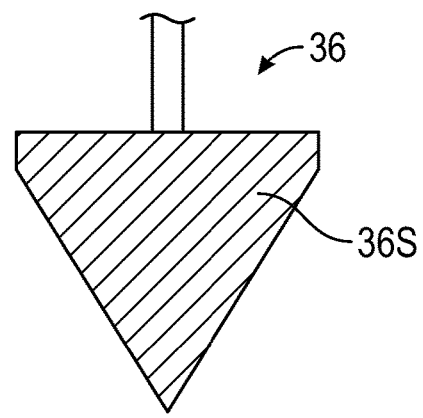
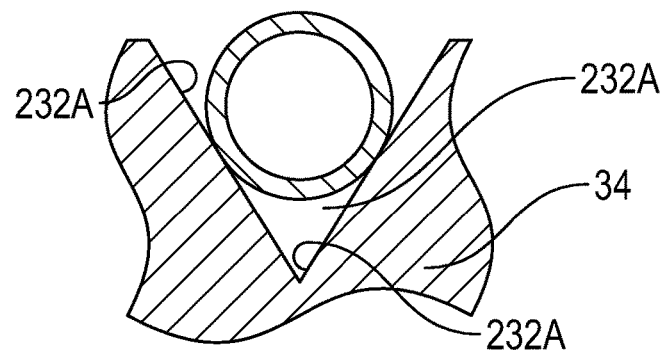
FIG. 17D
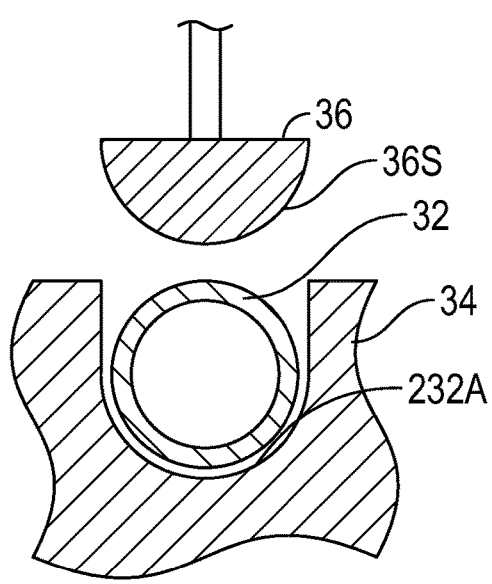
FIG. 17E

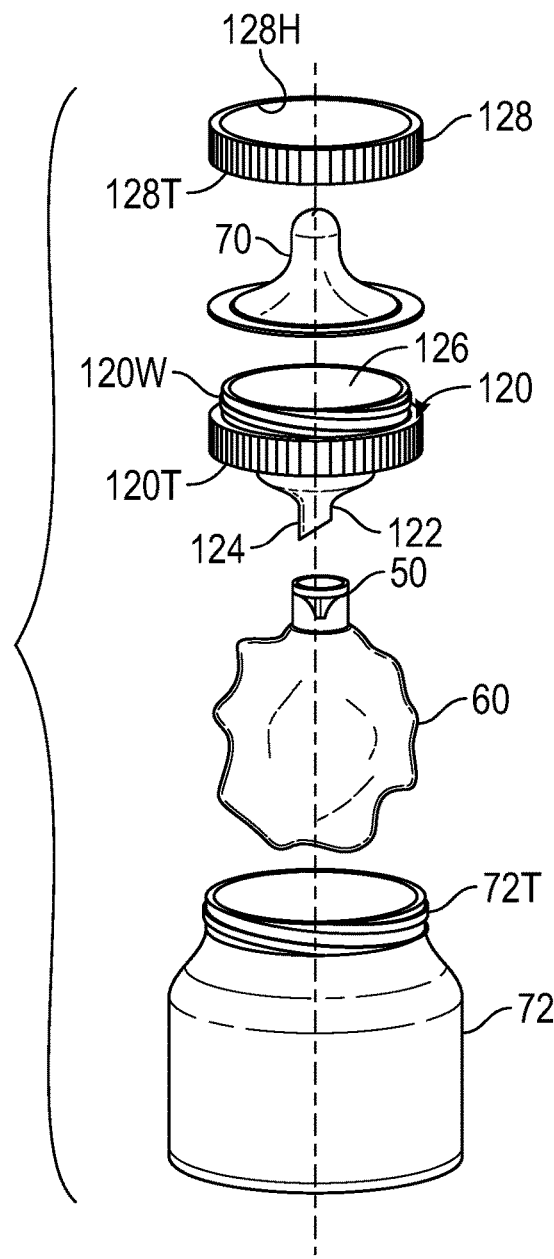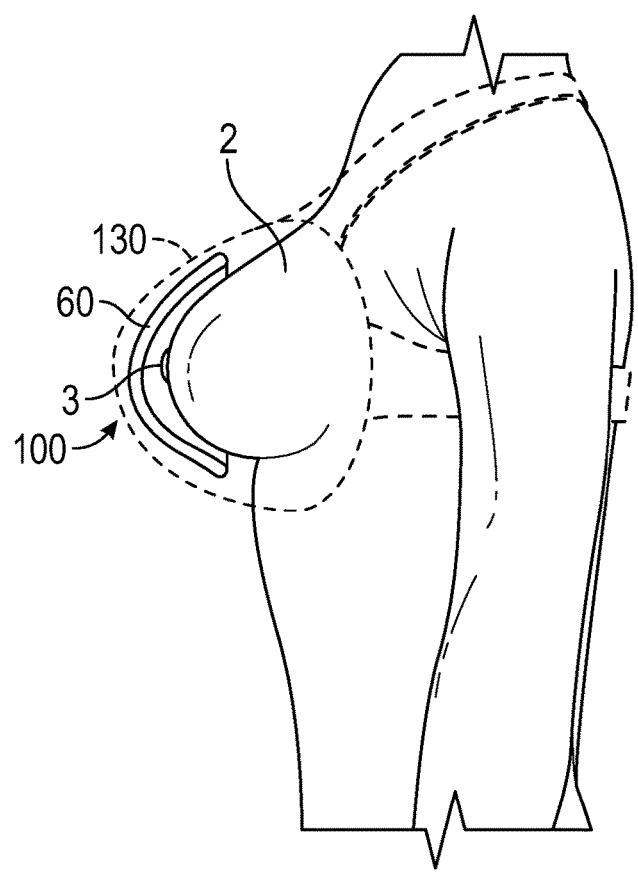
FIG. 23
FIG. 24

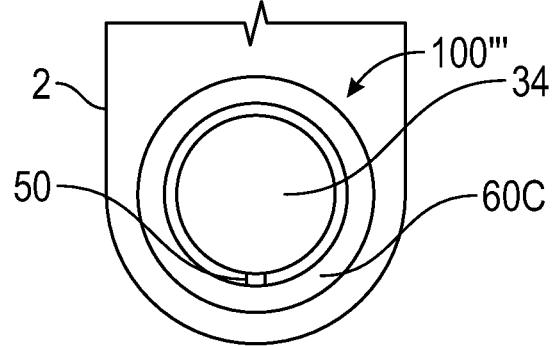
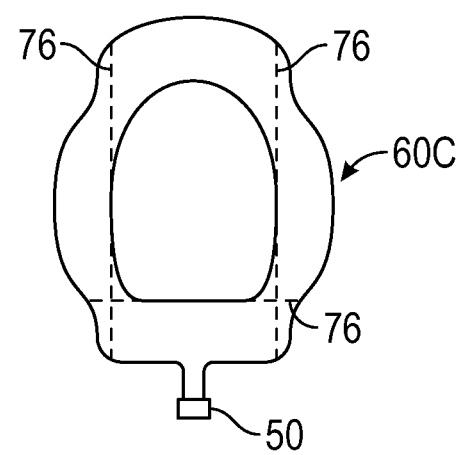
FIG. 29A          FIG. 29B
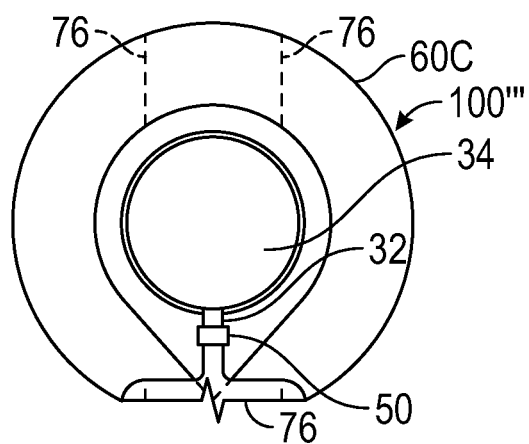
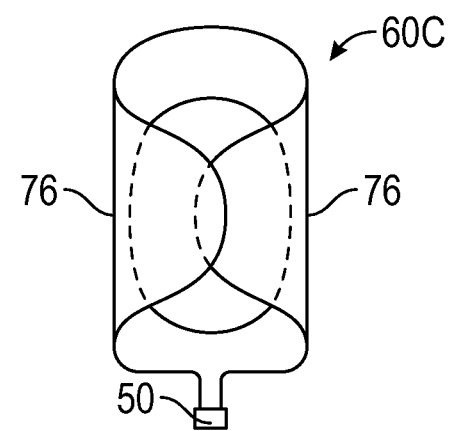
FIG. 29C          FIG. 29D

BREAST PUMP SYSTEM WITH CONTROLLER

FIELD OF THE DISCLOSURE

The present disclosure generally relates to a portable, hands-free, discrete, self-powered and energy efficient breast pump system and method for collecting milk from a breast of a nursing mother.

BACKGROUND OF THE DISCLOSURE

As more women become aware that breastfeeding is the best source of nutrition for a baby, and also offers health benefits to the nursing mother, the need is increasing for breast pump solutions that are user-friendly, quiet, discrete and versatile for use by a nursing mother in various situations. This is particularly true for the working mother, who is away from the home for eight to ten hours or more and needs to pump breast milk in order to have it available for her baby, but it is also a requirement for many other situations where the mother is away from the privacy of the home for an extended period, such as during shopping, going out to dinner or other activities.

Although a variety of breast pumps are available, most are awkward and cumbersome, requiring many parts and assemblies and being difficult to transport. Hand pump varieties that are manually driven are onerous to use and can be painful to use. Some powered breast pumps require an AC power source to plug into during use. Some systems are battery driven, but draw down the battery power fairly rapidly as the motorized pump continuously operates to maintain suction during the milk extraction process. Many of the breast pumps available are clearly visible to an observer when the mother is using it, and many also expose the breast of the mother during use.

There is a continuing need for a small, portable, self-powered, energy efficient, wearable breast pump system that is easy to use and is discrete by not exposing the breast of the user and being invisible or nearly unnoticeable when worn.

SUMMARY OF THE DISCLOSURE

Briefly and in general terms, the present disclosure is directed towards breast pump systems and methods. The system includes breast contacting structure, a collection container and structure that extracts milk from a breast and delivers the milk to the container. The method involves extracting milk from a breast and delivering the milk to the collection container.

In one approach, a method of pumping milk from a breast involves forming a seal between a breast pump system and the breast, and pumping milk expressed from the breast through a conduit. A driving force may also be included and created by expansion of the conduit that was previously compressed to generate suction that drives expression of milk from a breast. The driving force may also be generated by pulling on the conduit that was previously compressed. Expulsion of expressed milk can be achieved by the application of a relative positive pressure to a portion of the conduit. In one particular aspect, suction applied to the breast for expression of milk involves a first suction level, and during expulsing, a second suction level is maintained against the breast, the second suction level being lower than the first suction level.

In various of the disclosed embodiments, the system defines a natural breast profile. The natural breast profile is contemplated to fit comfortably and conveniently into a bra of a user and to present a natural look. As such, the profile is characterized by having a non-circular base. Moreover, like natural breasts, the profile of the device or system is contemplated to define one or more asymmetric curves and off-center inertial centers.

The disclosed method can alternatively or additionally involve one or more of providing a substantially liquid tight path between a breast through a conduit, compressing a portion of the conduit and reducing compression where returning the conduit to an uncompressed state generates suction sufficient to extract milk from a breast. Pumping can also involve compressing a second portion of conduit to generate pressure. A one-way valve between the conduit and a storage can be provided to prevent backflow of milk and air.

A pump device can be placed in contact with a breast and connected to a storage container. Each of the pump device and storage container can be sized and shaped to be received within a user's bra. In one approach, the storage container is positioned between the pumping structure of the device and a user's bra. In other approaches, the storage container is configured about pumping structure, or can be positioned between pumping structure and the user's breast. Pumping of milk from a breast can occur without creating a change in a total mass and volume of the breast, pump device and storage container. The storage container can be one or more of flexible, or positioned around the breast. A driving mechanism can also be defined by a roller configured to maintain fluid connection between proximal and distal portions of conduit. The driving mechanism can alternatively include a single compression driver and first and second one-way valves in the conduit on opposite sides of a region that the compression driver is configured to compress. The system can include first and second drivers, where the first driver compresses a first region of conduit and the second driver compresses a second region of conduit. The first and second drivers can be configured to intermittently compress and release compression of regions of the conduit. The driving mechanism may also have its movements coordinated to create pressures sufficient to drive extracted milk. A first driver can be configured to seal a region of the conduit when milk is pumped, and sufficient pressure can be created in certain embodiments to pump milk against gravity.

A controller can be included in certain of the disclosed embodiments. The controller can be one or more of electrically connected to the pump, or configured to supply power for movements of driving mechanisms, and a battery electrically connected thereto. A pressure sensor can be further included to sense pressure within a breast adapter and in certain embodiments, the pressure sensor can be in electronic communication with the controller. Moreover, in certain approaches, the controller can adaptively control movements of drivers with input from a feedback loop established with a pressure or other sensor. The controller can further be programmable to changed control settings.

The system can be configured to generate a suction force in the range of about −60 mm Hg, or in a range of about −120 mm Hg to about −450 mm Hg, or in a range of about −60 mm Hg to about −180 mm Hg, or in a range of about −60 mm Hg to about −220 mm Hg, or in a range of about −200 mm Hg to about −450 mm Hg, or in a range of about −380 mm Hg to about −420 mm Hg, or in a range of about −180 mm Hg to about −400 mm Hg, or in a range of about −180 mm Hg to about −220 mm Hg, or in the range of about −40 mm Hg to about −70 mm Hg, or in the range of about −50 mm Hg to about −60 mm Hg.

A breast adapter or pump system generally can include at least one vibration element configured to apply vibration to the breast, and/or at least one heating element to apply heat to the breast. The breast adapter and conduit can be integrally formed as a unit or can define separate pieces. The breast adapter and conduit can further be configured to be removable from the pump system and replaceable. A housing can be further provided and can contain the driving mechanism and controller. The housing also can include manually operated controls for input to the controller, and additionally or alternatively, a display that is readable by the user.

In one or more embodiments, the storage container is detachable from the system. There can be a plurality of drivers having different shapes and sizes or lengths. A lower surface of a driver can be V-shaped in cross-section. A driver can be attached to a breast adapter and configured to expand the breast adapter. The breast adapter can further comprise a first flange and a second flange, wherein a gap is formed between the flanges that prevents milk spillage. In another aspect, insertion of the breast into the adapter and against the second flange deflects the second flange toward the first flange. Also, in certain embodiments, suction collapses the gap between first and second flanges.

In certain approaches, milk extraction is halted while milk is pumped to the storage container. Moreover, suction can be cycled to stimulate milk letdown and initiate extraction during letdown. After a predetermined time or after calculating an estimate of a predetermined volume of milk having been extracted, the breast can be sealed off at a predetermined suction level. The system can be configured such that a pumping mechanism is positioned less than 2.5 cm from a nipple of a breast, or less than 2.0 cm from the nipple or less than or equal to 1.0 cm from the nipple. Pumping can further or alternatively be accomplished without any mechanical motion of the breast or nipple. Also, pumping can be carried out by a pumping mechanism that is external to the conduit and not in fluid communication with the conduit.

Certain approaches or embodiments of the system or method can involve outputting at least one of operational and/or sensed parameters, and modifying at least one operational setting based upon the operational or sensed parameters. The system or method can further perform in real-time, or as a feedback loop. An operational setting can be one or more of suction level setting, suction waveform definition, extraction phase time, threshold milk volume estimate per extraction phase expulsion, pressure, rest phase time, heating temperatures, heating times, vibration frequency and vibration times. The system can also be configured to upload operational or sensed parameters from an external computer to a cloud server.

Suction can be maintained at a minimum during an entire milk pumping session or suction can be intermittent where suction is reduced to zero at least once over the duration of a milk pumping session. Further, the suction level can be monitored and a determination can be made when at least a minimum suction level has not been maintained and the system can be shut down. Indicators can be provided to indicate ceasing of pumping and/or to indicate when the device is to be removed from the breast. A non-contact pressure sensor is also contemplated to be incorporated into one or more of the disclosed embodiments or methods. In one approach, the sensor can define a magnetic proximity sensor.

These and other features of the disclosure will become apparent to those persons skilled in the art upon reading the details of the specification as more fully described below.

BRIEF DESCRIPTION OF THE DRAWINGS

FIG. 17C is a cross-sectional illustration of a compression element and tube being received in a channel formed with a substantially planar or flat anvil surface, according to an embodiment of the present disclosure.

FIG. 17D shows a cross-sectional view of a compression element and tube being receive in a channel, wherein the anvil surface of the channel is substantially V-shaped in cross-section and the compression element has a compression surface that is substantially V-shaped, according to an embodiment of the present disclosure.

FIG. 17E shows a cross-sectional view of a compression element and tube being receive in a channel, wherein the anvil surface of the channel is concave in cross-section and the compression element has a compression surface that is convex, according to an embodiment of the present disclosure.

FIG. 23 is an exploded view of an alternative arrangement for installing a container in a bottle and providing it with a feeding nipple, according to another embodiment of the present disclosure.

FIG. 24 is an illustration of a system installed on a breast around the nipple and supported by a bra in which the system is received, according to an embodiment of the present disclosure.

FIG. 29A illustrates a container that fits around the main body of the system and the areola of the breast, according to an embodiment of the present disclosure.

FIG. 29B illustrates a variant of a container in which the one way valve is located on the outside of the annular container, according to an embodiment of the present disclosure.

FIG. 29C shows the one way valve and connecting portion of the container of FIG. 28B having been folded upwardly along a baffle line to join the one-way valve to the tube of system, according to an embodiment of the present disclosure.

FIG. 29D shows a container having been folded for more compact storage, according to an embodiment of the present disclosure.

DETAILED DESCRIPTION

Before the present systems and methods are described, it is to be understood that this disclosure is not limited to particular embodiments described, as such may, of course, vary. It is also to be understood that the terminology used herein is for the purpose of describing particular embodiments only, and is not intended to be limiting, since the scope of the present disclosure will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the disclosure. The upper and lower limits of these smaller ranges may independently be included or excluded in the range, and each range where either, neither or both limits are included in the smaller ranges is also encompassed within the disclosure, subject to any specifically excluded limit in the stated range. Where the stated range includes one or both of the limits, ranges excluding either or both of those included limits are also included in the disclosure.

Unless defined otherwise, all technical and scientific terms used herein have the same meaning as commonly understood by one of ordinary skill in the art to which this disclosure belongs. Although any methods and materials similar or equivalent to those described herein can be used in the practice or testing of the present disclosure, the preferred methods and materials are now described. All publications mentioned herein are incorporated herein by reference to disclose and describe the methods and/or materials in connection with which the publications are cited.

It must be noted that as used herein and in the appended claims, the singular forms "a", "an", and "the" include plural referents unless the context clearly dictates otherwise. Thus, for example, reference to "a valve" includes a plurality of such valves and reference to "the pump" includes reference to one or more pumps and equivalents thereof known to those skilled in the art, and so forth.

The publications discussed herein are provided solely for their disclosure prior to the filing date of the present application. The dates of publication provided may be different from the actual publication dates which may need to be independently confirmed.

Figure 1:
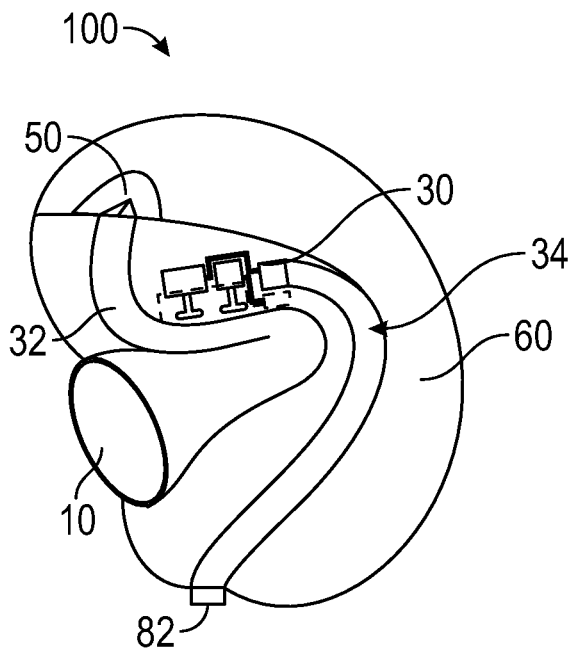
FIG. 1 is an illustration of a breast pump system according to an embodiment of the present disclosure.

FIG. 1 is an illustration of a breast pump system 100 according to an embodiment of the present disclosure. System 100 includes a breast adapter 10, a pumping region 30 within a main body 34, a one-way valve 50 and a milk storage container 60.

Figure 2:
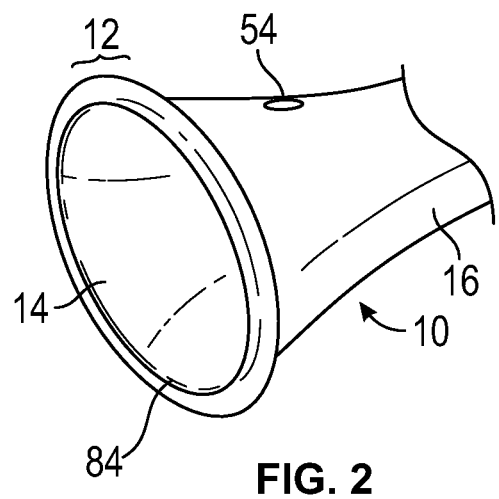
FIG. 2 is a partial view of the system of FIG. 1 showing only a portion of the breast adapter.

FIG. 2 is a partial view of the system 100 showing only a portion of the breast adapter 10. Breast adapter 10 includes a compliant region 12 made of silicone or other compliant, biocompatible material, such as, but not limited to polyurethane and/or polyether block amides (PEBAX) to provide a soft interface with the breast and also provide a seal around the areola and nipple of the breast. An inner housing 14 is configured and dimensioned to surround the nipple of the breast. Inner housing 14 can be rigid, semi-rigid or compliant. Preferably the breast adapter 10 is compliant and made from silicone or polyethylene terephthalate (PET), although other materials and combinations of materials could be used, including, but not limited to polyurethanes, polyethylene, high density polyethylene (HDPE), low density polyethylene (LDPE), polyamides, polyethylene terephthalate (PET) and/or PEBAX, For the embodiments where there is compliance, inner housing 14 is capable of iteratively opening and closing during extraction of milk from the breast using system 100, thereby simulating a feeding cycle similar to the sequence of the tongue against the nipple when a baby is suckling.

An open segment 16 within the housing of breast adapter 10 is configured and dimensioned to allow for at least some clearance and space in front of the nipple to permit milk to exit the nipple even when the nipple is pulled forward by suction. The open section 16 terminates with a U-turn to double back to form an acute angle to minimize the overall height/profile of the system 100 away from the breast.

Figure 3:
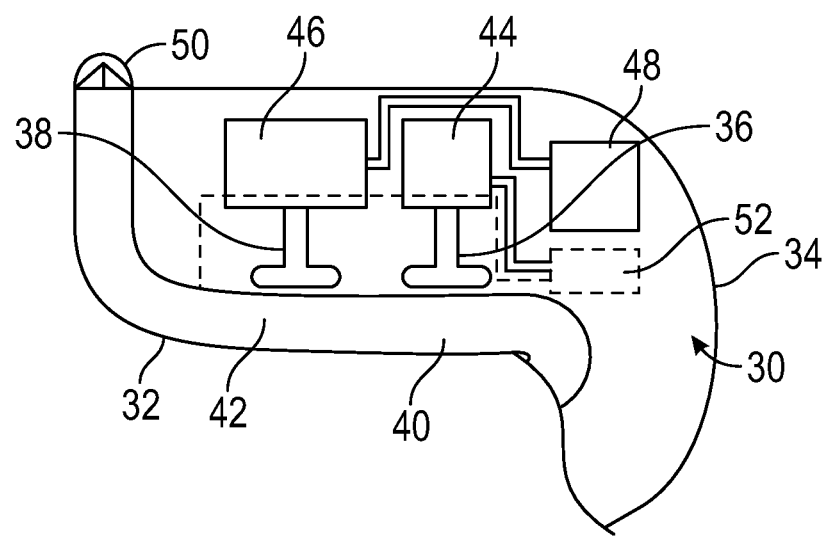
FIG. 3 is a partial, schematic illustration of the system of FIG. 1 showing the pumping region.

FIG. 3 is a partial, schematic illustration of system 100 showing the pumping region 30. A resilient tube 32 is in fluid communication with and extends proximally from the proximal end of breast adapter 10. Preferably, resilient tube 32 is integral with breast adapter 10 as shown in FIG. 1. Two active compression elements 36, 38 are operable to compress and allow decompression of the resilient tube 32 at compressible regions 40 and 42, respectively. Although the preferred embodiment uses two active compression elements as shown, alternative embodiments could have three or more active compression elements. Resilient tube 32 is preferably made of silicone, but could alternatively be made from other thermoplastic elastomers exhibiting the desired performance characteristics described herein, including, but not limited to polyurethanes and/or PEBAX. Different regions of tube 32 may be of different materials/material properties. The regions can all be molded of same material, overmolded, glued or otherwise attached, constructed, etc. In at least one embodiment, the compressible regions may have different properties from other non "active" regions—such as those non active regions being rigid (e.g., downstream of the pumping region and/or other non-active regions) to improve pumping efficiency by reducing energy losses due to expansion and contraction of regions not intended to be active. The non-active regions can be made of different materials from the active regions or otherwise reinforced. The various regions can also be other shapes than circular in cross-section. The material(s) from which the compression regions 40, 42 of tube 32 are made can be the same as that of the flange and nipple housing of breast adapter 10, only differing optionally by thickness, they could be assembled out of different materials and fused or glued together, or could be insert molded together. Further alternatively, the material(s) from which the compression regions 40, 42 are made can differ from one another. A factor in the choice of material and material thickness and length is the response time required to expand the compression regions 40, 42 from a target compressed shape/state to an original, unbiased rebound configuration (e.g., return to a full cylindrical shape in the embodiments where tube 32 is cylindrical), force required to compress to the desired target compressed shape, radial force (pressure drop) achieved when allowing the tube 32 to self-expand, volume within the inside diameter of the tube 32 regions 40 and 42, compatibility with the materials for the remainder of the breast adapter 10 (nipple housing), resiliency to maintain its material properties through multiple wash, aging and use cycles, surface and depth characteristics such as material transparency, clarity and texture/feel against the skin, visual appearance, mechanical durability, tear resistance, shape memory, soft/hardness, biocompatibility, non-reactivity and free of leachables, heat/cold resistance, etc.

Examples of tubes 32 include, but are not limited to: silicone tubing, such as used in peristaltic pumps, both platinum-cured and peroxide-cured silicone tubes. Dimensions can range greatly in inside diameter and wall thickness, but preferred embodiments can have an inside diameter of 3/16 in., 1/4 in. or 5/16 in. Walls may also range to impact properties, with preferred embodiments likely in the 1/16 in. to 1/8 in. range. Inside diameters and wall thicknesses can be varied, as needed, with ensuing appropriate lengths of tubing 32. Further alternatively, pumping regions 40, 42 do not need to be in the shape of a cylindrical tube, or even a tube at all, but can be any volume shape that can be changed/compressed. For example, the cross-section could be oval, square, trapezoid, etc. as needed to fit the device space. Examples of tube inside diameters, wall thicknesses and hardness include, but are not limited to: 0.188" ID, 0.063" wall, Durometer 50 shore A; 0.250" ID, 0.063" wall, Durometer 50 shore A; 0.313"ID, 0.063" wall, Durometer 59 shore A; and 0.313" ID, 0.094" wall, Durometer 59 shore A.

As shown, the compression elements 36, 38 comprise pistons, but alternative features could be used to accomplish the same function, such as lever arms, screw drives, clamps, cams, pincers, rollers, magnets, electro-magnets, linear drives, solenoids, gears, stepper motors, or other features, respectively. The compression surfaces of the compression elements 36, 38 may be formed as flat paddles to allow complete crushing of the tube 32 without residual volume. Alternatively, one or both compression surfaces may be formed with a "V-shaped" edge aligned axially with the tubing 32 to allow less force to compress tubing 32 to the same distance of compression, relative to a flat surface paddle. Further alternatively, or additionally, one or both compression surfaces may be formed with a cross edge (perpendicular) to axis of tubing. This provides a relatively small surface area allowing less force to completely seal tubing 32 at the location of the cross edge. However this also provides a relatively minor volume change/pressure change capability.

One or both compression surfaces may be formed as roller paddles having curved surfaces so that the compression action is not simply straight into the tubing 32. The roller paddle surface can roll on the tubing 32 to seal and move in a given direction. Dual action of the roller can be provided, so that, initially the roller comes down in compression against the tube 32 and seals the tube 32, which may be capable of being performed with relatively low force. Secondarily, the roller paddle can roll the compression surface in a predetermined direction along the length of the tube 32 and squeeze a volume of milk or air or combination in a given direction. This can be useful to maximize both increase and decrease in pressure changes and fluid movement.

Also, although the preferred embodiments described herein power the compression elements 36, 38, using electrical power supplied by one or more batteries, alternatively, they could be powered by AC electricity by plugging the system in using an AC power cord, compressed gas, spring loaded power (which may offer ways to "hand crank" to power w/o electricity), gas or suction from a remote source such as a traditional breast pump uses, etc.

Each compression element 36, 38 is operatively connected to a driver 44, 46, respectively, for independent but coordinated driving and retraction of the compression elements 36, 38. When electrically-powered drivers are used, a battery 48 is electrically connected to the drivers 44, 46 and supplies the power necessary to operate the drivers 44, 46 to drive the compression and retraction of the compression elements 36, 38. Optionally, a controller 52 may be electrically connected to the drivers 44, 46 and may be configured to modify the operation of the compression elements 36, 38 based on input received from an optional pressure sensor 54 (or multiple pressure sensors) that may be placed at least one location to assess the pumping function and maintain an acceptable pumping negative pressure profile for a wide variety of milk expression volumes. As shown, pressure sensor 54 is placed in the inner housing 14 to measure the negative pressure within the inner housing, which is the environment that the nipple is in. Alternatively or additionally, one or more pressure sensors could be placed in tube 32 upstream of compression driver 36, in between the locations of compression drivers 36 and 38 and/or downstream of compression driver 38. Further alternatively or additionally, a pressure sensor could be placed in tube 32 near, but upstream of one-way valve 50. The pressure sensor 54 (and/or flow sensor or any other sensor employed)—may be inserted into the tube 32, but is preferably designed in such a fashion such that it produces a signal that correlates to a pressure (or flow) but may not necessarily itself be in contact with the fluid and/or gas generating the pressure or flow. This arrangement that does not directly contact the milk (interior of the tube 32) is preferred to simplify cleaning of the tube 32/breast adapter 10 or to make it cost feasible to provide the breast adapter 10/32 as a disposable unit.

Sensor 54 is preferred to be a pressure sensor but could also be a flow, temperature, proximity, motion sensor or other sensor capable of providing information usable to monitor the safety or function of the pump mechanism of system 100. Preferably sensor 54 is located nearby where the tip of the nipple 3 is located to determine actual pressure being exposed to the breast 2/nipple 3, but other sensors 54 may be located within the system 100, for example, near where the one-way valve 50 is located, and can be used to monitor other features such as bag or expulsion pressure or flow rate. With at least one sensor 54 present, by monitoring either flow or pressure directly or indirectly and also taking into account the cycles and actual positions of the compression elements 36, 38 over time, it is possible to derive/calculate approximately the volume of milk produced during a pumping session as well as understand the flow-rate at any particular time in a pumping session. The accuracy of this measurement is greatest when there is no leak of air around the breast 2 and also when there is negligible air within the tube 32, after elimination by a few cycles of the pumping mechanism.

In one system set-up, an ideal minimum suction value of a cycle is preset and a maximum suction value of a cycle is preset. Maximum suction is achieved by the opening of one or more of the compression regions 40, 42. The greater the opening/release (assuming the tubing 32 has capacity), the greater the suction. A maximum suction for the system is achieved when both compression regions are completely released from the tubing 32, but preferably the system 100 is designed such that the operating region would not include that state to allow for flexibility in suction capacity. The minimum suction is the target minimum suction at the breast 2 at each suction cycle. When this suction is achieved, the most proximal compression region 40 to the breast 2 is closed/sealed and the milk expressed during the previous cycle is expulsed by the second compression element 38 from the second region 42 through the one-way valve 50 into the storage container 60. The timing of the proximal compression is set by a combination of milk expression rate within a specified maximum suction achieved by the tube 32 and the relaxation rate and state of the expansion of the tube 32. Thus milk expression sets the pace for the pump cycle at a targeted minimum suction, whereas the degree of compression at the various compression regions are set by maximum desired suction pressure and duration as well as milk volume capacity within the system. Thus, in at least one embodiment, a user can optimally set maximum peak pump pressure and maximum valley pump pressure and the remainder of parameters within the system would automatically adjust themselves based on milk expression rate and other fixed parameters within the system.

Controller 52 can also be pre-programmed for control of an operating sequence for driving and retracting the compression members. Preferably, controller 52 is configured to drive and retract the compression members 36, 38 via an active feedback loop, to adjust the positions of the compression members 36, 38 as needed to establish the desired negative pressure (i.e., suction) profile for optimizing milk extractions. If a controller 52 is not used, the drivers 44, 46 can be synchronized to run so that the compression drivers 36, 38 are operated in a desired coordinated manner. For example, one or more pumps can be operated in a predetermined manner without using pressure feedback. Alternatively, a different form of feedback may be employed, such as mentioned above. Even without any feedback, one or more compression elements may be operated in a predetermined sequence to create vacuums. There may be pressure relief valves so that the vacuum level the nipple experiences does not get too high into a harmful zone. Further optionally, pressure sensor 54 can be used to detect pressure changes indicative of milk volume expressed to calculate an approximation of milk volume extracted.

A one-way valve 50 such as a duckbill valve or other type of one-way valve is provided at the end of tube 32 where it enters the milk collection/storage container 60. Valve 50 prevents back flow of milk into the tube 32, as well as preventing air from entering the proximal end of the tube and thereby maintains the suction (vacuum) level in the tube 32. In an alternative embodiment, a pressure relief valve can be provided in the breast adapter 10 near the nipple 3. The pressure relief valve can be configured to release at vacuums greater than a predetermined amount, (e.g., vacuums less than −220 mm Hg). The one-way valve 50 can be configured and designed such that it allow fluid to flow through it only when the vacuum pressure is less than some threshold (e.g., pressures greater than or equal to −60 mmHg). The action of the compression elements cycles between increasing vacuum when the compression elements move in a direction away from tube 32 and decreasing when the compression elements compress the tube 32, but typically should not increase the vacuum to greater than the predetermined maximum vacuum (e.g., not less than −220 mm Hg). As the compression elements 36, 38 compress the tube 32, the pressure in the system 100 goes up and reaches the crack pressure of −60 mmHg, that opens the one-way valve 50. The compression elements 36, 38 continue compressing tube 32, pumping fluid (milk) through the one-way valve 50 and into the collection container 60 until the compression elements 36, 38 bottom out. As the compression elements 36, 38 reverse direction and pull away from the tube 32, they start the cycle again.

Figure 4A:
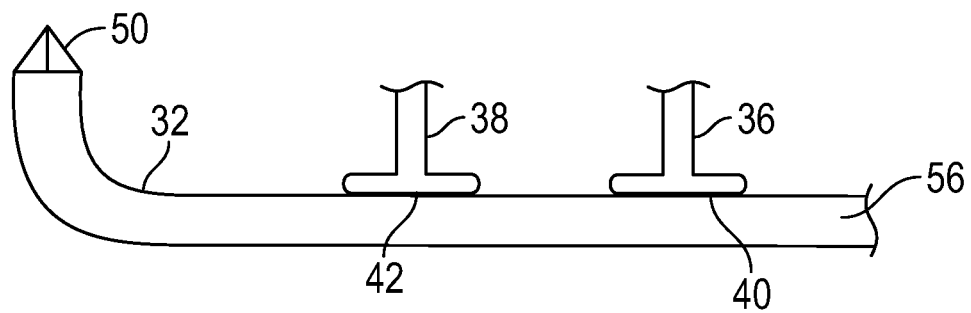
FIGS. 4A-4F illustrate the interaction between compression elements and resilient tubing, and a pumping sequence according to an embodiment of the present disclosure.

FIGS. 4A-4F illustrate the interaction between compression elements 36, 38 and resilient tubing 32 and a pumping sequence according to an embodiment of the present disclosure. The resilient tube 32 has a lumen 56 configured and dimensioned to deliver milk from the breast through the one-way valve 50 and into the milk collection/storage container 60. As illustrated, tube 32 is cylindrical and lumen 56 is circular in cross-section, but in other embodiments, the lumen 56 could be oval or other cross-sectional shape. Likewise, tube 32 could have an oval or other cross-sectional shape. The cross-sectional shapes of the lumen 56 and tube 32 are typically the same, but need not be. In one preferred embodiment, the suction (vacuum) established by the system is established solely by the resilient, "springback" action of the tubing 32. Tubing 32 is designed and configured to establish a maximum suction/vacuum in the range of less than −60 mm Hg, preferably in the range of −120 mm Hg to −450 mm Hg, more preferably in the range of −180 mm Hg to −400 mm Hg when rebounding from the closed configuration shown in FIG. 4B to a fully rebounded position as illustrated in FIG. 4A. Tubing 32 is designed so that the rebound of the regions 40, 42 creates a suction vacuum in the tube 32 sufficient to ensure that the system 100 achieves vacuum around the nipple 3, so that any losses in the system 100 are taken into account. The vacuum achieved at the breast nipple 3 should achieve a maximum suction of at least up to 300 mmHg suction (−300 mm Hg pressure). Initially upon installation of system 100 to the breast 2, it may take several cycles of the compression elements 36, 38 before the vacuum reaches its maximum vacuum. In another embodiment the achievement of maximum suction may be as high as 450 mm Hg suction (−450 mm Hg pressure).

In at least one embodiment, the maximum suction/vacuum capable of being established by tube 32 is in the range of −180 mm Hg to −220 mm Hg, preferably about −200 mm Hg. This provides a built-in fail safe to ensure that the suction/vacuum never exceeds a desired maximum operating range of −180 mm Hg to −220 mm Hg, preferably about −200 mm Hg, as this is all that can be attained by the system. In another embodiment, the maximum suction/vacuum capability of the tube 32 is greater than a desired maximum operating suction/vacuum. For example, the maximum suction/vacuum capability could be in the range of −220 mm Hg to −400 mm Hg. This greater capability provides an advantage in that, over time, should the tube 32 lose some of its elasticity/resilience performance, then the maximum operating suction/vacuum can still be achieved, due to the overdesign of the maximum suction/vacuum capability of the tube 32.

The elasticity/resilience properties of the tube 32 and inner housing 14 may be identical, for ease of manufacturing and keeping down costs of production. Alternatively, the elastic/resilience properties of the tube 32 may be different downstream of the compression members 36, 38, relative to the elastic resilience properties of the tube 32 in locations 40, 42. For example, the tube 32 downstream of locations 40, 42 may be more resilient than the tubing portions 40, 42, less resilient than tubing portions 40, 42 or even rigid. As noted above, the inner housing 14 may be resilient, semi-rigid or rigid. In at least one embodiment, the inner housing 14, tubing portions 40, 42 and tube 32 downstream of portions 40, 42 are all integral, made of the same material, and have the same elastic/resilience properties. In other embodiments, inner housing 14 may be more elastic, less elastic or equal in elasticity to regions 40, 42 and may be more elastic, less elastic or equal in elasticity to the elasticity of the tube 32 downstream of the regions 40, 42. The tube 32 may be itself resilient but the tube 32 may optionally also include embedded resilient members (like a coil or braid) which would enhance the resiliency or strength of tube 32.

The present disclosure is designed to emulate the application of forces applied by a baby suckling from the breast to extract milk. During breastfeeding the baby's tongue is applied to the nipple/areola region of the breast. During suckling the baby draws the tongue down and slightly backwardly to create a suction/vacuum to start drawing milk into the baby's mouth. The soft palate of the baby gets pulled against the back of the tongue thereby sealing off a suction/vacuum chamber forward of this contact, into which the milk drawn by the suction/vacuum. After an amount of milk is received into the baby's mouth, the baby swallows. Once the tongue re-contacts the hard palate, this releases the maxim suction against the breast and opens a passage to allow milk to be transferred into the pharynx and then esophagus. During swallowing, as the tongue moves up and seals against the hard palate, it creates a driving force to move the milk down the soft palate and into the esophagus. After swallowing the cycle is repeated by again drawing the tongue down and slightly backwardly. During the entire cycle, the baby maintains negative pressure (suction/vacuum) on the nipple/breast. The present disclosure provides the first compression element 36 to function like the baby's tongue and hard palate, to establish the constant suction against the breast, by sealing of the tubing in region 40. The second compression element 38 functions like the swallowing/soft palate function. In this way, milk ducts are not overly collapsed during a rest or lower suction pressure phase but rather the ducts are allowed to fill like when a baby is latched to a breast. This re-filling allows for more efficiency in milk extraction more similar to a baby than conventional pump devices.

Figure 4B:
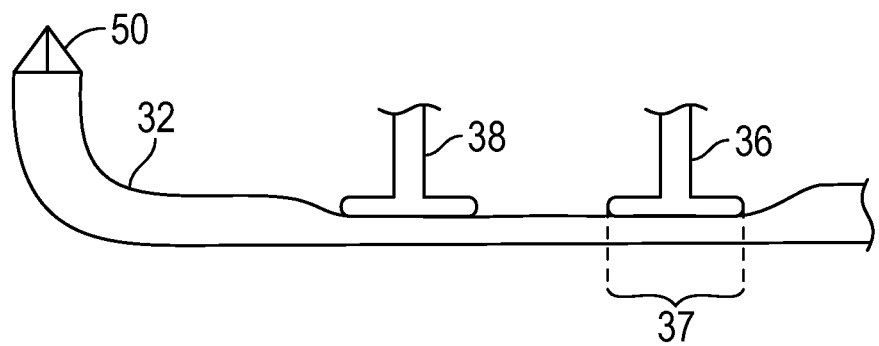

FIG. 4A shows the compression elements 36, 38 in a non-contact configuration (alternatively could be in contact, while not substantially compressing or deforming the tube 32) allowing the resilient tube to assume its full, un-deformed configuration. In this configuration, the cross-sectional area of lumen 56 is equal in the regions 40 and 42 to the cross-section area of lumen 56 in locations adjacent to 40 and 42 in the embodiment shown. In other embodiments, the cross-sectional area of lumen 56 in the regions 40 and 42 could be unequal to the cross-sectional area of lumen 56 in locations adjacent to 40 and 42. Further alternatively, the cross-sectional areas in the regions 40 and 42 could be unequal to one another. FIG. 4B illustrates the configuration of the compression elements 36, 38 in an initial state. The initial state is the state that the pumping region is placed in when attaching the system to the breast. Once a seal has been formed by the compliant region 12 with the breast and the system has been properly placed, it can be turned on to begin a milk extraction process.

Figure 4C:
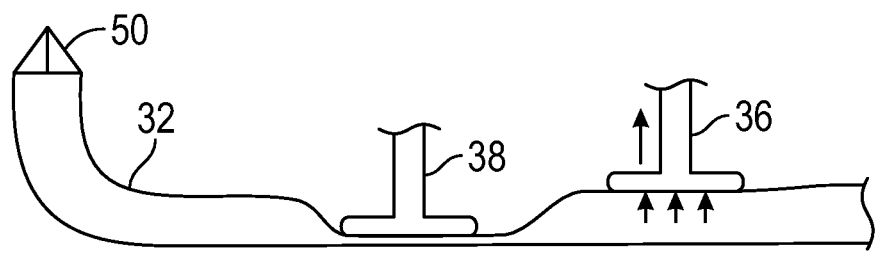

An initial suction/vacuum/suction is created by retracting compression element 36 (which is the compression mechanism nearer the breast) which allows the resilient tubing to spring back toward its initial shape to create a local suction/vacuum in the open segment 16 of the tubing and the inner housing 14 sealed against the breast. As the resilient tubing expands toward its un-deformed configuration, it creates a suction/vacuum in the lumen 56. FIG. 4C shows the compression element 36 having been fully retracted to establish the initial suction. Preferably, the tube 32 and the length 37 of compression member 36 are designed to establish a suction/vacuum by retracting element 36 as described, which is at the low end of a range considered to be sufficient for extracting milk. For example, tube 32 as shown in FIG. 4C could be configured to establish −120 mm Hg of suction/vacuum or −180 mm Hg suction/vacuum or some other suction/vacuum level less than −60 mm Hg to around −220 mm Hg. The suction/vacuum that is created is sufficient to draw milk from the breast and into the lumen 56 in a location distal of, as well as underneath the compression element 36. As the resilient tube 32 is now a closed system, the suction/vacuum is maintained with the lumen 56. The second compression member 38 can be withdrawn to further increase the suction/vacuum if desired, for example to accommodate the increase in pressure (less vacuum) as milk enters the system 100 from the breast 2. The member 38 can retract further in the direction away from tube 32 to compensate.

Figure 4D:
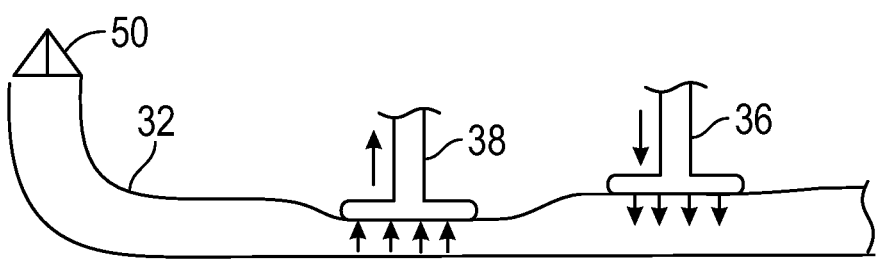
Figure 4E:
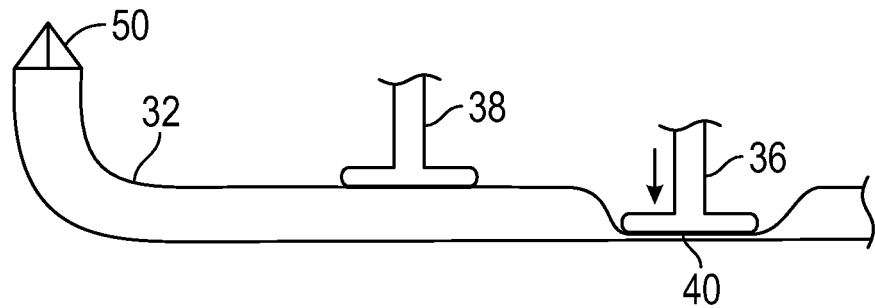
Figure 4F:
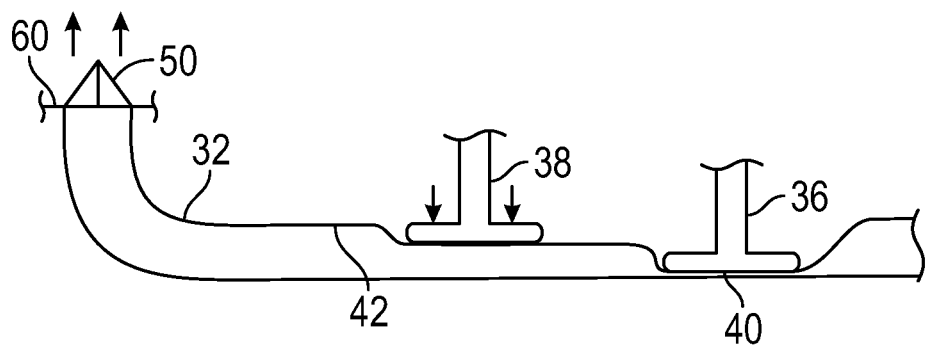

After a predetermined time or upon sensing a predetermined flow or volume of milk extracted, the milk is then passed through the tube 32 and valve 50 and into the container 60. FIG. 4D illustrates the second compression element 38 is starting to be retracted. At the same time the first compression element 36 is advanced to compress the tube 32 in region 40. The movements of 36 and 38 are coordinated to achieve and maintain a predetermined minimum suction/vacuum level, typically in the range of −40 mm Hg to −70 mm Hg, more typically −50 mm Hg to −60 mm Hg. The time of closure of the first compression element 36 may be pre-determined or the time for activation of closure of the first compression element 36 may be determined based on an algorithm that includes the pressure in the system 100, the mode in which the system 100 is operating (e.g., letdown phase, extraction phase or expulsion phase, etc.) and/or other data such as milk expression rate, and timing of the second compression element 38. As the first compression element 36 is advanced to close the first region 40, the second compression element 38 continues to be retracted to allow the second region 42 to continue opening, maintaining the desired minimum suction/vacuum profile throughout until the first region 40 is closed fully leaving a desired residual suction/pressure (at the minimum suction/vacuum level) against the breast. This action drives the milk proximally through the lumen 56 (driving to the left in FIG. 4D) as the suction is maintained. This is accomplished by retracting the compression element 38 at the same time that compression element 36 is extended to begin compressing the region 40. As the region 42 expands and the region 40 compresses, this drives the milk towards the one way valve 50. Thus, the second compression element 38 functions like the swallowing/soft palate of the infant and the one-way valve functions like the soft palate as it closes against the rear of the tongue during the peak suction phase to prevent backflow in the system. FIG. 4E shows compression element 36 fully compressing region 40, thereby functioning as a closed valve, maintaining the suction against the breast. Compression element 38 has been fully retracted, as the milk has been pushed into the location of region 42 and distally thereof. As noted previously, compression elements 36, 38 are not limited to the embodiments shown. As one alternative example, compression elements 36, 38 may function like clamps or pliers, each having two pads that squeeze together, compressing regions 40, 42 therebetween. FIG. 4F shows the compression element 38 again being extended, while the compression element 36 remains in the closed valve position. The compression of region 42 by element 38 can begin as soon as the region 40 is fully closed off by element 36 to seal off the region surrounding the breast. The compression by element 38 drives the milk out of region 42 and further downstream toward the one-way valve 50. When the compression element 38 reaches the fully closed (compressed) position, as shown in FIG. 4B, the cycle repeats, and the cycle of movements illustrated in FIGS. 4B-4F continues over the course of a milk extraction session.

The system 100 is capable of functioning successfully with the pumping tube 32 in any relationship/orientation, relative to the nipple, but it is preferred to location the compression regions 40, 42 and compression elements 36, 38 higher than the nipple 3 when the systems 100 is attached to the breast 2. In this arrangement, bubbles of air that may be fed through the tube 32 early in the pumping cycle so that the tube 32 is eventually mostly filled with milk, from the nipple 3 all the way to the one-way valve 50. The benefit of this is that the system 100 then becomes very energy efficient, as it approaches a fully hydraulic system. Since milk is essentially incompressible, the value of having a system 100 that does not have a substantial amount of air allows for suction pressure to be communicated sustainably within the system in a relatively uniform fashion with much less losses of energy into the fluid itself.

As noted, the pump mechanism requires independent, coordinated compression/release of two adjacent sections of resilient tube 32 to perform the extraction and delivery of the milk from the breast to the collection container 60. Although two drivers 44, 46 are shown in the embodiment of FIG. 3, alternatively, both compression elements could be driven by a single driver to move in a coordinated manner. However, two independently operating drivers are preferred, as they can be controlled more flexibly to vary the coordination between movements of the two compression elements 36, 38, if needed. The system 100 is capable of maintaining a negative pressure against the breast at all times similar to a normal breastfeeding baby.

In an embodiment which employs one or more pressure sensors 54 and controller 52, the pressure at the location(s) of the one or more sensors 54 can be monitored throughout the milk extraction process. During the opening of region 40 as described above with regard to FIG. 4C, the pressure is monitored until a desired milk extraction suction/vacuum level is achieved. In this case, the tubing 32 and compression element 36 dimensions can be designed to achieve a greater suction/vacuum than the low end of the range of suction/vacuum considered to be effective for extracting milk, for example, to achieve a suction/vacuum in the range of −180 mm Hg to −450 mm Hg. In this case, the feedback from the pressure sensor 54 to controller 52 lets the controller know when the desired suction/vacuum has been achieved and the controller 52 can control the driver 44 to halt the retraction of the compression element 36 at a position less than fully retracted, and thus still partially compressing the region 40, when the desired suction/vacuum level has been reached. Additionally or alternatively, in cases where full retraction of element 36 does not achieve a desired suction/vacuum level, element 38 can be retracted by an amount that brings the suction/vacuum level up to the desired suction/vacuum level.

The relative positions of the compression elements 36, 38 correlate to the volumes of the tube in regions 40 and 42 as long as the compression elements 36, 38 are in contact with the tube 32. Thus, by knowing the total volume of the remainder of the tube 32 and breast adapter 10 making up the suction/vacuum space, it is possible to estimate the volume of milk pumped by the system, once the tube 32 distal of the pumping region 30 has been filled with milk and the extraction phase begins, by calculating the volumes of regions 40 and 42 over the course of extraction and expulsion. Alternatively, additional information, such as provided by monitoring pressure changes at the breast 2; speed and direction of compression elements 36, 38; and/or force and/or pressure data history to the present time, may be used to calculate an estimate of volume pumped. Further optionally, a flow sensor or optical sensor may be employed to provide an estimate of volume and/or measurement of the extent of filling of tube 32 in a predefined region of the tube 32 to help in estimating the volume of milk pumped. By assuming the amount of fluid in the system 100 (tube 32 filled) and then knowing the pressure curve representing the pressure contained within the system 100 over time, any changes in pressure can take into account compression element 36, 38 position, speed and direction and then estimate the impact due to milk flow from the breast 2.

Figure 5A:
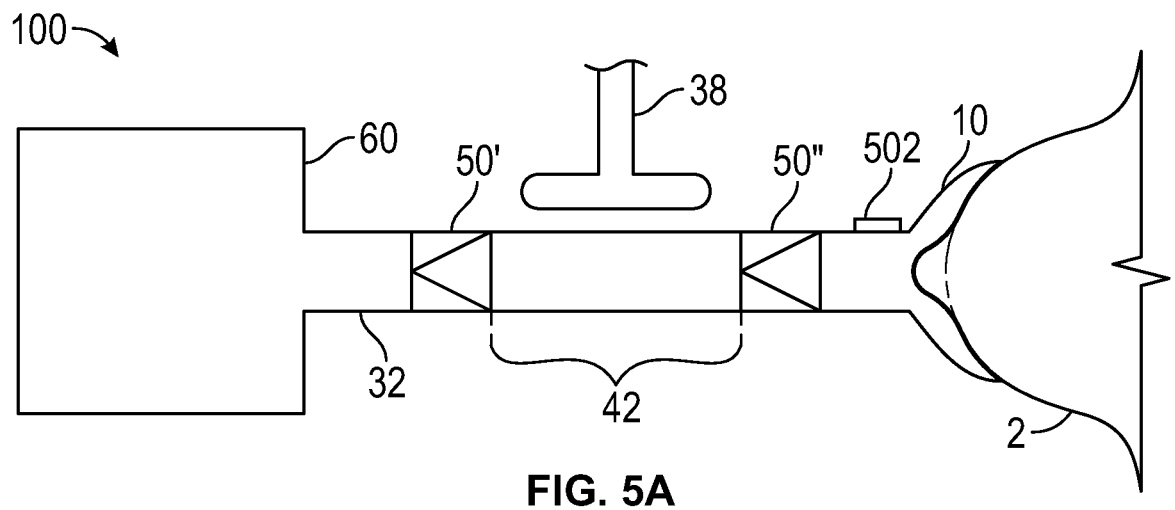
FIGS. 5A-5C illustrate operation of a system having only one compression element according to an embodiment of the present disclosure.
Figure 5B:
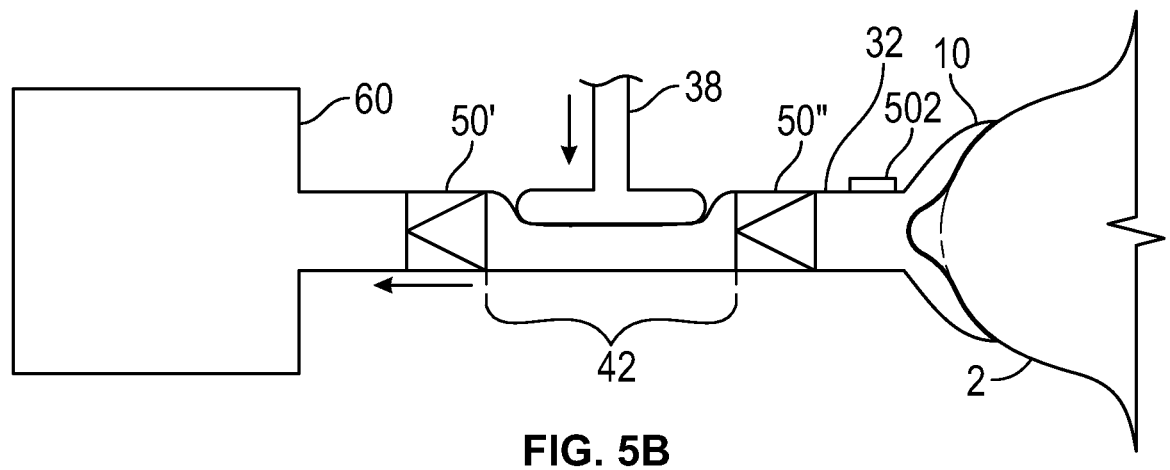
Figure 5C:
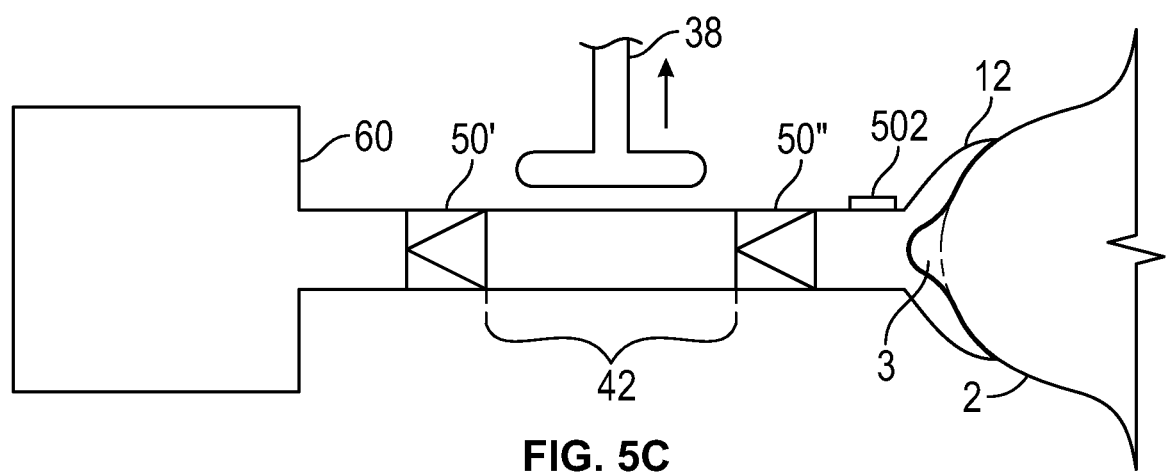

FIGS. 5A-5C illustrate operation of a system 100 having only one compression element 38 according to an embodiment of the present disclosure. In this embodiment, first and second one-way valves 50', 50" are provided adjacent opposite end of the compression region 42 of the tube 32 where the tube is compressed by compression element 38. FIG. 5A shows the initial configuration of the system when it is first applied to the breast 2. After a seal of the system 100 to the breast 2 is accomplished in any of the manners described previously, and letdown has occurred, pumping of expressed milk can be performed by compressing region 42 with compression element 38 as illustrated in FIG. 5B. As the pressure increases due to the compression of region 42, milk is driven through one-way valve 50' as indicated by the leftward directed arrow in FIG. 5B. At the same time, one-way valve 50" prevents backward flow of the milk and maintains vacuum against the breast 2. In FIG. 5C, as compression element 38 is retracted away from tube 32, tube 32 resiliently expands to increase vacuum (drop the pressure) in tube 32. This closes the one-way valve 50' and opens the one-way valve 50" to extract milk from the breast 2 and into the region 42. Extraction and pumping of milk can be continued by cycling between the phases shown in FIGS. 5B and 5C.

In order to prevent vacuum of against the breast from becoming too strong (limit pressure from going too low), the compression element 38 may be controlled by slow control of driver 46. If no flow of milk is detected, the driver 46 may be controlled to stop the pumping operation. Alternatively, the driver 46 may be controlled to pump for a predetermined amount of time past the detection of no flow, in order to further stimulate the nipple 3/breast 2 which may signal or condition the breast 2 to increase milk production. The system 100 can be provided with a relief valve 502 in or adjacent to the breast adapter 10. The relief valve 502 may be set to open when a predetermined maximum vacuum level has been reached, e.g., -200 mm Hg, -220 mm Hg or the like. This is typically the maximum vacuum level that is intended to be applied for expressing milk from the breast 2. The relief valve may be independent of the operation of the one-way valve 50" as shown, or alternatively, may be configured to squeeze or vibrate the one-way valve 50" so as to close it to prevent the vacuum against the breast 2 from exceeding the maximum predetermined vacuum. Once the one-way valve is overcome by the vibration or squeezing, the vacuum against the breast is prevented from exceeding the maximum vacuum.

Breast milk container 60 is preferably a flexible bag that is fitted over the main body/housing 34 in a collapsed state so that it does not take up any significant volume until milk is received therein, but closely follows the contours of the housing 34, so as to be received in a bra 130 and between the bra and housing, without enlarging the overall size of the system 100 as received in the bra. As stated, the container is also contemplated to be placed within the housing adjacent or about pumping structure, or alternatively, between pumping structure and the user's breast. The one-way valve is connected to the proximal end of the tube 32 (having been positioned in the channel 232) to complete the assembly of the system 100 to the condition shown in FIG. 1. Disassembly can be just as easily performed by reversing the order of the assembly description above.

Figure 6:
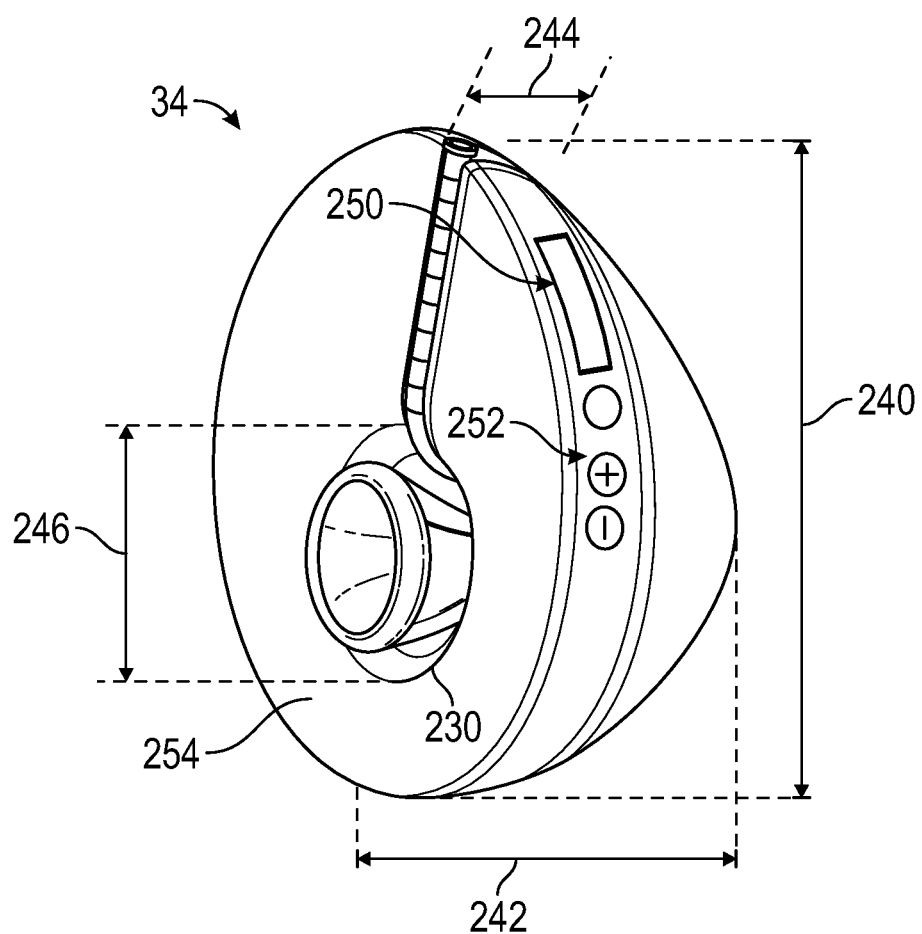
FIG. 6 illustrates a main body/housing of a breast pump system, without a container having been attached or the tube and adapter having been attached, to illustrate dimensions of the components shown, according to an embodiment of the present disclosure.
Figure 7A:
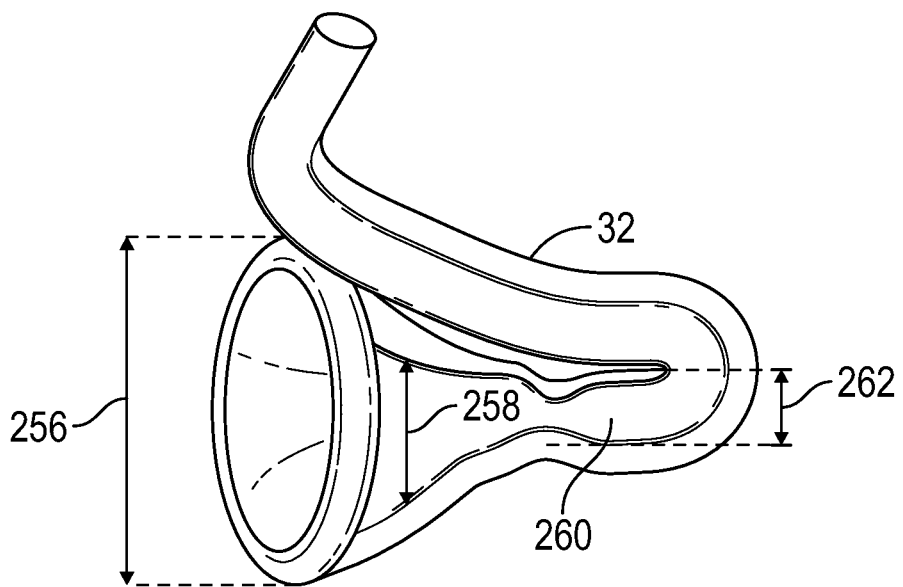
FIG. 7A illustrates a breast adapter/tube configured and dimensioned to be attached to the embodiment of the main body/housing of a breast pump system shown in FIG. 6, according to an embodiment of the present disclosure.
Figure 7B:
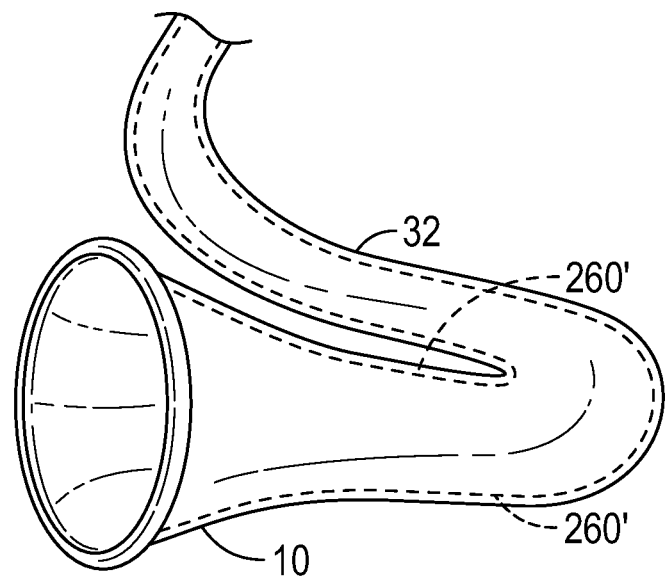
FIG. 7B illustrates a breast adapter/tube configured and dimensioned to be attached to the embodiment of the main body/housing of a breast pump system shown in FIG. 6, according to another embodiment of the present disclosure.
Figure 7C:
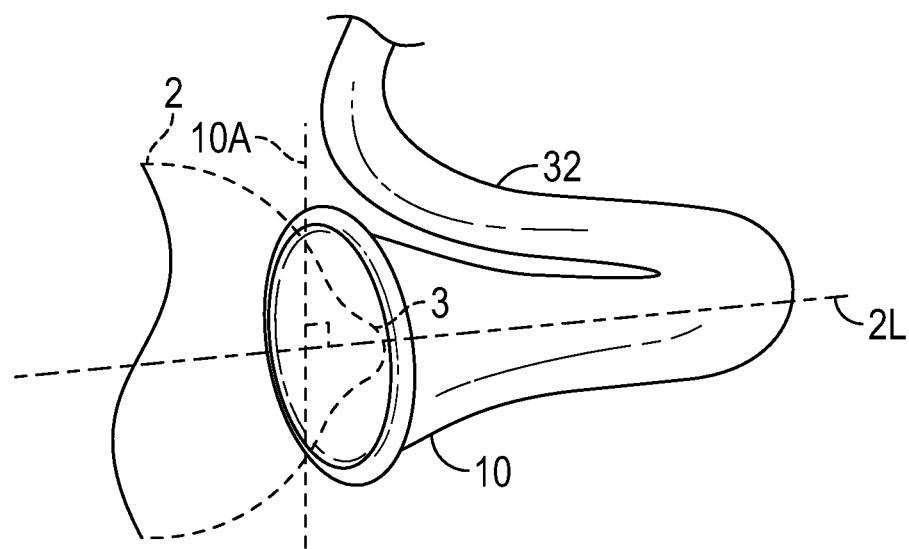
FIG. 7C illustrates a perpendicular relationship between a longitudinal axis of the teat and the breast adapter according to an embodiment of the present disclosure.
Figure 7D:
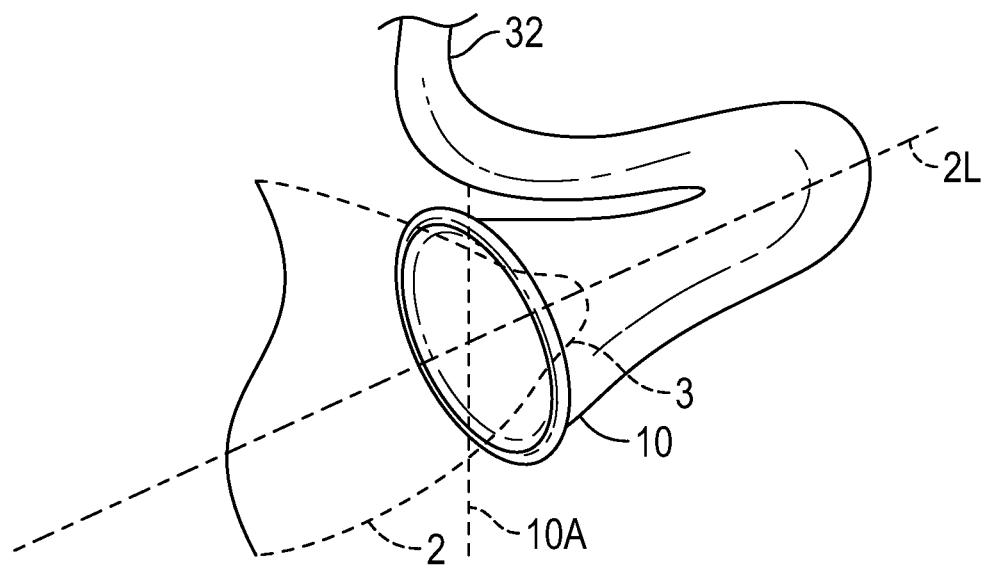
FIG. 7D illustrates an acute angular relationship between a longitudinal axis of the teat and the breast adapter according to an embodiment of the present disclosure.

FIG. 6 illustrates a main body/housing 34 of system 100, without a container 60 having been attached or the tube 32 and adapter 10 having been attached, to illustrate dimensions of the components shown, according to an embodiment of the present disclosure. It is noted here that the present disclosure is not limited to the dimensions disclosed with regard to FIG. 6, but may be varied, as this is only one specific embodiment of the disclosure. Any or all of the dimensions may be increased or decreased as needed, for example to adapt to different breast sizes, etc. The outside diameter 240 of the system housing 34 in FIG. 6 is 9 cm. The total thickness 242 of the device housing 34 (and thus the entire system 100 when container 60 is in the collapsed configuration) in FIG. 6 is 4 cm. The opening 244 at which the proximal end of tubing 32 is attached to the one-way valve has a diameter of about 13 mm. The receptacle 230 for housing the breast adapter 10 has a diameter 246 of 4.5 cm. Also shown is a display 250 which can be outputted to by controller 52, for example, to indicate if an air leak develops, what the current suction/pressure reading in the adapter 10 tube 32 is, approximate value of milk volume having been expressed, approximate flow rate of milk, pressure waveforms, phases of feeding timing, rest programming, heating applied to breast, vibration applied to breast, etc. The display can also indicate when the system is on and when it is off, duration time of a pumping session; time of day, date, count down times, speed or frequency of pumping cycles, strength of vacuum, etc. The display can be backlit to facilitating reading it in the dark. Additionally, controls 252 are provided to allow different modes of operation by the user, including, but not limited to: power up; on/off state indication; increases or decreases applied to various modes such as pumping cycle frequency, vacuum strength; selection of pumping program versions; timer, etc. The controls are conveniently located along an exterior surface of the device for easy access by a user. Alternatively, display 250 could consist only of a light, such as an indicator light. Further alternatively, a light may be provided underneath one or more of the controls 252 or where the milk tube 32 exits the main body 34. Such lights disclosed could be configured to illuminate in different colors to indicate various modes or information or may also flash. Additionally or alternatively, an audio feature such as a speaker and amplifier may be provided to produce one or a variety of sounds to alert the user to various modes, end of pumping session, time, various pressure thresholds being reached, etc. When display 250 is used to communicate volume of milk being pumped, duration of the pumping cycle, which mode the pump is in, or read out the pressure for min/max which could be settable by the user.

It is further noted that the receptacle 230 (for housing the breast adapter 10 and thus receiving the nipple) is not centered in the housing 34, but is positioned so that its center is below the center of the housing 34. This causes the system 100 to not be centered around the nipple of the breast, but to ride in a higher position, relative to the breast, so as to better conform to the anatomy of the user, and be less noticeable when worn in a bra 130. Additionally, the inner surface 254 is not flat, but is tapered. From the edge/periphery of the inner surface 254 to the inner nipple housing 230 the inner surface is tapered to form a cup shape. As the breast adapter 10 is placed against the breast 2, it is ideally concave to allow it to receive the breast 2 comfortably and provide a smooth surface to create an effective suction seal. Thus, surface 254 tapers slightly to conform to the breast 2, to still further make wearing of the system 100 less noticeable. There may be a slight bulge in the taper to provide a better sealing zone against/around the breast 2.

FIG. 7 illustrates a breast adapter 10/tube 32 configured and dimensioned to be attached to the embodiment of the main body/housing 34 of system 100 shown in FIG. 6. As with FIG. 6, it is noted here that the present disclosure is not limited to the dimensions disclosed with regard to FIG. 7 but may be varied, as this is only one specific embodiment of the disclosure. The outside diameter 256 of the breast adapter 10 at its opening in 4 cm. The inside diameter 258 of the breast adapter 10 in the region when the nipple is received is 20 mm as shown. The breast adapter necks down 260 at a location designed to minimize the distance that it is located beyond the extent that the nipple is stretched when it is formed into a teat under maximum suction/vacuum applied by the system 100. It is noted that the neck down region 260 is optional and is not included in many of the embodiments. If present, neck down region 260 is provided to create a light seal against the nipple/teat 3. Alternatively, a smooth wall of the breast adapter 10/tubing 32 is provided along the side to allow the nipple/teat 3 to move freely, as shown in FIG. 7B. The assemblies as shown in FIGS. 7A-7B (as well as the remainder of the system 100) is designed so that the interface or opening of the breast adapter 10A is substantially perpendicular to the longitudinal axis 2L of the breast 2 and nipple 3 as it is formed into a teat by the system 100. Alternatively, the breast adapter 10 may be configured so that the longitudinal axis 2L forms an acute angle with the opening surface or the breast adapter/back surface of the system 100, as illustrated in FIG. 7D. Such a configuration can reduce the thickness, or distance which the system 100 extends from the breast.

Figure 42:
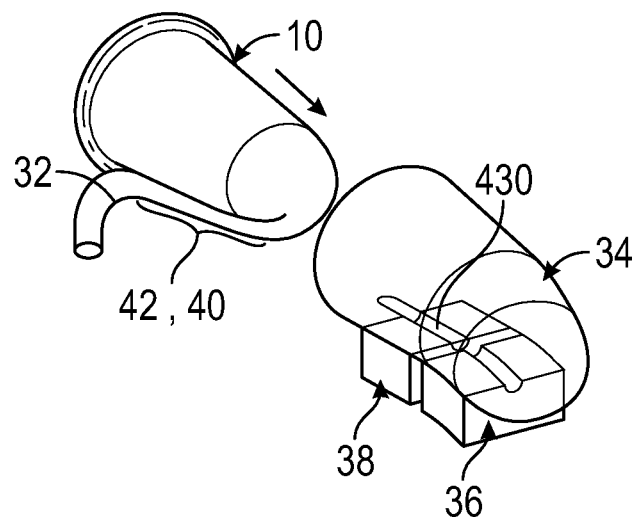
FIG. 42 is an exploded view showing where the tube of the system connects to the main body, according to an embodiment of the present disclosure.

The distance between the necked down region 260, or smooth region 260' that transitions to the tube 32 is preferably in the range of about 1 mm to 5 mm. The inside diameter 262 of the tube 32 where it integrates with the breast adapter 10 proximally of the neck region 260 is 20 mm in these embodiments. The tubing 32 then tapers down to an inside diameter of 6 mm in the regions to be compressed and proximal of these regions, all the way to the proximal end of the tube 32. The opening 244 of the main body 34 has an inside diameter of about 13 mm and is configured and dimensioned to accommodate tube 32 with some extra clearance, to allow the extension 62 (male embodiment) to overlap the tube 32. The breast adapter 10/tube 32 unit is configured to be removed from the system 100, as shown, for cleaning after use, and then reattachment in housing 34. The regions 40, 42 snap fit (or friction fit) between portions of the compression elements 38, 36 into groove or channel 430 upon attachment of breast adapter 10/tube 32 to the housing 34, see FIG. 42, so that regions 42, 40 can be compressed without impinging on the breast adapter portion 10.

Figure 8A:
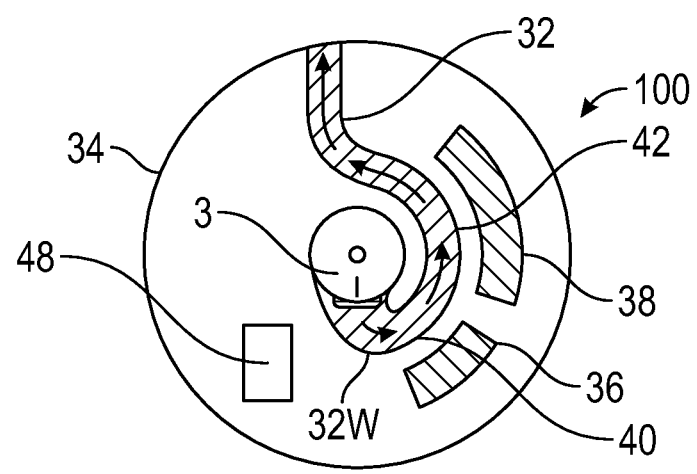
FIGS. 8A and 8B are schematic, front and side illustrations, respectively, of a breast pump system showing placement and routing of the tube, according to an embodiment of the present disclosure.
Figure 8B:
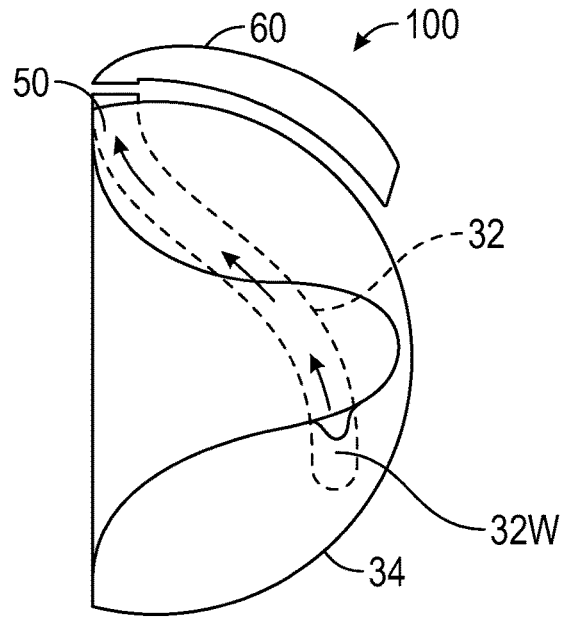

FIGS. 8A and 8B are schematic, front and side illustrations, respectively, of a breast pump system 100 showing placement and routing of tube 32 according to an embodiment of the present disclosure. In this embodiment, the distal end portion of tube 32 that integrates with the breast adapter that receives the nipple 3 of the breast is positioned below the nipple 3 so that it forms a milk collection well 32W to facilitate filling and priming of the pump region 40. Once milk enters tube 32 and into pump zone 40, the tube 32 can be routed in any direction. In the embodiment shown, the tube bends up and around the housing 34 to a location at the top of the housing 34 where it can be attached to container 60 with one-way valve therebetween. As noted, different routing schemes for routing the tube 32 may be used, such as routing to the side of the housing rather than to the top, or routing horizontally from the well 32W to the side of the housing 34 and then up and around to the top of the housing 34, or routing past the pumping regions shown in FIG. 8A and then back down to the bottom of the housing 34.

Figure 9:
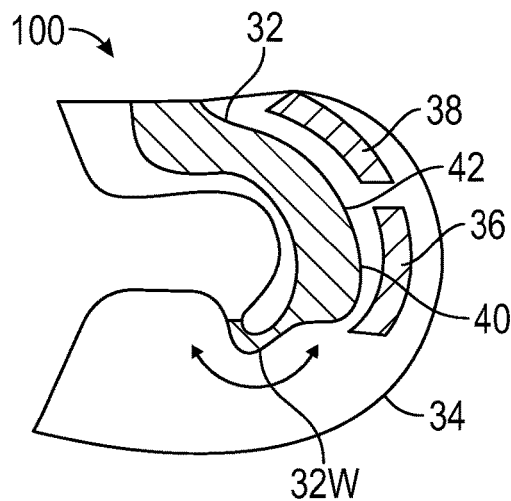
FIG. 9 is a schematic, side illustration of one example of a system having varying dimensions along the length of the tube, and optionally, varying materials from which the various portions of the tube are made, according to an embodiment of the present disclosure.

In some embodiments, it may be desirable to change dimensions and/or materials of the tube 32 along the length thereof. FIG. 9 is a schematic side illustration of one example of a system 100 having varying dimensions along the length of the tube 32, and optionally, varying materials from which the various portions of the tube 32 are made. Further optionally, the thickness of the wall of the tube 32 may vary along the length thereof to change resilience performance/compliance characteristics, whether the varying sections are of the same material or of different materials, as well as whether one or more sections are reinforced with braids, coils or the like to increase stiffness. In this embodiment, the well region 32W has the smallest diameter or cross-sectional dimension of any of the regions of the tubing, so as to minimize the volume of milk that needs to be collected in the pre-pump region of the tubing 32 before milk starts entering the pumping regions 40, 42 to be pumped. The pumping regions 40, 42 of the tube have the largest diameter, to allow more pressure change per length of tubing 32 to be generated, as a longer compression stroke by the activators 36, 38 is allowed. Downstream (proximal) of the regions 40, 42, the tube may be formed of a relatively more rigid material than that portion forming the regions 40, 42, in order to reduce the compliance and increase the flow of milk form the regions 40, 42 to the container 60. Additionally, or optionally, the portion of tube 32 downstream of region 42 may be formed to have a smaller diameter than the portions 40, 42.

Figure 10:
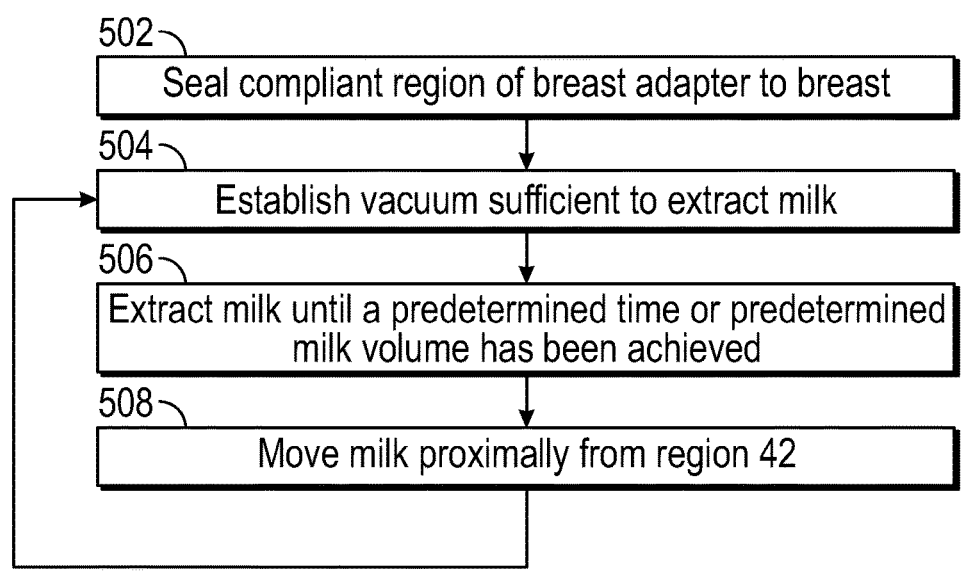
FIG. 10 illustrates a series of events that may be carried out in operating a system according to an embodiment of the present disclosure, when carrying out a milk extraction process from the breast.

FIG. 10 illustrates a series of events that may be carried out in operating a system according to the present disclosure when carrying out a milk extraction process from the breast. At event 502, the system is attached to the breast, which includes sealing the compliant region 12 of the breast adapter 10 to form a substantially airtight (the system can overcome and accommodate small air leaks) and substantially liquid-tight seal therewith to minimize or eliminate leakage of breast milk. There are different embodiments for accomplishing this task. A most basic and preferred embodiment is to form the seal by suction/vacuum alone. This can be accomplished by actuating a system actuator 82 (see FIG. 1) to power up the system and begin generating suction/vacuum. Actuator 82 may power up the controller 52 when present, or power up the drivers 44, 46 to run a predetermined routine when a controller 52 is not present. The establishment of the seal can be accomplished by retracting the first compression element 36 in a manner as described when going from the orientation shown in FIG. 4B to that of FIG. 4C. If a seal does not establish with the first retraction of element 36, then the element 36 can be cycled between the positions shown in FIGS. 4C and 4B until an adequate seal has been achieved. During cycling, as the element 36 compresses, this drives air out between the breast and the compliant region 12, and during each retraction of element 36, static suction (vacuum) is increasing built up, thereby increasing suction/vacuum within the breast adapter 10 and tube 32 with each cycle. In embodiments where a pressure sensor 54 and controller 52 are employed, the controller 52 can cycle the element 36 until a predetermined level of suction/vacuum has been achieved, which establishes that a sufficient seal has been formed. Advantageously, this cycling of the element 36 also facilitates let down of the breast milk, readying it to be extracted.

In an alternative embodiment, the seal may be established by a tacky or adhesive surface 84 may optionally be provided on an inner surface of compliant region 12 (see FIG. 2). The tacky surface may be provided by application of an adhesive, such as the type of adhesive used for stoma bags used for colostomy patients, or other effective and biocompatible adhesive or tacking agent. The sealing of the compliant region 12 against the breast may be established via the tacky surface 84 alone (or with a surface treated with a material that gets tack when heated by the body temperature of the breast 2 as it contacts the breast), or together with establishment of suction/vacuum as described in the previous embodiment. Further, optional application of pressure and/or heat may further facilitate sealing of the tacky region against the breast. In another embodiment, which may be used together with any of the previous embodiments, or by itself, the breast adapter 10 is configured to be compressed, once applied to the breast and then released. The breast adapter 10 then resiliently returns to its original configuration, thus establishing a suction/vacuum and sealing the compliant region 12 to the breast, much in the same way that a suction cup is stuck to a flat surface. In addition, the system may be handheld against the breast until sufficient suction/vacuum is established to generate the seal. Further optionally, the system may be supported in a bra configured to hold the system during its operation.

At event 504, the system establishes a suction/vacuum level sufficient to extract milk from the breast. This is accomplished by controlling movements of the compression element 36 and optionally controlling movements of compression element 38 in coordination with movements of compression element 36. An initial vacuum/suction is created by retracting compression element 36 (which is the compression mechanism nearer the breast) to create a local suction/vacuum against the breast. As the resilient tubing expands toward its un-deformed configuration, it creates a suction/vacuum in the lumen 56. FIG. 4C shows the compression element 36 having been fully retracted to establish the initial suction. Preferably, the tube 32 and the length 37 of compression member 36 are designed to establish a suction/vacuum by retracting element 36 as described, which is at the low end of a range considered to be sufficient for extracting milk. For example, tube 32 as shown in FIG. 4C could be configured to establish −120 mm Hg of suction/vacuum or −180 mm Hg suction/vacuum or some other suction/vacuum level less than −60 mm Hg to around −220 mm Hg. The suction/vacuum that is created is sufficient to draw milk from the breast and into the lumen 56 in a location distal of, as well as underneath the compression element 36. As the resilient tube 32 is now a closed system, the suction/vacuum is maintained with the lumen 56. The second compression member 38 can be withdrawn to further increase the suction/vacuum if desired. In embodiments where controller 52 and pressure sensor 54 are employed, feedback from the pressure sensor to the controller can indicate whether the suction/vacuum is sufficient to establish milk flow from the breast, as the pressure sensed will drop once milk enters the system. If the feedback loop between the controller establishes that extraction of milk has not yet begun, then the controller 52 can incrementally control retraction of the compression member 38 until sufficient suction/vacuum is established to cause milk to start to be extracted, as confirmed by the pressure-controller feedback loop. This control of the second compression member 38 can be subsequent to the fully retraction of the first compression member 36 or can be carried out during the retraction of the first compression member. Further alternatively, the first compression member may not be fully retracted, but some combination of partial retractions of the members 36, 38 can be established to achieve the desired suction/vacuum level. In instances where the predetermined suction/vacuum level that the tube 32 is designed to established upon full retraction of the compression element 36 alone is not sufficient to extract milk for a particular user, the controller can be programmed by the user to initially establish a suction/vacuum greater than that predetermined suction/vacuum level, so that the controller will automatically operate the compression elements 36, 38 initially to establish this greater suction/vacuum level, irrespective of pressure sensor feedback. The pressure-controller feedback loop can then still be used to adjust suction/vacuum as needed to extract milk.

Once the milk extraction has begun, the suction/vacuum is maintained at event 506 for a predetermined time, or until a predetermined volume of milk has been extracted, or when a predetermined minimum pressure has been achieved to indicate that a predetermined volume of milk has been expressed into the system 100. By continually measuring the pressure in the system (preferably, but not necessarily, in the vicinity of the nipple), an estimate of the volume of milk extracted can be calculated by the controller 52. As milk enters the suction/vacuum space, the pressure drops. The volume of milk received in the suction/vacuum space is proportional to the pressure drop and therefore the volume of milk can be estimated by knowing the pressure drop. This is also dependent however, upon ensuring that the seal between the system and the breast has not been broken and that no other air leaks have developed. As an air leak will register in the system as a continuous, somewhat constant pressure change toward zero, it can be readily distinguished from the changes in vacuum measured by receipt of milk into the suction/vacuum space, as these changes are less continuous and will continue to increase the pressure (reduce vacuum/suction), rather than remain relatively constant.

After the predetermined time has expired, or, more preferably, in embodiments where the volume of milk extracted is estimated, the milk is moved proximally from the region 42 at event 508, while sealing off the suction/vacuum space distal of the region 42, using compression element 36, while maintaining a constant suction/vacuum pressure on the breast/nipple that is less than the extraction suction/vacuum, as described above. This can be accomplished by compressing the tube 32 with element 36 while simultaneously retracting compression element 38 to maintain the desired suction/vacuum level until the seal is formed by element 36, as described above with regard to FIGS. 4D-4E. The rate at which the elements 36 and 38 are extended and retracted, respectively, and the amount of retraction of element 38 are dynamically adjusted depending upon the variables of the system, including the volume of milk present and the suction/vacuum level used during the extraction phase.

Once the compression element 36 has sealed off the tube 32 at region 40, the compression element 38 is immediately controlled to expel the milk from region 42 during the expulsion phase, by moving the milk proximally of the region 2. This is accomplished by extending the compression element 38, from whatever position it ended up in during event 506, to the fully compressed position to close off the tubing and drive the milk proximally from the region 42. This motion of the compression element 38 generates a positive pressure driving force, which is advantageous in that the milk can be pumped through the valve 50 and into the container 60 regardless of the orientation of the components, even directly against gravity. At this stage, the compression elements 36, 38 are positioned as shown in FIG. 4B and the processing returns to event 504 to carry out another cycle of milk extraction.

Figure 11:
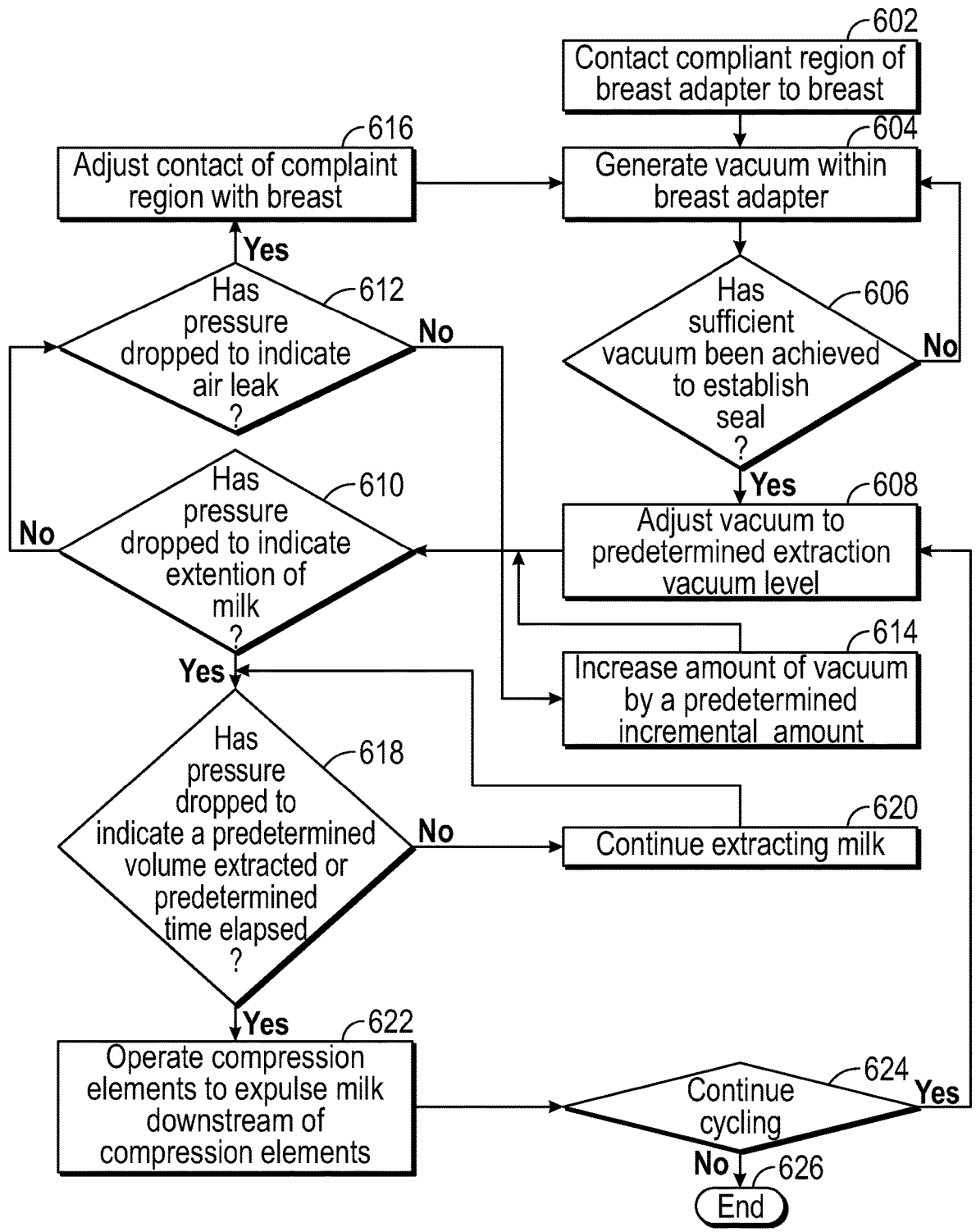
FIG. 11 illustrates events that may be carried out in a control process for extracting milk according to an embodiment of the present disclosure.

FIG. 11 illustrates events that may be carried out in a control process for extracting milk according to an embodiment of the present disclosure. At event 602 the compliant region 12 of breast adapter 10 is contacted to the breast such that the tube 32 is properly aligned with the nipple of the breast and a seal is established, in any of the manners already previously described. At event 604, suction/vacuum is generated in the breast adapter, which facilitates the sealing of event 602 if not already firmly established and establishes suction/vacuum to be used in milk extraction. The suction/vacuum pressure is continually monitored by the controller 52, either continuously or intermittently. At event 606, if a sufficient suction/vacuum has been achieved to establish the seal. An initial seal can be established by a vacuum that can be maintained in the pressure range of −1 mm Hg to −60 mm Hg, when the system 100 is supported by a bra 130. In practice, the system can be programmed with a threshold seal vacuum level confirming that a seal has been established, wherein the threshold seal vacuum level is in the range of −20 mm Hg to −60 mm Hg. In one particular embodiment, the threshold seal vacuum level is −40 mm Hg. Of course, it is understood that vacuum pressures of less than −60 mm Hg are also sufficient to establish the seal. If there are no leaks and a sufficient suction/vacuum (predetermined suction/vacuum level) has been established, then processing proceeds to event 608. If the pressure reading indicates that there is a leak or that a sufficient suction/vacuum level has not been otherwise established, then suction/vacuum is continued to be generated at event 604. This can be accomplished by cycling the compression element 36 in a manner as descried above. Additionally, if the pressure reading indicates an air leak, the user may readjust the interface between the compliant region 12 and the breast, which may optionally include adding an adhesive and/or holding or pushing the system 100 against the breast 2 until sufficient sealing vacuum has been established. The cycling from events 606 to 604 continues until sufficient suction/vacuum has been created to establish the seal.

At event 608 the suction/vacuum is adjusted to a predetermined extraction suction/vacuum level, which is greater that the residual suction/vacuum level that is applied to the breast at times when milk is not being extracted. This predetermined extraction suction/vacuum level can be any of those previously described above, and is established by controlling movements of the compression element 36 and optionally 38, as described above. The pressure continues to be monitored by the controller 52 in a manner as described above.

At event 610, if the pressure drops and the pressure drop is characteristic of receiving milk into the suction/vacuum space and that a seal has been maintained, then processing goes to event 618. If the pressure has not dropped in a manner to indicate receipt of milk in the suction/vacuum space, then at event 612 it is determined whether the pressure has dropped characteristically to indicate an air leak. If an air leak is indicated, then the user may be prompted, via an audible signal, or a message, such as on display 250, vibration of the system, automatic shutoff of the system, a signal or message sent to an external device such as a smartphone, or an indicator light, and the user can readjust the compliant region 12 contact with the breast to eliminate the air leak. Such adjustment may include any or all of: applying hand pressure on the system against the breast; rotating or otherwise repositioning the compliant region 12; removing the compliant region 12 from contact with the breast, applying adhesive to the compliant region 12 and reestablishing contact between the compliant region and the breast. Once the adjustment of the contact has been completed, the system returns to event 604. Distinguishing between an air leak and milk extraction is not necessarily important, as the system 100 is capable of adapting even if a consistent air leak is present. In the operating suction range, air leaks will be unusual and if such a leak exists it will be a big leak, such as when the system 100 is temporarily removed from the breast 2, and this will result in a much more rapid pressure rise than that due to milk extraction.

Referring back to event 618, if the pressure has dropped sufficiently so that the estimation of milk volume collected equals or exceeds a predetermined volume (e.g., a volume in the range of 0.02 to 0.064 oz., typically about 0.032 oz., then the system is controlled to change from the extraction phase to the expulsion phase at event 622 and the milk is expulsed downstream (proximally) of the regions 40 and 42 in an manner as already described. After expulsion has been completed, processing returns to event 608 to carry out another extraction phase of the cycle. The cycle can be continued for a predetermined time, or until a predetermined volume of milk has been estimated to have been extracted, or for a predetermined number of cycles, or for any combination of these endpoints, where the first endpoint reach will discontinue the cycling. Such decision is determined at event 624. Once the condition (predetermined time, predetermined volume of milk and/or predetermined number of cycles) has been met, the system shuts down at event 626. For example, for a typical pumping session in which 150 ml of milk is extracted and pumped, if the session last fifteen minutes, the system 100 pumps 10 ml of milk per minute. A baby suckling the breast 2 typically suckles about 30 times a minute. To replicate this, the system 100 cycles about thirty times a minute, with each stroke of the system 100 passing on average about 0.33 ml. (0.33 ml/cycle). Thus the volume capability of the pumping system 100 is configured to accommodate at least about 0.33 ml within each compression region (probably a bit more to allow for variation amongst women) but generally around that amount. As there is some natural "dead volume" between the nipple 3 and the first compression region 40, and then a desirable small amount of dead space between the last compressor 38 and the one way valve 50, this volume should also be compensated for in the volume capability of the system 100.

The present advantage provides extremely good control over the suction/vacuum pressure waveforms established by the system against the breast. In particular, the generation of suction/vacuum by the element 36 is closely adjacent the breast itself, so there is very little loss in the transmission of suction/vacuum pressure from the element 36 to the breast. In existing systems, suction/vacuum pumps are located at a much greater distance from the breast and pressure head losses of up to 200 mm Hg have been measured from pump to breast, in some instances. The distance 92 (see FIG. 12) between the compression element 36 and the end of the nipple when drawn into the open section 16 by suction/vacuum to form a teat 2' is minimized to maximize the responsiveness of the application of suction/vacuum to the breast. Additionally, the minimization of distance 92 helps to reduce the total amount of distance that the system extends from the breast when worn. When the teat 2' is maximally extended, the distance 92 may be in the range of about 0.5 mm to about 3 mm, typically about 1 mm to 2 mm.

The distance 94 (length of the compression member 36) is related to the amount of suction/vacuum to be achieved by moving the element from the position shown in FIG. 4B to the position shown in FIG. 4A. The length/distance of compression member may vary, depending upon the amount of suction and displacement desired by this component. For example, length/distance 94 may be a value within the range of 0.2 cm to 6 cm, typically about 2 cm. The distance 96 between the elements 36 and 38 should be minimized so as to minimize the dead space between the compression elements, as element 38 does not drive the contents in this space proximally, and it must be moved in the succeeding cycle. Thus, the larger the distance 96 is, the less efficient the expulsion phase is. The distance 96 can be a value in the range of 0 mm to 5 mm, preferably as close to 0 mm as can be achieved. The distance 98 (length of the second compression element 38) is designed so as to provide ample reserve suction/vacuum generation capability, so that the suction/vacuum pressure on the breast 2 can be dynamically adjusted to accommodate for a variety of different variables that occur when using by the same user, as well as across uses by different users including, but not limited to: vary rates of milk extracted, various amount of total volume of milk extracted (ranging from about 0 ml to 240 ml, typically about 76 ml milk per breast 2 per extraction session), amount of suction/vacuum needed to extract milk, etc. For example, length/distance 98 may be a value within the range of 0.2 cm to 6 cm, typically about 2 cm. The distance 102 between the proximal end of the second compression element 38 and the one-way valve 50 should also be minimized to reduce the volume of milk between the pumping mechanism and the valve 50, which does not get pumped out of the tube 32 until one or more successive cycles. In one example, distance 102 was a length holding a volume of milk when full of about 0.25 ml to 3 ml, typically about 1 ml.

Figure 13A:
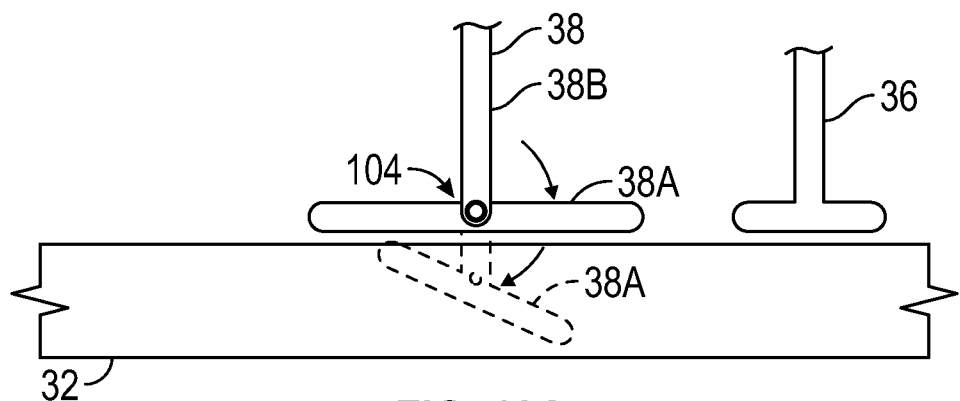
FIGS. 13A-13B show partial views of a system that employs a second compression element according to another embodiment of the present disclosure.
Figure 13B:
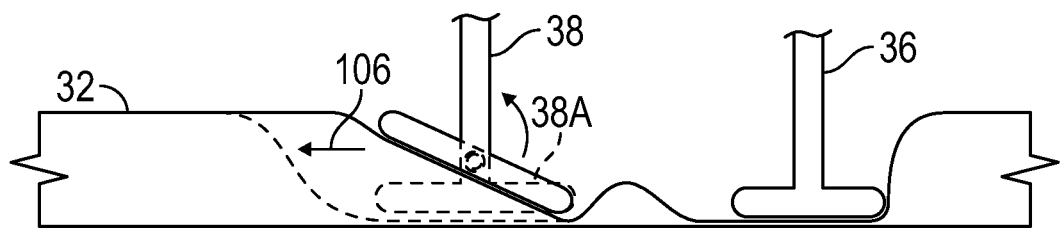

FIGS. 13A-13B show partial views of system 100 that employs a second compression element 38 according to another embodiment of the present disclosure. In this embodiment, the compression effector 38A is rotationally mounted relative to driver 38B via joint 104. As the compression element is advanced against the tube 32, the mechanism 104 rotates the compression effector 38A relative to the drive 38A (clockwise, as shown in FIG. 13B) so that the distal end portion of the compression effector 38A advances more than the proximal end portion as it rotates, as shown in phantom in FIG. 13A. At a predetermined distance (such as when the distal end portion of 38A seals off the tube 32, or at some other predetermined distance less than the distance required for sealing), the mechanism 104 reverse rotates the compression effector 38A (counterclockwise, as shown in FIG. 13B) to advance the proximal end portion of the compression effector 38A further against the tube 32. These actions provide a better force vector for expulsing the milk toward the one-way valve (in the direction of arrow 106), as compared to a compression element 38 having a compression effector 38 that does not rotate.

Figure 13C:
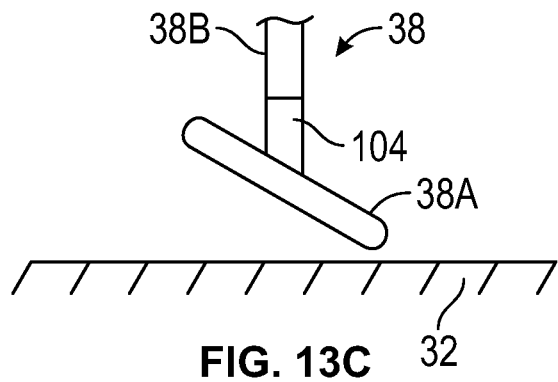
FIGS. 13C-13E show partial views of a system that employs a second compression element according to another embodiment of the present disclosure.
Figure 13D:
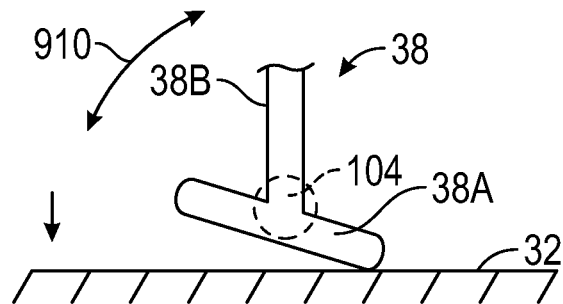
Figure 13E:
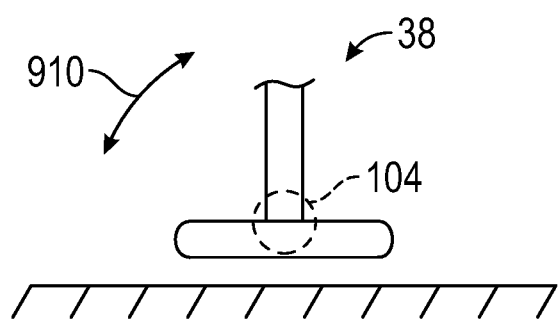
Figure 13F:
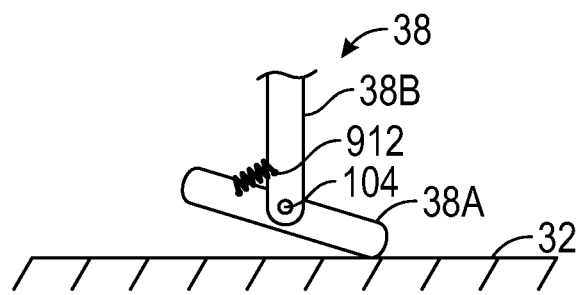
FIG. 13F shows a partial view of a system that employs a second compression element according to another embodiment of the present disclosure.

FIGS. 13C-13E show another rotational compression element 38 according to an embodiment of the present disclosure. In this embodiment, compression effector 38A and an upper portion of shaft 38B are relatively rigid, while a lower portion of the shaft, where it joins the compression effector 38A is elastic and forms the joint 104. As the compression element 38 advances toward tube 32, the lower portion of the compression effector 38A contacts the tube 32 first. As the compression element 38 continues its advance and begins compressing tube 32, the equal and opposite force pushing against the compression effector 38A by tube 32 deflects the joint 104 by the lever arm provided by the lower portion of the compression effector 38A applied against the joint. This causes rotation of the compression effector 38A (in the counterclockwise direction shown in FIG. 13D, increasing the angle 910). This rotation can continue until the compression effector becomes perpendicular to the shaft 38B and aligned with the tube 32, with angle 910 forming a right angle, as shown in FIG. 13E, depending upon the distance by which the compression element 38 is advanced against the tube 32. Upon retraction of element 38 away from the tube, joint 104 resiliently returns to its unbiased configuration as shown in FIG. 13C. FIG. 38F shows still another embodiment of compression element 38 configured to perform in the same manner as the embodiment of FIG. 13C, but where the elastic joint 104 has been replaced by a pin joint 104 and biasing member 910 interconnecting a portion of the compression effector 38A to the shaft 38B above the pin joint 104 so as to bias the compression effector 38A at a non-perpendicular orientation relative to the shaft 38B.

Figure 14:
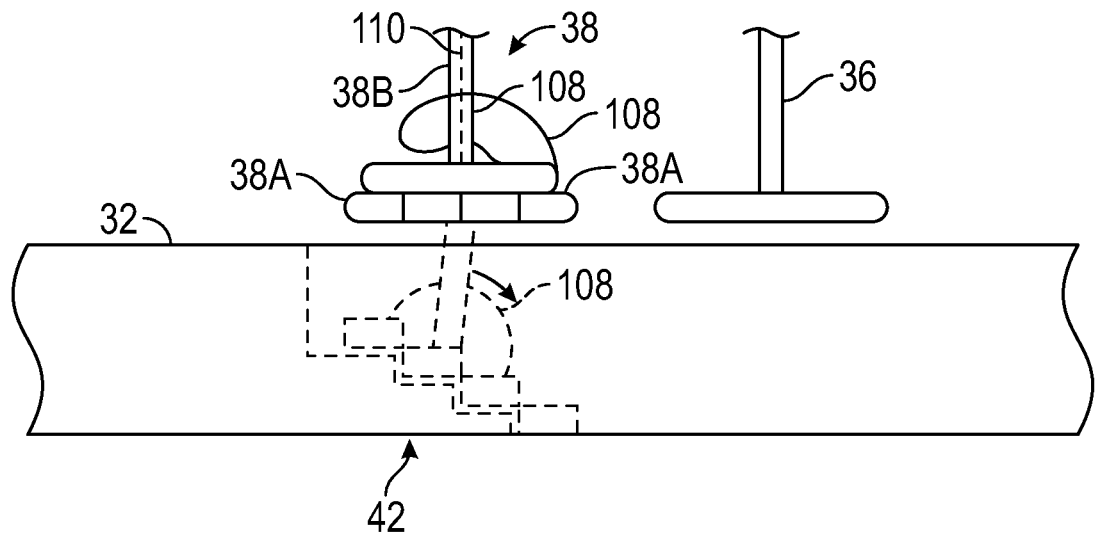
FIG. 14 shows a partial view of a system that employs a second compression element according to another embodiment of the present disclosure.

FIG. 14 shows a partial view of system 100 that employs a second compression element 38 according to another embodiment of the present disclosure. In this embodiment, the compression effector 38A is segmented to provide independently operable segments 38A that can be advance and retracted individually. Although four segments are shown in FIG. 14, more or fewer could be employed to operate in a similar manner to that described. Segments 38A are slidably mounted to driver 38B via a telescoping shaft 108 that is spring-loaded by biasing member 110 to bias the positions of the segments 38A relative to the driver 38B as shown in solid lines in FIG. 14. As the compression element 38 is advanced against the tube 32, cam 108 rotates relative to the driver (clockwise, as shown in FIG. 14) thereby contacting the distal most segment first and extending it from the driver 38A so that it extends into the tube 32 further than the other segments 38A. Upon further advancement of driver 38A and rotation of cam 108 the next-distal most segment 38A is contacted by cam 108 causing it to extend from the driver 38A. The process can continue until all segments have been extended like the distal most one shown in FIG. 14 to fully closes off the space 42. Upon retraction of the driver 38B, cam 108 reverse rotates and biasing member retracts the segments 38A relative to driver 38B to the positions shown in solid lines in FIG. 14 as they lose contact with the cam 108. Alternatively, the cam 108 can be designed to customize the final profile of the segments 38A when the driver 38B is fully extended, so as to arrange the amounts of extension of each individual segment 38A from the driver 38B by the distances desired. Further alternatively, the compression element 38 can be designed so that the driver does not need to advance at all, but instead extends and retracts the segments 38A though rotation and counter-rotation of the cam 108 and retraction forces provided by the biasing member 110.

Figure 15:
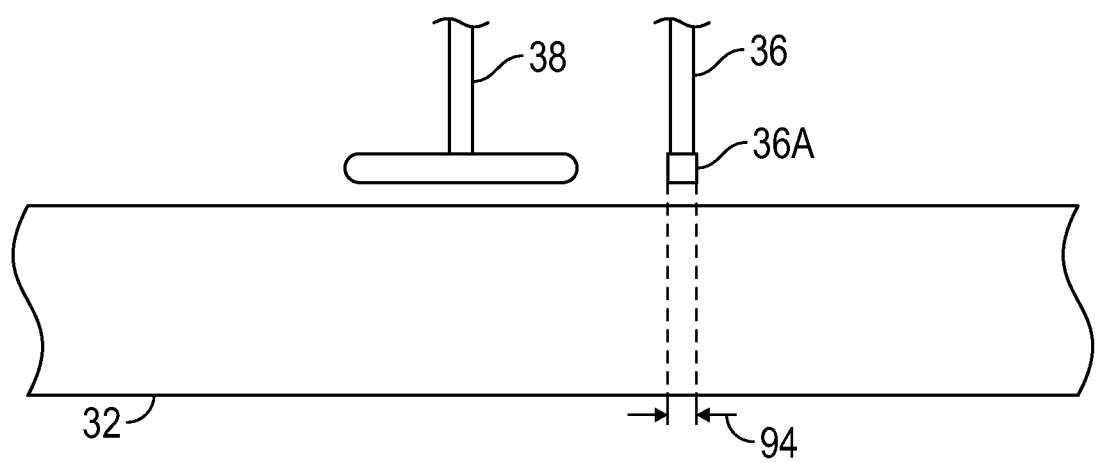
FIG. 15 shows a partial view of a system that employs a first compression element according to another embodiment of the present disclosure.
Figure 16A:
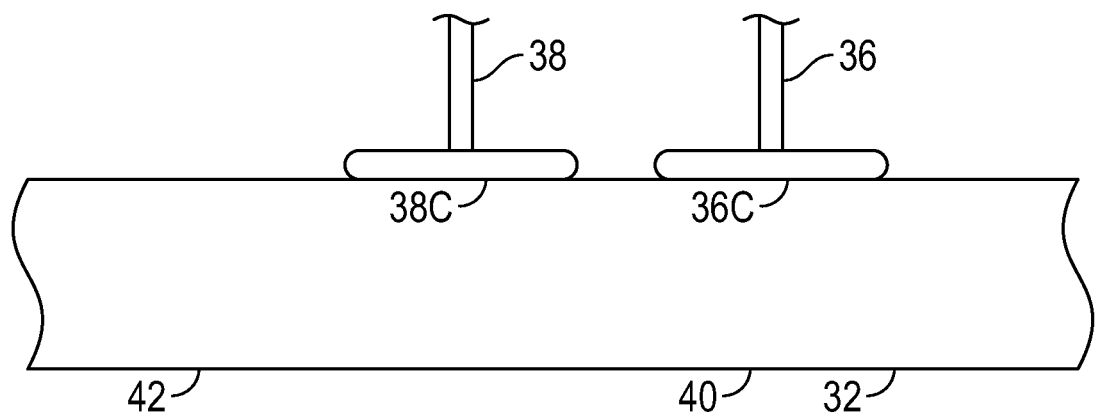
FIG. 16A shows a partial view of a system, according to another embodiment of the present disclosure, in which one or both of the compression elements are attached to the tube.

FIG. 15 shows a partial view of system 100 that employs a first compression element 36 according to another embodiment of the present disclosure. This embodiment of compression element 36 can be combined with any of the embodiments of compression element 38 described herein. In this embodiment, the compression effector 36A of compression element 36 is minimized, so that length 94 is in the range of about 1 to 4 mm, preferably about 1 to 2 mm, so that it is effective to seal off the tubing 32 (as described with regard to FIG. 4B), but operates in concert with compression element 38 to establish sufficient suction/vacuum for extracting milk. By minimizing the length 94, less force is required to seal off the tube 32, as compared to the force necessary to seal the tube using the compression element 36 in the embodiment of FIG. 14, for example, resulting in a savings of energy, which can lead to a smaller driver 44 being used, a smaller battery 48 due to the lower energy requirements, and/or longer operational time before the system 100 needs to be recharged or plugged in to an AC power source (in embodiments where this is possible). Response times of the system 100 may also be faster. The time required for the compression element 36 and the tube 32 to completely seal or release may be shorter. Also, there is less volume that is moved on the final close during feedback, so if the sealing element 36 is near closing and waiting for the pressure feedback controlling the larger compression element 38 to establish the desired pressure before closing, the smaller profile corresponds with less volume change on that final seal motion. Therefore the sealing can be more precisely and accurately controlled FIG. 16A shows a partial view of system 100 according to another embodiment of the present disclosure, in which one or both of compression elements 36 and 38 are attached to the tube 32. The compression elements are attached to the tube 32 at 38C along a portion or all of the surface of each of the compression elements that contacts the tube 32. The attachment may be by adhesive, welding and/or mechanical means such as banding, containment between jaws of a clamp formed by a compression actuator, screwing and sealing, bolting and sealing, or the like. The attachment provides the system with the capability of generating suction/vacuum by actively driving the portions 40, 42 of the tube. Thus, the suction/vacuum can be generated by a combination of forces provided by the elasticity of the tube sections 40, 42 and the driving forces applied by compression elements 36 and 38 or by the forces applied by compression elements 36 and 38 alone. One advantage that this arrangement may provide is that the response time of the tube 32 return to an uncompressed state could potentially be sped up by rapid movement control of the compression elements 36, 38.

Figure 16B:
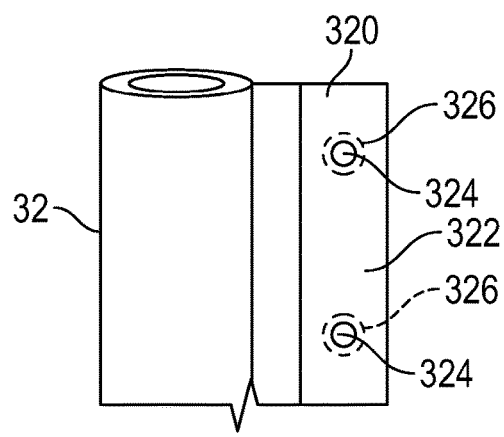
FIG. 16B illustrates one way in which the tube can be configured for attachment to one or both of the compression elements, according to an embodiment of the present disclosure.
Figure 16C:
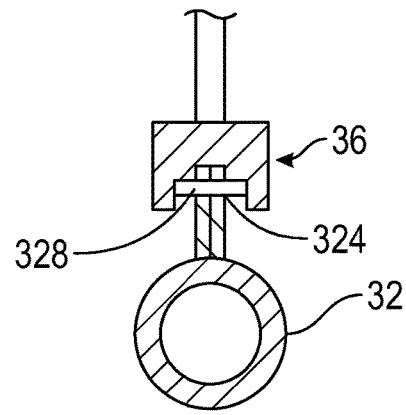
FIG. 16C is a partial cross-sectional illustration of the first compression element attached to the tube, according to the embodiment described with regard to FIG. 16B.

FIG. 16B illustrates one way in which tube 32 can be configured for attachment to one or both of compression elements 36, 38, according to an embodiment of the present disclosure. In this embodiment, a tab 320 is integral with tube 32 and extends radially therefrom to be connected to a compression element 36, 38. Tab 320 may be made of the same material as tube 32 and integrally molded therewith, or may be laminated to tube 32, or otherwise integrated therewith. Optionally, tab 320 may be reinforced by a reinforcing layer 322, such as a fibrous mesh or other layer of material that is tougher than the material making up the tab. The reinforcing layer may be laminated inside of the tab material or provided as a backing layer. Openings 324 are provided to facilitate connection of the compression element 36, 38 to tab 322. Openings 322 may be optionally reinforced by rings or grommets 326 integrally joined in the openings by molding, welding adhesive or other expedient. FIG. 16C is a partial cross-sectional illustration of compression element 36 attached to tubing 32 according to the embodiment described with regard to FIG. 16B. A pin or rod 324 passes through opening 324 and connects to compression element 36 at both ends. In an arrangement where a compression element 36, 38 connects to tubing 32, the actuation of the compression element 36, 38 can assist in tube 32 expansion, thereby increasing the speed at which the tube 32 rebounds from a compressed configuration and/or increasing force applied by expansion of the tube 32.

Figure 17A:
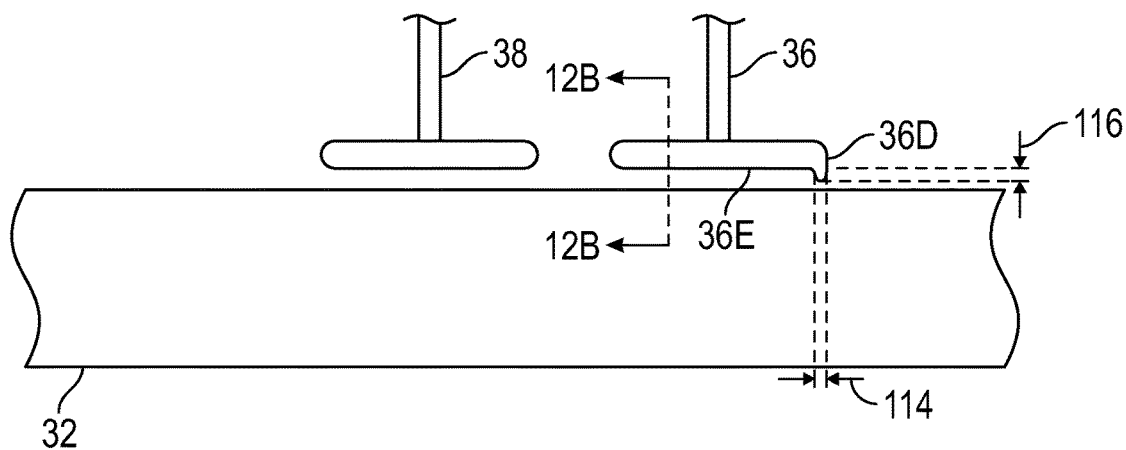
FIG. 17A is a partial view of a system employing another embodiment of compression element, according to an embodiment of the present disclosure.

FIG. 17A is a partial view of a system employing another embodiment of compression element 36. In this embodiment a small protrusion 36D extends across the width of the compression effector 36A so that it is sufficient to span the width of the tube 32 and seal it off when the compression element 36 is fully extended. Because the length 114 of the protrusion is very small, for example, in the range of about 1 to 4 mm, preferably 1 to 2 mm, there is much less force required to be applied to the compression element 36 to seal off the tube as compared to sealing off the whole length of the compression effector 36A, like what occurs in the embodiment of FIG. 14. Likewise, the depth 116 by which the protrusion 36D need not be great, in the range of 1 to 10 mm (with the maximum equal to the outside diameter or height in non-circular cross-section embodiments) of the tube 32, preferably 1 to 3 mm. Of course the length of the protrusion 36D is not limited to the preferred values described, as any length short of the entire length of the compression effector 36A could be employed, but the shorter the length, the greater the energy savings. Likewise the depth 116 could vary from the ranges supplied, but as the depth increases, the volume displaced by the remainder of the compression effector will consequently decrease, so there will be a tradeoff between energy saved and volume displaced, that being an inverse relationship.

Figure 17B:
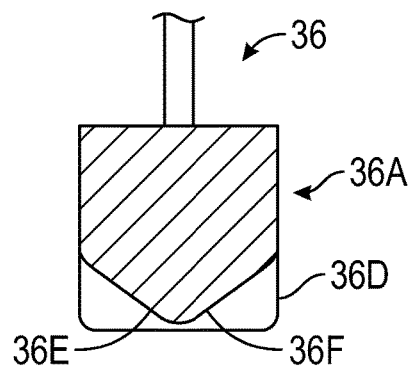
FIG. 17B is a cross-sectional view of the compression element in FIG. 17A.

FIG. 17B is a cross-sectional view of the compression element 36 taken along line 12B-12B in FIG. 17A. This view shows that the remainder of the contact surface 36E (excluding the protrusion 36D) is contoured to further reduce energy expenditure while retaining substantial ability to displace volume. In this embodiment, the cross-sectional shape of the contour 36E is substantially V-shaped or U-shaped, so that the ridgeline 36F that runs longitudinally of the compression effector 36A, preferably, but not necessarily midway of the width of the compression effector 36A and aligned with the longitudinal axis of the effector 36A. The ridgeline 26F contacts the tube 32 first and presses into it, and, with increasing compression, more and more of the contoured surface contacts and compresses the tube. However, none of the contoured surface 36E seals off the tube, as that function is provided solely by the protrusion 36D.

In the embodiments discussed thus far, the compression elements 36, 38 compress the tube 32 against a substantially flat "anvil" surface of the channel 232 in the 34 into which the tube is installed. FIG. 17C is a cross-sectional illustration of compression element 36 with tube 232 being received in a channel 232 formed with a substantially planar or flat anvil surface 232A. Note that the width 232W of the channel 232 is greater than the outside diameter of the uncompressed tube 32, so there is room for the compressed tube 32 to widen as it is flattened. Also, the width of the compression element 36 is greater than the outside diameter of the uncompressed tube 32, typically having a width about equal to the width of the fully compressed tube 32. Alternatively the anvil surface 232A of channel 232 may be substantially V-shaped in cross-section, as illustrated in FIG. 17D and the compression element 36 (and/or 38) may have a compression surface 36S that is substantially V-shaped. This results in a relatively lower force required to be applied by the compression element 36 to completely seal off the tube 32, compared to the amount of force required to seal off the tube 32 in the embodiment shown in FIG. 17C. Still further, other non-flat anvil surfaces 232A can be provided to lessen the overall force required by the compression element 36 to seal off the tube 32. Another non-limiting example of this is illustrated in FIG. 17E, where the anvil surface 232 is concave, and the compression surface 36S is convex.

The rebound/recoil stored energy in the resilient tube 32 itself is the primary if not sole means for generating suction within the system 100 in preferred embodiments, as described above. As also described herein, one or both compression elements 36, 38 may be attached to the tube 32 to supplement the recoil force of the tube 32. The vacuum is generated by change in volume in the chamber/tube 32. As noted previously, tube 32 need not be circular in cross-section, but could be any shape chamber where volume changes (with valves) generates the vacuum. The action of the rebounding walls of the tube/chamber 32 creates the vacuum. Other means of moving the walls can be magnetic, e.g., both compression elements 36, 38 driven by various electromagnetic means to move them. Alternatively, electromagnetic members may be embedded into or attached on the tube/chamber 32 walls that can be electromagnetically driven to change positions of the walls to create the vacuum. Further alternatively, shape memory alloys (e.g., NITINOL, or the like) can be built into or on the walls such that there is a pre shape/configuration and then with current, the shape changes and affects a shape change in the tube geometry. The shape can start or be activated to compress the tube 32. Still further, any other structure/means to change the state of a material via electricity or other means can be employed so that the change in state drives a change in geometry of the tube/chamber 32 to change volume. The system 100 is capable of maintaining a negative pressure against the breast at all times similar to a normal breastfeeding baby. The breast 2 includes ducts through which the milk is expressed. As the expression suction/vacuum level is applied to the breast, the diameter of the ducts increases due to the suction/vacuum causing the expression of milk from the ducts. As the milk is expressed from these ducts, they become substantially depleted and collapse. This is typically when the baby swallows or when a milk extraction system cycles to wait for the next extraction phase. In existing systems where the suction/vacuum is reduced to zero (atmospheric pressure) between extraction phases, the ducts contract and do not allow expression of milk, but allow some refilling of milk to occur from larger ducts upstream of the ducts that open to the surface of the nipple. In the case of the nursing baby, as well as use of the present system 100, the suction/vacuum applied to the breast between extraction phases (swallowing in the case of the baby, expulsion phase in the case of the present system) is maintained at a lower suction/vacuum pressure than the extraction suction/vacuum, but still greater than atmospheric pressure. In one non-limiting example, the extraction suction/vacuum is about −200 mm Hg and the intermittent suction/vacuum applied to the breast, between extraction phases, is about −50 mm Hg. This suction/vacuum applied between extraction phases is not great enough to extract milk from the nipple, but is sufficient to maintain a certain level of expansion of the radii of the ducts to allow more refilling to occur between extraction phases, while not allowing substantial extraction of milk.

The drivers 44, 46 are each stepper motors in at least one embodiment, that are controlled by controller 52. Since the compression driver 36 can be controlled to be always in either a fully open position or a fully closed (sealed) position, it can be operated by a motor-driven cam, rather than a stepper motor, since it does not need any sophisticated stepper-motor drive input. In this case, the compression driver 38 can be controlled by a stepper motor for dynamic adjustment, via a feedback loop to the controller 52 that controls the stepper motor 46 to: position the compression driver 38 to ensure the desired residual suction/vacuum is applied to the breast when compression driver 36 seals off region 40; drive the compression driver 38 to generate the appropriate pressure wave form to expulse the milk; and drive the compression driver 38 at a controlled rate and pressure of expulsion of milk across the one-way valve 50. Alternative drivers that can be used as drivers 44, 46 include, but are not limited to: an electromagnet on one side of the compression element 36 or 38 with an iron or magnetic core on the other side of the tubing, opposite the compression element, such that when current is activated, the compression element compresses against the tube 32; cammed motors; or motors driving clamps on a linear or rotational rack and pinion drive train.

Figure 18:
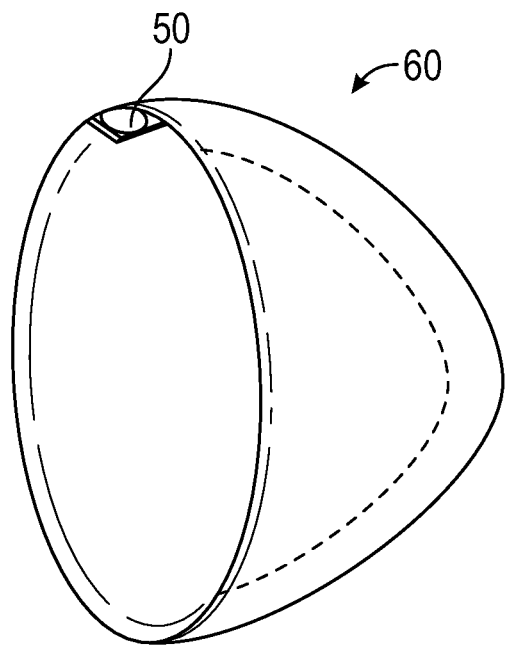
FIG. 18 is an isolated illustration of a milk collection/storage container according to an embodiment of the present disclosure.

FIG. 18 is an isolated illustration of the milk collection/storage container 60. In the embodiment as shown in FIG. 18, container 60 is a flexible, hemispherically shaped bag that envelopes the main body 34 of the system when installed on the system. The one-way valve 50 is preferably provided as integral with the container 60, as shown, but could alternatively be made to be removable, or could be integrally or removably attached to tube 32. By providing the one-way valve 50 within the tubing integral to the container 60, this allows the container 60 to be immediately sealed once detached from tube 32, which avoids leakage. Container 60 is preferably a compliant bag made of a biocompatible, food grade material such as LDPE. Alternative materials that can be used include, but are not limited to: linear low density polyethylene (LLDPE), polylactic acid (PLA), polyvinyl chloride (PVC), ethylene vinyl acetate (EVA), high density polyethylene (HDPE) or polyethylene terephthalate (PET).

The collection of milk into container 60 is performed under the positive pumping force/pressure of the pumping mechanism/region 30. Thus the system 100 does not rely on gravity for collection of milk in the container 60. This is advantageous, as it allows breast milk to be extracted and collected over even an uphill gradient, such as may occur when the user is lying down, bending over, or in environments such as a bumpy ride, as in an automobile or airplane trip. This further allows flexibility as to where the collection bag/container 60 (and the input thereto) is located relative to the nipple of the breast. For example, the container 60 could be placed near, on, above, below or on the side of the breast. In the embodiment shown in FIGS. 1 and 5, the input to the container 60 is above the breast when system 100 is mounted to the breast. This facilitates easier attachment of the container 60, removal of the container 60 when full or needed to be used, and replacement of another container 60 on the system 100.

Figure 19:
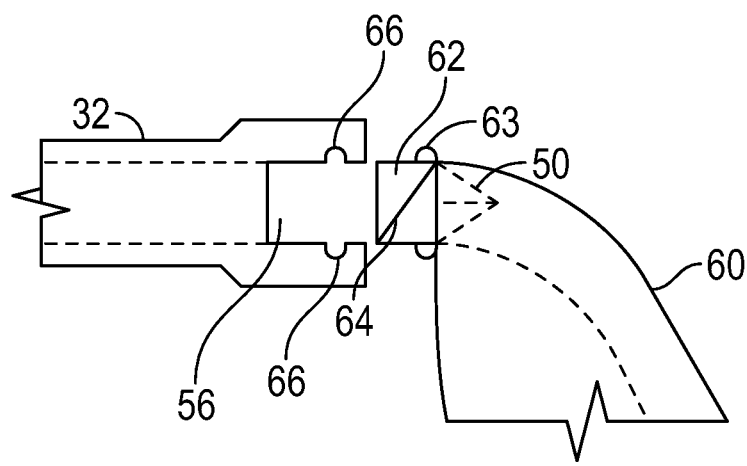
FIG. 19 illustrates the connection features of the tube and container that allow for easy and rapid attachment and detachment of the container to and from the tube, according to an embodiment of the present disclosure.

FIG. 19 illustrates the connection features of the tube 32 and container 60 that allow for easy and rapid attachment and detachment of the container to and from the tube 32. An extension 62 of the one-way valve 50 is configured to form a snap fit, or lock via a detent 64 with a mating receptacle 66 in a proximal end portion of tube 32 to rapidly establish and gas-proof and liquid-proof seal. One or more seals such as O-ring 63 or the like can be provided at the junction to facilitate the sealing process. For example, in the detent and receptacle arrangement shown, the container 60 can be easily and rapidly attached to the tube 32 by inserting the extension 62 into the proximal end of the lumen 56 and turning the extension 62/container 60 a quarter turn. Detachment can be just as easily performed by turning a quarter turn in the opposite direction. Other quick-connect mechanisms that are capable of establishing a quick and easy liquid-tight and gas-tight connection could be substituted for those described. It is noted that the connection mechanism could alternatively be reversed, with the male portion being on the proximal end of the tube 32 and the female portion begin on the extension 62. Further alternatively, the one-way valve 50 could be integrally formed at the distal end of the tube 32 with either a male or female extension and the mating component of the connection mechanism could be integrally formed at the opening of the container 60.

Figure 20:
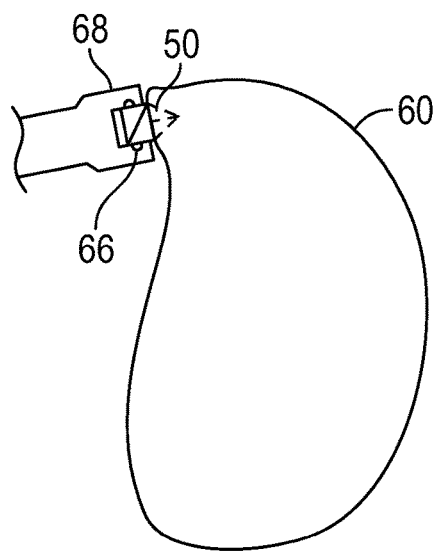
FIG. 20 illustrates a container having been capped off upon removal from the system, according to an embodiment of the present disclosure.
Figure 21:
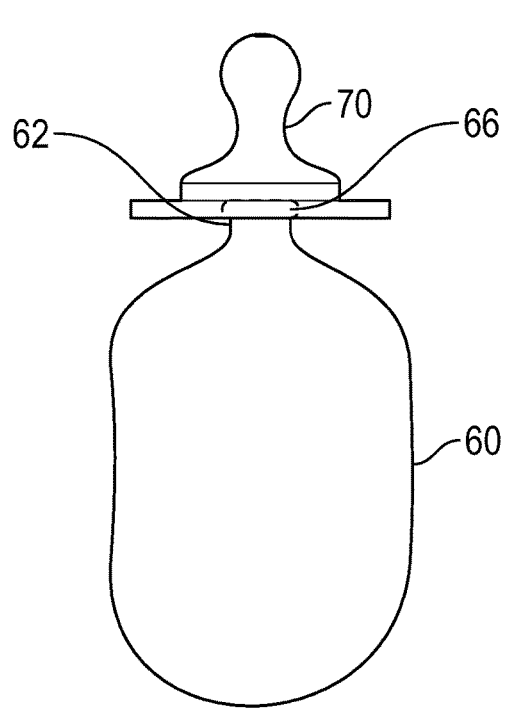
FIG. 21 illustrates a feeding nipple attached to a container according to an embodiment of the present disclosure.

Upon removal from the system 100 (as well as prior to connecting the container 60 to the system 100), the container 60 can be capped to prevent exit of fluid therefrom and also prevent air from entering the container, as illustrated in FIG. 20. Cap 68 is provided with the same mating mechanism 66 as that found at the proximal end portion of tubing 32, so that cap can be twisted a quarter turn, snap fit, or otherwise attached to extension 62 in the same way that extension 62 forms a connection with tubing 32. Still further, a feeding nipple 70 can be attached to extension 62, as shown in FIG. 21, in the same manner that tube 32 and cap 68 are attached, to form a liquid-tight and gas-tight seal with the extension, to allow feeding of a baby directly from the container 60. Thus, a container containing milk can be configured for immediately feeding a baby after removing the container 60 from the system 100. Alternatively, container 60 can be capped and stored in the refrigerator or freezer for later use.

Figure 22:
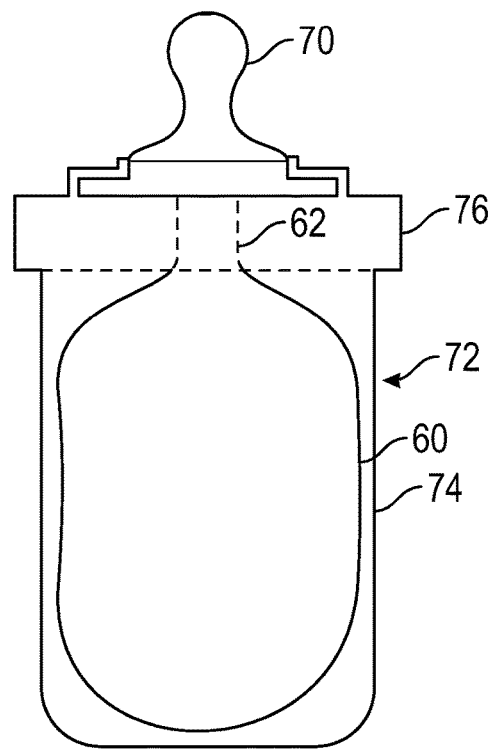
FIG. 22 shows a bottle that the container with the nipple attached thereto inserted therein to provide a more structural implement that is more easily used for feeding a baby, according to an embodiment of the present disclosure.

FIG. 22 shows a bottle 72 that the container 60 with the nipple 70 attached thereto can be inserted into and contained to provide a more structural implement that is more easily used for feeding a baby. Bottle 72 includes a hollow shell 72 configured and dimensioned to receive the container 70 while allowing the nipple 70 to extend out of the open end thereof. A bottle cap 74 has an opening that allows the nipple 70 to extend therethrough and is configured and dimensioned to enclose the open end of the shell 74 when the bottle is assembled. Bottle cap 74 can be fixed to shell 74 by mating threads, bayonet fitting, snap fitting or other similar arrangement. The assembled bottle 72 as shown is ready to use for feeding a baby, or alternatively can be stored in the refrigerator or freezer for later use.

FIG. 23 is an exploded view of an alternative arrangement for installing container 60 in a bottle 72 and providing it with a feeding nipple 70. In this embodiment an insert adapter 120 is provided to adapt the container 60 to be used with a commercially available nipple 70 and bottle 72 that are currently sold and readily available. The insert adapter is provided with a valve defeat extension 122 which contains a central lumen 124 that is in fluid communication with the annulus 126 of the adapter 120. The valve defeat extension 122 is configured and dimension to be inserted through the one-way valve 50 to hold it open and allow milk to be sucked out through the valve defeat extension and nipple 70. In another embodiment, the one-way valve is removable and is removed prior to installation of the adapter 120. The top surface 128 of the adapter 120 is flat and configured to form a fluid-tight, airtight seal with the flat bottom surface of the nipple 70. The container 60 is dropped or placed into the bottle 72 after inserting the valve defeat extension 122 through the one-way valve 50. The threads 70T of the bottle are engaged by mating threads 120t at the bottom portion of the adapter and tightened to form an airtight, fluid-tight seal therebetween. A second set of threads 120W are provided on the top portion of the adapter 120 and mate with the threads 128T of the nut 128, which are tightened to physically hold the flange of the nipple 70. The under surface of the shoulder 128H compresses the flange 70F between it and the top surface of the adapter 120 to form the seal as the threads are tightened. The threads and size of the adapter 120 and nut 128) can be manufactured in various sizes and specifications for use in adapting to a variety of bottle and nipple manufacturing standards.

FIG. 24 is an illustration of the system 100 installed on the breast 2 around the nipple 3 and supported by a bra 130 in which the system 100 is received. The flexible container 60 conforms to the curvature of the bra 130 so that the wearing of the system 100 is very discreet. Also because of the flexibility of the container 60 and the positive pumping action of the system 100, the container 60 can be in a collapsed condition prior to filling it, so that it takes up virtually no space within the bra 130. Thus, only the contour of the main body 34 of the system 100 adds any bulk to the appearance of the breast. As the container 60 beings to fill with milk, the breast 2 reduces in size by an equivalent volume of the milk expressed and therefore the outward appearance of the components supported by the bra does not significantly change.

Figure 25:
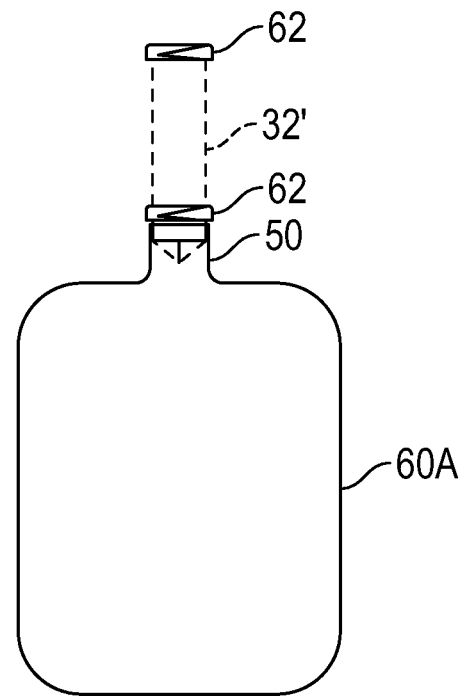
FIG. 25 illustrates a milk collection container according to another embodiment of the present disclosure.
Figure 26:
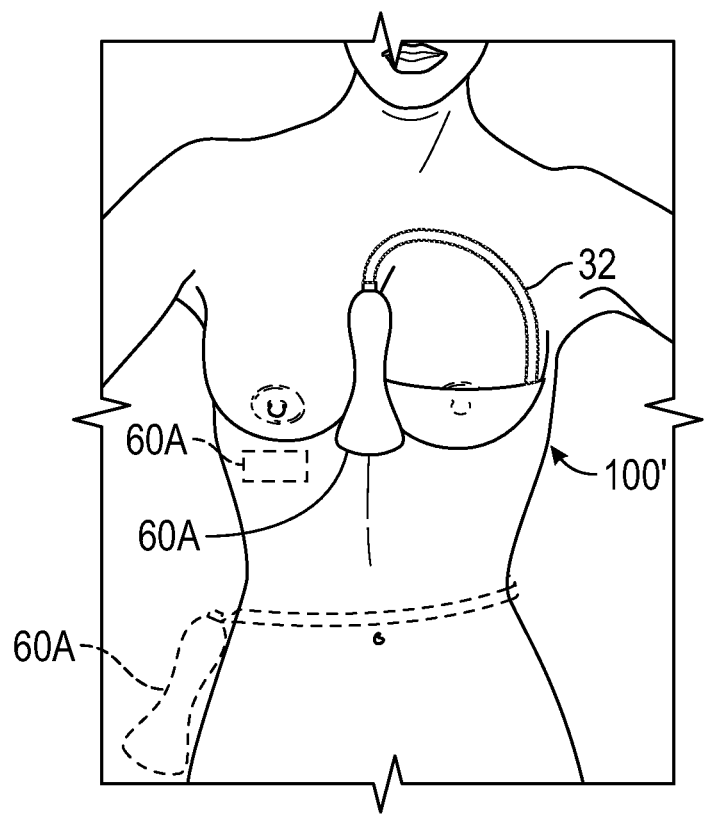
FIG. 26 illustrates alternative locations for placement of a container, according to various embodiment of the present disclosure.

The milk collection container 60 does not necessarily need to be hemispherically shaped as described above, but could alternatively be formed to have a different shape. Further, an array of differently size and/or shaped containers may be provided to accommodate different storage needs (containers have relatively more capacity for breast that produce and express relatively more milk), placement (different size or shape for placement between the breasts), etc. FIG. 25 illustrates a milk collection container 60a according to an embodiment of the present disclosure. Collection container 60a can be made from any of the same materials described above for making collection container 60. In this embodiment, milk collection container 60a is shaped like a conventional blood collection bag such as the type used by the red cross for blood donations, but is equipped with a one-way valve 50 and extension 62 in the same manner as container 60. Because of the positive pumping pressure capability of the system 100' (same as 100, but used with container 60'), the container can be placed between the breasts as shown in FIG. 26 and connected to tube 32 either at the top or the bottom (or any other location) of the container 60a. Also shown in FIG. 26 are alternative locations where the container 60a could be carried by the user. These include, but are not limited to: adhered to the torso just below the breasts, or carried in a holster that is attached by a belt around the waist of the user, or clipped to a belt around the waist of the user. Alternatively, container 60a could be carried in a pocket of a blouse, sweater or jacket worn by the user. Further alternatively, container 60a can be supported by a table or other external structure if the user is to remain stationary during an extraction process. Optionally, container 60a may have an extension tube 32', which may have the same properties as tube 32 and include an extension 62 with connection mechanism for connecting to the tube 32 of the system 100'. The extension tube 32' can be particularly useful for placement of the container 60a away from the location of the breasts.

Figure 27A:
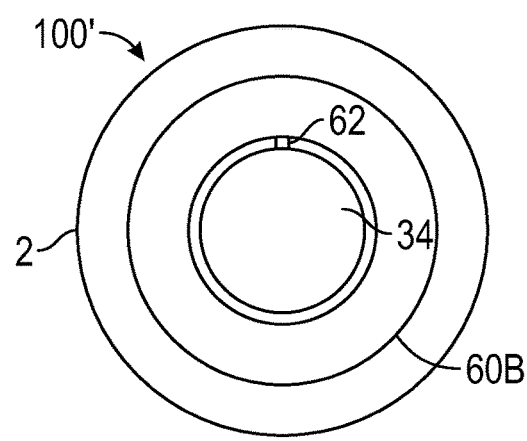
FIG. 27A illustrates a breast pump system using a doughnut-shaped collection container according to an embodiment of the present disclosure.
Figure 27B:
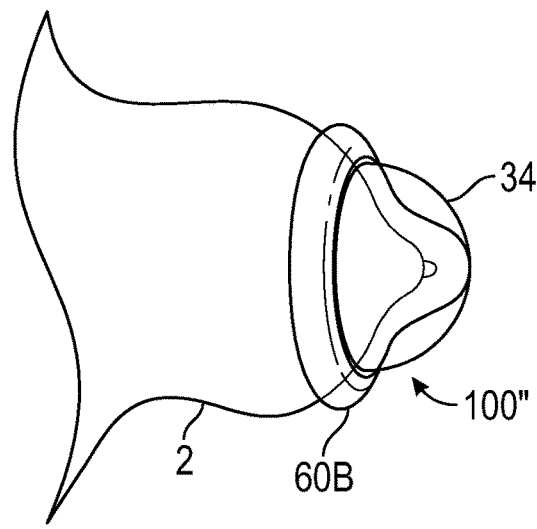
FIG. 27B is a side view of the system of FIG. 27A shown mounted on a breast.

FIG. 27A illustrates system 100" which is the same as system 100 except for the use of doughnut-shaped collection container 60b. Collection container 60b can be made from any of the same materials described above for making collection container 60. Collection container 60b fits on top of the breast 2 and surrounds the main body 34 of system 100". In this way, the profile of the system 100' extends away from the body of the wearer less than system 100, as container 60b does not overlie main body 34, as is readily apparent from the side view of FIG. 27B. Alternatively, instead of forming a complete ring, the doughnut-shaped container 60b could extend only over a predefined arc, such as in the range of from about 180 degrees to 355 degrees. In this embodiment, the volume gain in the container 60b arising from collection of milk will equal the loss in volume of the breast having that volume of milk extracted, resulting in no change in the volume contained within the bra 130 of the user, so that there is no noticeable difference in the appearance of the user before and after collection of milk in the container 60.

Figure 28A:
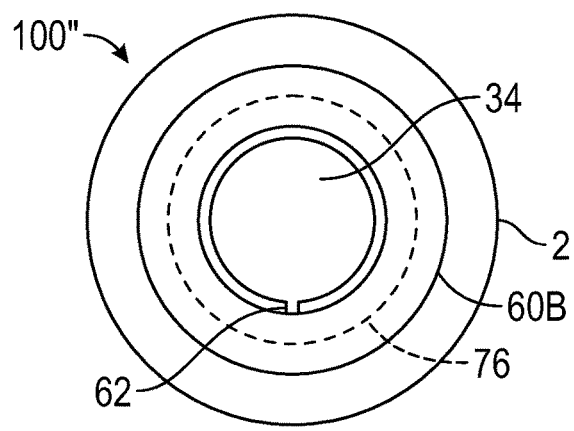
FIG. 28A illustrates a doughnut-shaped container having baffles intermediate of the inner and outer surfaces of the doughnut shape, according to an embodiment of the present disclosure.
Figure 28B:
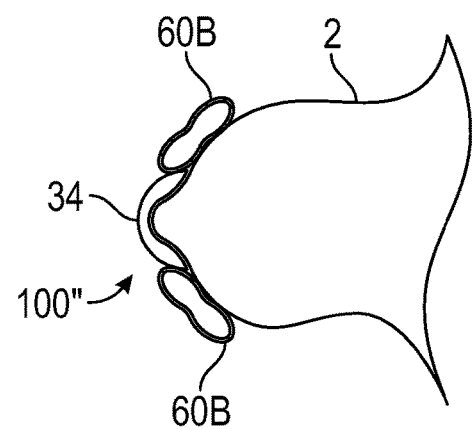
FIG. 28B is a side view of FIG. 28A, showing a cross-sectional view of the container.
Figure 28C:
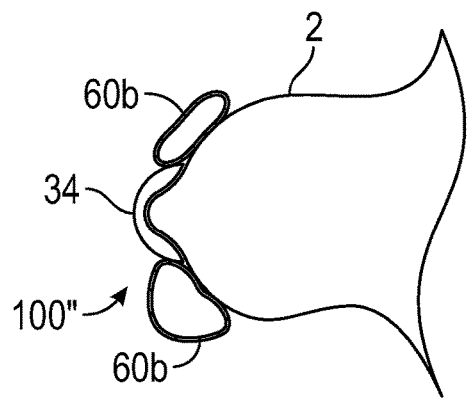
FIG. 28C illustrates a view with a container that does not have baffles, containing the same volume of milk as the container with baffles in FIG. 28B.

Any of the collection containers described herein may optionally include one or more baffles or other constrictions to facilitate a more even fluid distribution to avoid unsightly bulges on the wearer that might otherwise occur in a collection container not having such restrictions, where the milk all accumulates at the lowest portion of the container due to gravity. FIG. 28A illustrates a doughnut-shaped container 60*b* having baffles 76 intermediate of the inner and outer surfaces of the doughnut shape. Note that container 60*b* is connected to tubing 34 via extension 62 at the lower portion of the container 60*b* in this instance. This is unrelated to the inclusion of baffles 76, but is shown as one of the alternative locations that a container can be attached to the tube 34. Baffles 76 are locations in the container 60*b*, where the opposing layers of the container are fused or glued together to restrict the container 60*b* from expanding as much as it otherwise would. Various shapes like pie wedges, waffles, etc. can be formed by the baffles 76. Further, shapes that take into the contour/three-dimensional geometry of the main body 34 that the container 60 will conform to can be provided. Optionally, an additional layer of polymer 61 can be provided on top of the baffles 76 to help smooth out the external surface of the container 60 to improve the aesthetics of the container when worn, by smoothing out the exterior surface. FIG. 28B is a side view of FIG. 28A, showing a cross-sectional view of the container 60*b*. FIG. 28C illustrates a view with a container 60*b* that does not have baffles, containing the same volume of milk as the container 60*b* with baffles 76 in FIG. 28B. On comparison, it can be readily observed that most if not all of the milk has accumulated in the lower portion of the container 60*b* in FIG. 28C, resulting in a bulging appearance under the clothing of the wearer. In contrast, the milk is more evenly distributed in FIG. 28B and does not present an asymmetrical, unsightly bulge.

Figure 28D:
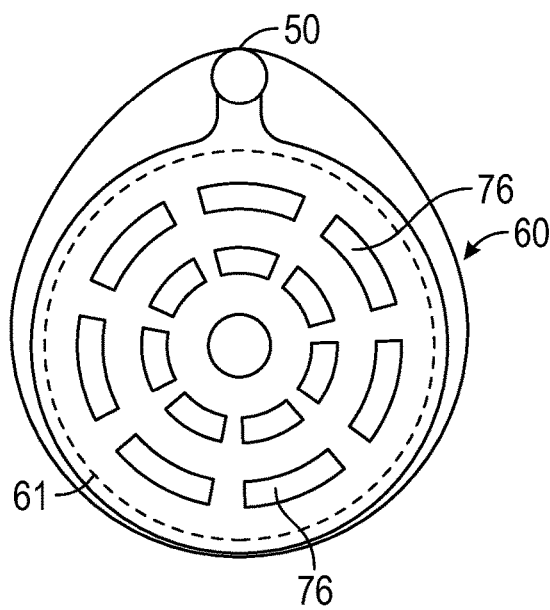
FIG. 28D is an illustration of a container showing baffles arranged in a waffle pattern to control the even distribution of the volume of milk as it is received, according to an embodiment of the present disclosure.
Figure 28E:
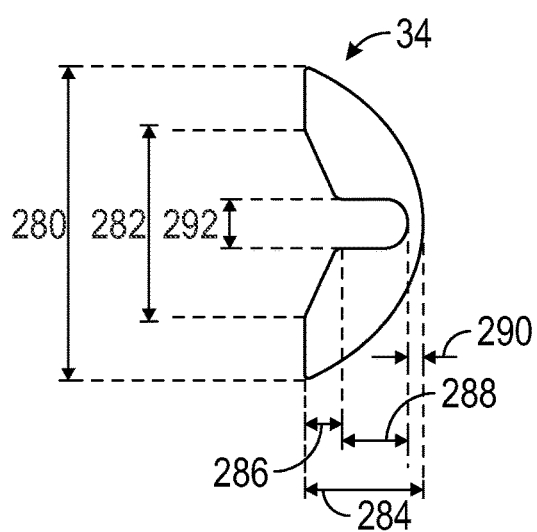
FIG. 28E is a side view of a main body to illustrate the dimensions of the main body, according to an embodiment of the present disclosure.
Figure 28F:
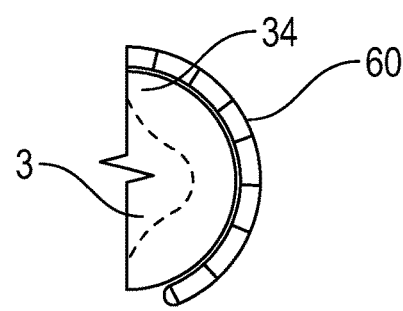
FIG. 28F is an illustration of the container of FIG. 28D mounted on the main body of FIG. 28E, according to an embodiment of the present disclosure.

FIG. 28D is an illustration of a container 60 showing baffles 76 arranged in a waffle pattern to control the even distribution of the volume of milk as it is received. FIG. 28E is a side view of a main body 34 to illustrate the dimensions of the main body 34, according to an embodiment of the present disclosure. In this embodiment, the overall distance 280 from top to bottom of the main body 34 measures about 9 cm. The distance 282 from where the main body 34 begins to taper inwardly to follow the contours of the breast 2 to the end of the taper at the bottom portion of the main body 34 measures about 7 cm. The dimension of the portion that is configured to receive the nipple 3 measures about 2 cm in diameter. The overall length 284 of the main body 34 measures about 4.5 cm. The distance 286 between the proximal most surface of the main body 34 and the proximal bend end of the nipple receiving cavity is about 1 cm. The length 284 of the nipple receiving cavity is about 3 cm and the main body 34 extends distally from the distal end of the nipple receiving cavity by a distance 290 of about 0.5 cm. It is noted that the foregoing dimensions are exemplary only and that any and all of these dimensions may be varied for other embodiments. FIG. 28F is an illustration of the container 60 of FIG. 28D mounted on the main body 34 of FIG. 28E. Also shown in phantom lines is a nipple 3 received in the nipple receiving cavity of the main body 34.

As noted, in order to control shape of the container and/or volume distribution of milk, container 60 may have various baffles/waffles 76. The size and/or shape of the waffles 76 will help the container 60 conform to a curved surface. Baffles/waffles 76 can also control height or protrusion of the container locally. For example, it may be beneficial to the allow the container 60 to swell more on the top of the main body 34, in which case, less dense waffle baffling 76 will be provided at the upper portion of the container 60 as compared to that provided at the lower portion of the container 60. The bottom of the container, provided with more dense waffling 76, will minimize the swell height in the bottom portion of the container, resulting in more aesthetic, discrete changes in breast shape contour while pumping.

The container 60 can be larger than the pump housing (main body) 34, allowing a portion of the container to contact the skin of the breast 2. Also, the container 60 can be contained within the housing 34, about or adjacent pumping structure, or the container can be positioned between the pumping structure or housing and the user's breast. Further alternatively, container 60 can dual shape, cavities or compartments. Part of the container 60 may lie on top of the main body and allow collection of only a predetermined volume of milk, such as 4 oz. or some other predetermined volume. The remaining portion of the container 60 may hang below the breast 2 or to the side. This allows distribution of the milk volume to aid in discretion/aesthetics—as well as weight distribution. By keeping the extra milk volume next to the skin—there is less moment arm/weight of milk further out from the woman's chest. This can facilitate stability of the attachment of the system 100 to the breast 2 and comfort.

Alternatively, the breast pump system may allow multiple ways to collect the milk. For example, if desired for comfort or aesthetic reasons, when a user expects to express greater than 5 oz milk per breast, the system 100 may allow replacement of the on pump container 60 with tubing that attaches at the same point and transfers milk to a "remote" collection vessel, such as a remote collection container worn at the waist or in a purse/bag held over the shoulder or left on a desk.

FIG. 29A illustrates a container 60*c* used with system 100′″ that fits around the main body 34 of the system and the areola of the breast 2. In this instance, container 60*c* is connected to tube 34 at the bottom of the main body and one-way valve 50 is provided on the inside surface of the annular container. FIG. 29B illustrates a variant of container 60*c* in which the one way valve 50 is located on the outside of the annular container. Baffles 76 are formed in the container 60*c* to help evenly distribute the milk, but also to facilitate folding of the container. FIG. 29C shows the one way valve and connecting portion of the container 60*c* having been folded upwardly along a baffle 76 line to join the one-way valve 50 to the tube 32 of system 100′″. After collecting milk in the container 6*c* and detaching it from the system 100′″, the container 60*c* can be tri-folded along the other baffle 76 lines as shown in FIG. 29D, for more compact storage, such as in the refrigerator or freezer.

Figure 30:
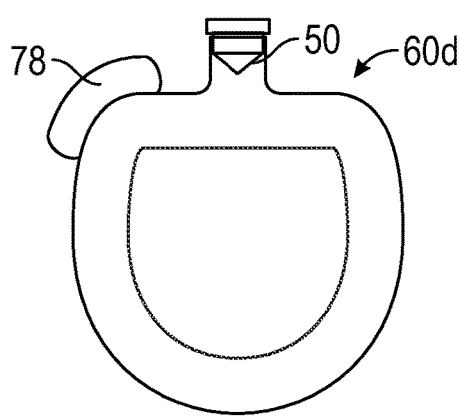
FIG. 30 shows a milk collection container that is ring-shaped to encircle the breast, according to an embodiment of the present disclosure.

FIG. 30 shows another embodiment of a milk collection container 60*d* that is ring-shaped to encircle the breast 2 and which includes one-way valve 50. Additionally container 60*d* is provided with a tab or flap 78 that extends from the milk containing portion of the container 60*d* and that is not configured to contain any milk. Because the flap/tab 78 is separated from the milk volume containing portion, it can be written on or otherwise annotated without the potential of puncturing the milk-containing portion or otherwise contaminating the contained milk. This tab/flap 78 feature can be provided on any of the embodiments of milk collection container described herein.

Figure 31A:
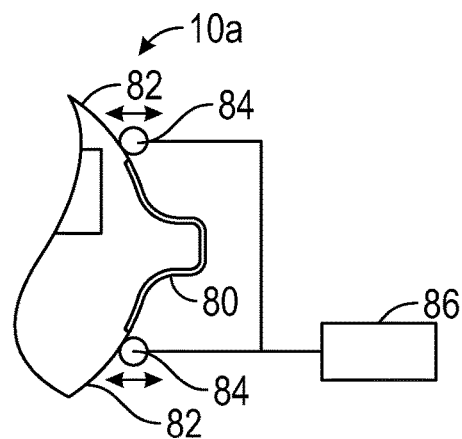
FIG. 31A shows a breast adapter that includes a rigid portion where the nipple is inserted, and a flexible, resilient portion, according to an embodiment of the present disclosure.
Figure 31B:
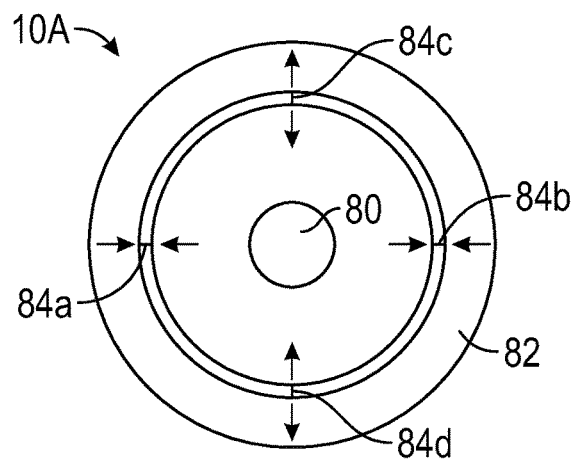
FIG. 31B illustrates four different locations where the breast can be alternatively compressed and allowed to expand by using four massage drivers, according to an embodiment of the present disclosure.

Various modifications and embodiments of the breast adapter 10 can be employed in system 100 to enhance milk drawdown and extraction, improve comfort of fit, and provide other advantages. FIG. 31A shows a breast adapter that includes a rigid portion 80 where the nipple is inserted, and a flexible, resilient portion 82. Massage drivers 84 such as rollers that are driven by motor 86 to advance and retract the rollers 84 against the breast to massage it, or other mechanical equivalent, such as pumps, motor-driven lever arms or the like can provide mechanical massaging of the breast to simulate actions of a suckling baby and potentially improve milk extraction. Massage drivers 84 can be provided in more than one plane to deform the breast along more than one direction. FIG. 31B illustrates four different locations 86*a*, 86*b*, 86*c*, 86*d* where the breast 2 can be alternatively compressed and allowed to expand by using four massage drivers. These massage drivers can be actuated in many different patterns so as to effect different massage actions. More or fewer than two or four massage drivers 84 can be implemented to design various different patterns of massage.

Figure 32A:
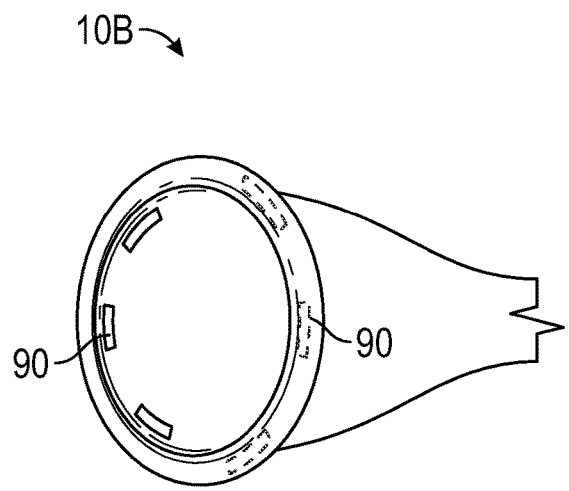
FIG. 32A illustrates a breast adapter provided with vibration drivers according to an embodiment of the present disclosure.

FIG. 32A illustrates an embodiment in which the breast adapter 10B is provided with vibration drivers 90. Vibration drivers 90 may be in the form of piezoelectric transducers that can be electrically driven by battery 48 at a desired frequency to apply vibration to the breast 2, which may help to stimulate milk letdown and/or extraction. Frequencies of vibration applied may be in the range of 100 Hz to 30 kHZ, typically about 250 Hz.

Vibration drivers 90 may be employed on any of the breast adapter embodiments described herein. Alternatively, massage drivers 84 may be modified so at to apply vibrational frequency to the breast 2. Further alternatively, vibration drivers may be provided on a different element of the system 100 or on an additional element separate of the system 100, as opposed to providing them on the breast adapter 10. Although six vibration drivers 90 are shown in FIG. 32, more or fewer could alternatively be used (as few as one). Application of vibration to the breast 2 by vibration drivers 90 may be applied to stimulate milk down, by application of vibration for ninety second or less, for example. Additionally, the vibration applied to the breast may enhance milk flow volume and/or rate during extraction, by stimulating hormonal release and/or by the physical agitation of the breast. Vibration may also help prevent ducts in the breast from becoming clogged. Vibration can help with flow and may help prevent clogged ducts. It may also be helpful in unclogging ducts and/or increasing milk flow over that which would have been achieved without application of vibration. Vibration can also be applied to break up/facilitate flow. Various frequencies may be activated for different modes applied to achieve different ones (or combinations of) these effects. Relatively slower vibrational frequencies may be more attuned to bulk mechanical movement, while higher frequencies may actually hit resonant frequencies with smaller structures like the milk ducts. Different structures within the breast can be targeted based on frequency and amplitude of the vibrational forces applied.

Figure 32B:
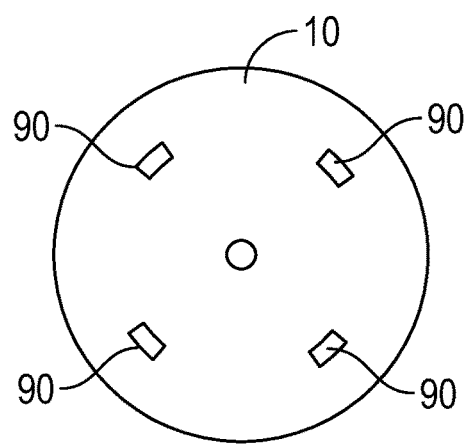
FIG. 32B is a rear view (open end) of breast adapter showing vibration drivers such as motors or piezoelectric devices mounted on the breast adapter, according to an embodiment of the present disclosure.
Figure 32C:
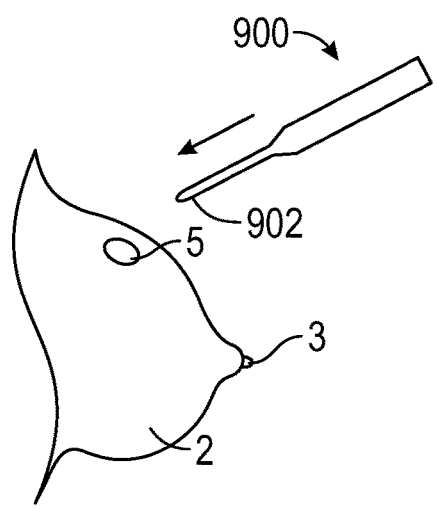
FIG. 32C illustrates a handheld vibration driver that is operable independently of a breast pump system, according to an embodiment of the present disclosure.

FIG. 32B is a rear view (open end) of breast adapter 10 showing vibration drivers 90 such as motors or piezoelectric devices mounted on the breast adapter 10. One or more of the vibration drivers 90 can be activated at any one time, so that a pattern of activation can be run so that drivers 90 apply vibration or massaging at different times in a sequence to carry out a squeezing or massaging motion. Additionally, power and/or frequency applied to each driver 90 can be changed as desired. FIG. 32C illustrates a handheld vibration driver 900 that is operable independently of system 100. In the embodiment shown, handheld driver 900 is a pen or other elongated implement that is configured with one or more motors or piezoelectric vibrators. Optionally, different attachments can be provided to vary the contact surface and/or shape of the distal end 902 of the implement 900 used to contact a target location 5 of the breast 2 to be vibrated or massaged. Like the embodiment of FIG. 32B, the frequency and/or power applied by implement 900 can be changed as desired by the user.

Figure 33:
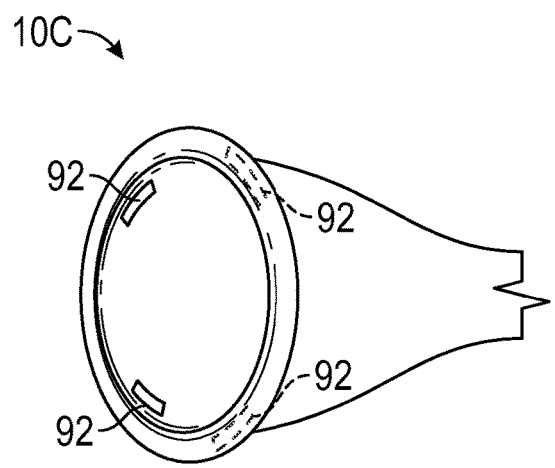
FIG. 33 illustrates a breast adapter provided with heating elements according to an embodiment of the present disclosure.

FIG. 33 illustrates an embodiment in which the breast adapter 10C is provided with heating elements 92. Heating elements 92 may be in the form of electrically resistive coils, or elements, piezoelectric transducers, or other alternative elements that can be electrically driven by battery 48 to generate heat. The heat generated is applied to the breast 2, which may help to stimulate milk letdown and/or extraction. Heating elements 92 may be employed on any of the breast adapter embodiments described herein. Heating elements 92 may be used in combination with vibration drivers 90. Although four heating elements 92 are shown in FIG. 33, more or fewer could alternatively be used (as few as one). Heating has been demonstrated in clinical studies to increase flow and speed of expression. Therefore heating elements 92 may apply heat to the breast to benefit flow increase, less clogging, less mastitis rates, etc.

Figure 34:
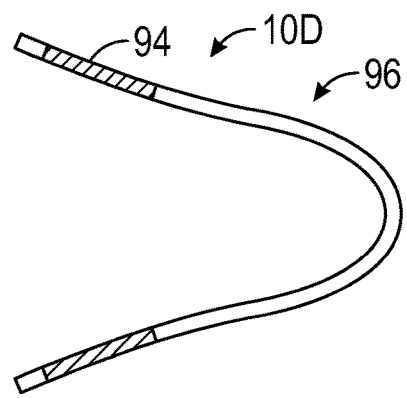
FIG. 34 schematically illustrates a breast adapter having a suction zone which is flexible and forms a seal with the breast when suction is applied, while a rigid portion receives the nipple and areola of the breast, according to an embodiment of the present disclosure.
Figure 35A:
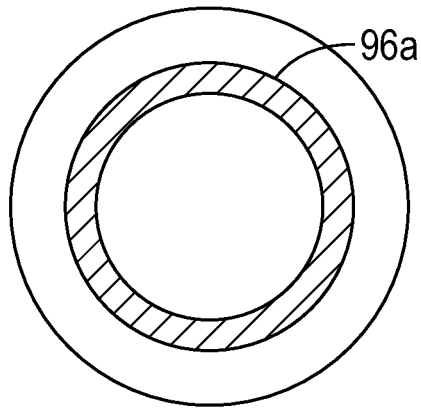
FIGS. 35A and 35B are back end, schematic illustrations of a breast adapter showing that the suction zone can be applied in a continuous ring or intermittently, according to various embodiments of the present disclosure.
Figure 35B:
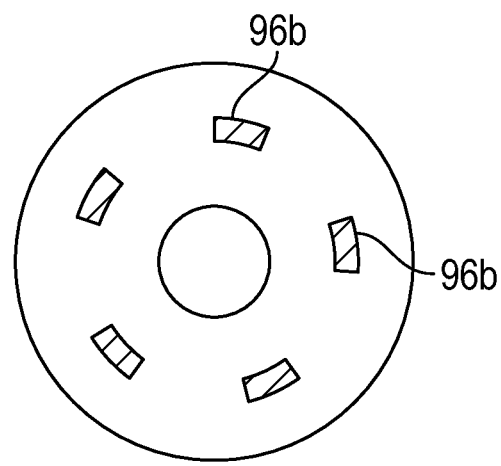

The application of suction/vacuum to the breast 2 by breast adapter 10 may be varied. FIG. 34 schematically illustrates a breast adapter 10D having a suction zone 94 which is flexible and forms a seal with the breast 2 when suction is applied, while a rigid portion 96 receives the nipple and areola of the breast. FIGS. 35A and 35B are back end, schematic illustrations of breast adapter 10D to show that the suction zone 94 can be applied in a continuous ring 96*a* or intermittently 96*b*. Suction to breast 2 provides more positive/additional security for attachment and sealing against the breast 2. The embodiments of FIGS. 34 and 35A show rings of suction which can also function to form a seal against the breast 2. The embodiment of FIG. 35B targets suction forces against the breast 2 to ensure attachment to breast 2 so the system 100 doesn't break away and fall off, as it relies on the pumping mechanism suction cycle to maintain the seal. By intermittently applying the suction (as opposed to a continuous ring of suction), the smaller combined area where the suction is applied requires less suction/power to be generated by the suction source to maintain the attachment.

Figure 36:
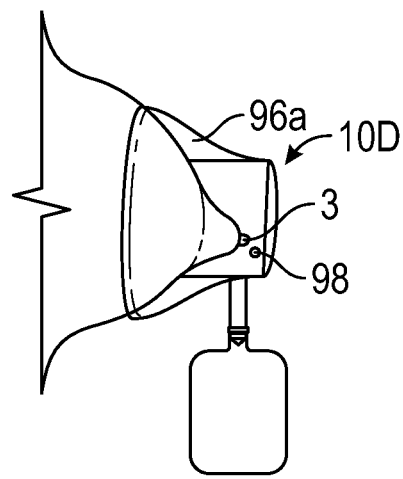
FIG. 36 schematically illustrates an arrangement in which a first, relatively lower suction/vacuum level is constantly applied by a breast adapter though a suction zone to maintain a seal with the breast, according to an embodiment of the present disclosure.

FIG. 36 schematically illustrates an arrangement in which a first, relatively lower suction/vacuum level is constantly applied by breast adapter 10D though suction zone 96*a* to maintain a seal with the breast. A second, larger suction/vacuum level is intermittently applied to the space 98 surrounding the nipple 3 for extraction of milk.

Figure 37A:
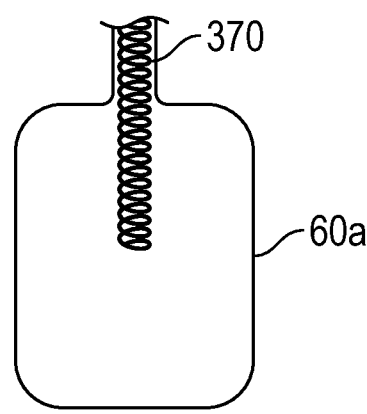
FIG. 37A illustrates a flexible spring provided in a container to maintain an open channel within the container, according to an embodiment of the present disclosure.
Figure 37B:
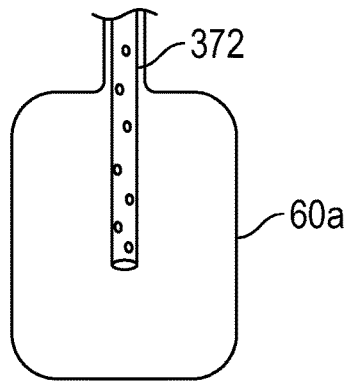
FIG. 37B illustrates a flexible porous tube provided in a container to maintain an open channel within the container, according to an embodiment of the present disclosure.

FIGS. 37A-37B illustrate features that may be provided in a milk collection container 60 to reduce the risk of the container not opening to receive milk due to the sides of the container sticking together, static, or some other obstructive force. In FIG. 37A, a flexible spring 370 is provided in container 60*a*, which keeps an open channel within the container and does not obstruct the flow, due to the loosely wound coils of the spring, and which allows the container 60*a* to remain flexible, as the spring 370 is flexible. In FIG. 37B, a flexible porous tube 372 provides similar functions to spring 37. Although elements 370 and 372 are shown in use in container 60*a*, it is noted that they can be equally as well used in any of the other embodiments of milk collection container described herein.

Figure 38:
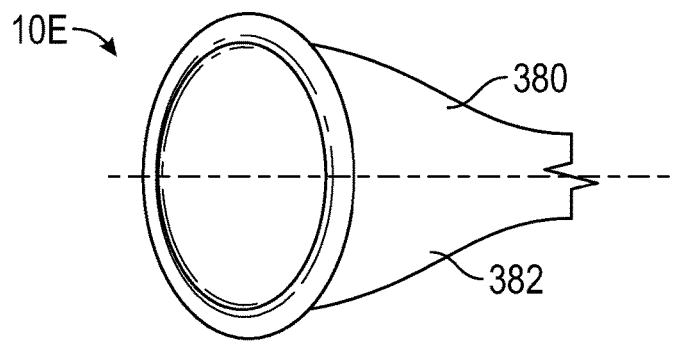
FIG. 38 shows a breast adapter in which the upper half (or other upper portion) of the adapter has different mechanical properties and/or composition than the lower half (or other lower portion) of the breast adapter, according to an embodiment of the present disclosure.

FIG. 38 illustrates another embodiment of breast adapter 10E in which the upper half (or other upper portion) 380 of the adapter 10E has different mechanical properties and/or composition than the lower half (or other lower portion) 382 of the breast adapter 10E. In the embodiment shown, portion 382 is flexible and portion 382 is rigid, or has less flexibility that portion 380. When used in combination with massage drivers 84, the breast 2 will be massaged at the bottom portion thereof, but not as much, or not at all along the top portion.

Figure 39A:
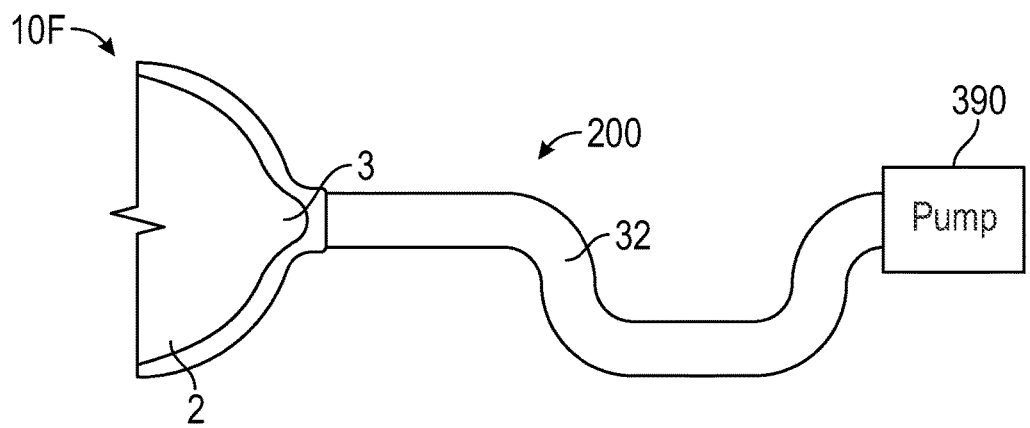
FIG. 39A illustrates a system employing a flexible breast adapter connected to a tube which is supplied by suction/vacuum by a pump, according to an embodiment of the present disclosure.
Figure 39B:
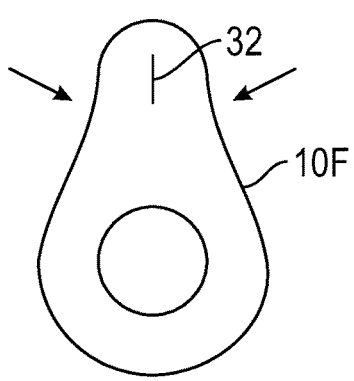
FIGS. 39B-39C illustrate that application of squeezing action by the breast adapter to squeeze the breast causes the tube to temporarily collapse (see FIG. 39B) which causes a pressure change at the nipple, and, upon release of the compression forces against the breast, the tube reopens (see FIG. 39C), according to an embodiment of the present disclosure.
Figure 39C:
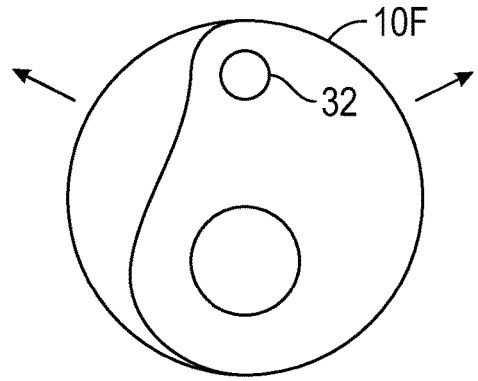

FIG. 39A illustrates a system employing a flexible breast adapter 10F connected to tube 32, which is supplied by suction/vacuum by pump 390. The application of squeezing action by adapter 10F to squeeze the breast 2 (whether by massage drivers 84 or other compression means) causes tube 32 to temporarily collapse (see FIG. 39B) which causes a pressure change at the nipple 3. Upon release of the compression forces against the breast 2, the tube 32 reopens (see FIG. 39C) and milk is extracted into the tube 32.

Figure 40:
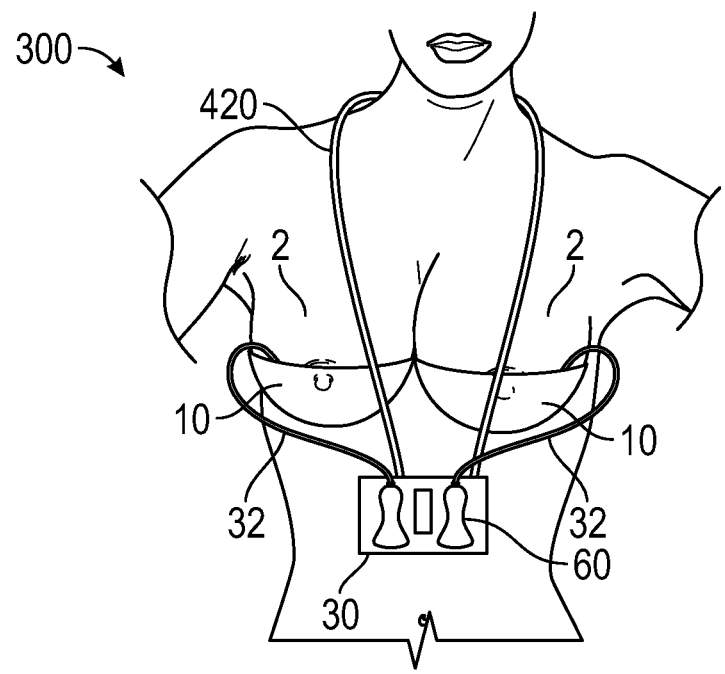
FIG. 40 illustrates a breast pump system in which the pumping region 30 and container are suspended on a lanyard worn by the user, according to an embodiment of the present disclosure.

FIG. 40 illustrates a breast pump system 300 in which the pumping region 30 and container 60 are suspended on a lanyard 420 worn by the user. The length of the lanyard 420 is adjustable, so that the user can position the pumping region 30 and container 60 lower or higher than shown, to a location that is comfortable to the user. Tubes 32 interconnect the pumping mechanism 30 with breast adapters 10, which may be provided on both breasts 2 as shown, or, alternatively, only on one breast 2.

Figure 41:
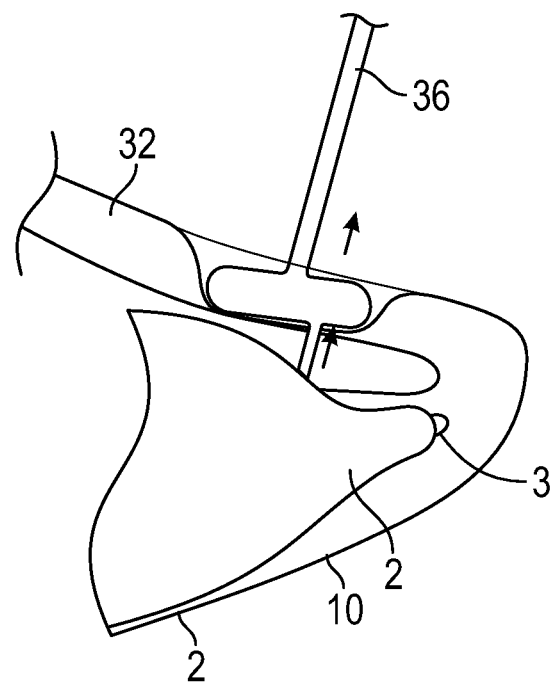
FIG. 41 illustrates an embodiment in which, in addition to the suction/vacuum created by withdrawing a compression element away from the tube, the compression element is also mechanically linked to a portion of the breast adapter surrounding the nipple, according to an embodiment of the present disclosure.

FIG. 41 illustrates an embodiment in which, in addition to the suction/vacuum created by withdrawing compression element 36 away from tubing 32T the compression element 36 is also mechanically linked to a portion of breast adapter 10 surrounding the nipple 3. Thus, as element 36 moves away from tube 32, it also pulls on that portion of breast adapter 10, causing it to open wider and create a greater suction/vacuum around the nipple 3. As the compression element 36 compresses the tubing 32, as shown in FIG. 41, it also mechanically moves the wall of the breast adapter 10 to reduce its cross-sectional dimension.

Referring back to FIG. 2, the pressure sensor signals received by controller 52 from pressure sensor 54 can be used to plot pressure/suction (vacuum) waveforms applied by the system 100 during operation. Additionally, pressure sensor 54 signals can be used to determine when milk flow initiates, as well as the rate and/or volume of milk flow based on pressure changes resulting from milk being present in the adapter 10 and/or tube 32. Since milk is incompressible, and neglecting any losses associated with air leaks, and also assuming a majority of air has been purged from the system 100, the wall of the tube 32 as it rebounds to regain the unbiased configuration (in the absence of any milk inflow) creates a peak suction $P(p)$ when released from the compressor element 36/38. In this state the tube 32 is deformed to have less volume within it, referred to as volume $V(p)$. $P(p)$ and $V(p)$ will be maintained as a constant if there is no milk inflow. As milk inflows, the tube 32 begins to return to its natural shape. At each incremental amount of volume of milk introduced into the system 100, the suction force of the tube 32 reduces. The reduced suction level is referred to here as $P(n)$ and the volume associated with each increment is $V(n)$, where n equals a positive integer that starts at 1 and increases by 1 with each increment of milk received. Eventually the pressure reaches a final suction pressure $P(f)$ that corresponds to a final full volume of $V(f)$. Thus, via either a look-up table or by direct equation, each pressure detected can be converted to a volume. As a result, the amount of milk passed in one cycle of the system is equal to $V(f)$ minus $V(p)$ which is detectable by determining $P(f)$ and $P(p)$. When used in detecting letdown and initial expression of milk from the breast, upon detecting the initial expression, controller 52 can control compression elements 36, 38 to change from a mode used to initiate letdown and initial extraction (which may be performed by rapid cycling of compression element 36 alone, or a combination of rapid cycling of elements 36 and 38) to an extraction mode, such as by operating elements 36, 38 to maintain a maximum predetermined suction/vacuum (e.g., −180 mm HG, −200 mm Hg or −220 mm Hg). Upon sensing a predetermined amount of volume of milk having entered the system, the controller 54 can again change the mode of operation of elements 36, 38 to perform the expulsion phase, where element 36 seals off the breast adapter at a predetermined suction/vacuum level (e.g., −50 mm Hg or −60 mm Hg) and element 38 is operated to expulse the milk from region 42 under positive pressure. After the expulsion phase (when element 38 has completed its stroke), controller 54 again changes the mode of operation of elements 36, 38 to return to the extraction phase.

Cycle frequencies, amplitudes of pressure (suction/vacuum) can be controlled by controller 54 based on feedback from pressure sensor 52. These variables can be altered by the controller to optimize milk extraction, based on the estimations of milk flow and/or milk volume calculated from the pressure readings. Further, controller 52 can be programmed to end processing when milk flow senses had diminished to a predetermined flow rate, including, but not limited to a flow rate of zero, or alternatively, can be programmed to end processing at a predetermined time after a flow rate of zero has been reached. By continuing to apply suction/vacuum in an extraction phase for a predetermined time (e.g., thirty seconds, one minute, two minutes, or some other predetermined time) after flow rate has reached zero, this has the potential of stimulating the breast to increase milk production for subsequent feedings/milk extraction processes. Any of these automatic control schemes by the controller 52 can be overridden by the user, to choose different programming or operate the system 100 in manual mode via the use of controls 252.

Because the compression actuation elements 36, 38 are placed so close to the nipple 3, there is very little attenuation of the suction/vacuum waveforms generated thereby, relative to currently existing systems which typically place the suction/vacuum pump much further from the nipple. This provides an advantage in that pressure (suction/vacuum) waveforms, such as relatively high frequency changes in suction/vacuum can be applied, which would not be possible with prior art systems, as the attenuation would render them ineffective. For example, controller 52 can be programmed to mimic a feeding baby in one instance by emulating the baby performing three quick sips or suckles on the breast, followed by a longer duration suck, and then repeating this cycle. This would involve operating the compression elements 36, 38 to apply the maximum suction/vacuum (e.g., −200 mm Hg) to the breast 2/nipple 3 for a very short duration (e.g., half a second or less), followed by reducing the suction/vacuum to the minimum continuously applied suction/vacuum (e.g., −60 mm Hg), repeating this cycle two more times, then applying the maximum suction/vacuum for a more extended period (e.g., five seconds, tens seconds, fifteen seconds or more). After the extended period expires, the entire cycle could be repeated. This is only one example, as the controller 52 can be programmed to carry out any other variations of suction/vacuum cycling desired. For example, a mother could program the controller 52 to mimic the patterns of her baby when feeding, including programming the patterns of timing for pausing between sucks, how hard they suck (amount of suction/vacuum) and the frequency of sucking.

Pressure sensor 54 is preferably located in the breast adapter 10, preferably at a location near where the nipple 3 is received. Alternatively, the pressure sensor could be placed anywhere in juxtaposition with the suction/vacuum space. Further alternatively, in addition to the placement of the pressure sensor 54 in the breast adapter as illustrated in FIG. 2, one or more additional pressure sensors could be further included downstream of this location, including, but not limited to: distal of region 40, in between regions 40 and 42, proximal of region 42, but adjacent thereto, and/or distally adjacent one-way valve 50. In one embodiment, pressure sensor 54 is made as a "window" of the same material that surrounds it, so that it is sensitive to pressure changes and flexes inwardly or outwardly in response to pressure changes within the space that it is located.

Figure 43:
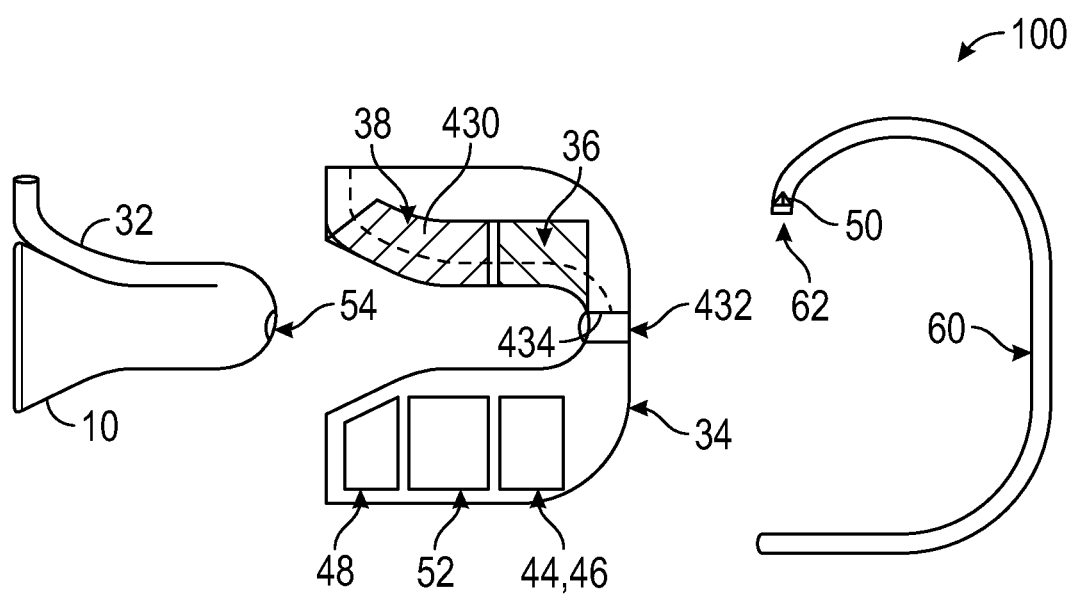
FIG. 43 is an exploded illustration of a breast pump system showing a pressure sensor placed at a proximal end portion of the breast adapter, according to an embodiment of the present disclosure.

FIG. 43 is an exploded illustration of system 100 according to another embodiment of the present disclosure, in which pressure sensor 54 is placed at the proximal end of the breast adapter 10 where the breast adapter 10 and tubing 32 are integrated and form the acute angle turn so that tubing 32 extends back distally along the contour of the breast adapter 10. An opening 432, which may optionally be closed off by a visibly transparent window 434, is provided in housing 34 and configured, dimensioned and positioned to be aligned with pressure sensor 54 upon insertion of the breast adapter 10/tubing 32 unit into the housing 34 in a manner as described previously. Opening 432 (and optionally window 434) allow optical sensing of the deviations in position of sensor 54 as the sensor 54 flexes in or out as a result of pressure change in the space within the breast adapter 10/tubing 32.

Figure 44A:
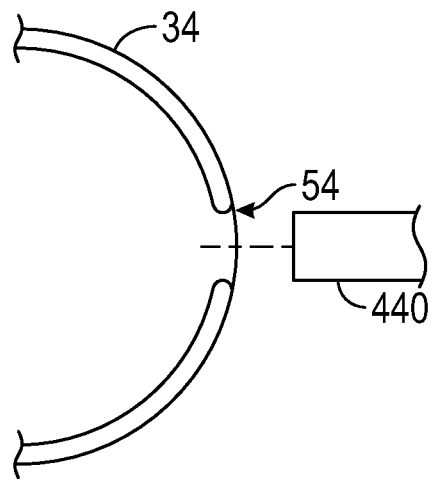
FIGS. 44A-44B illustrate operation of a pressure sensor to detect pressure within a breast pump system, according to an embodiment of the present disclosure.
Figure 44B:
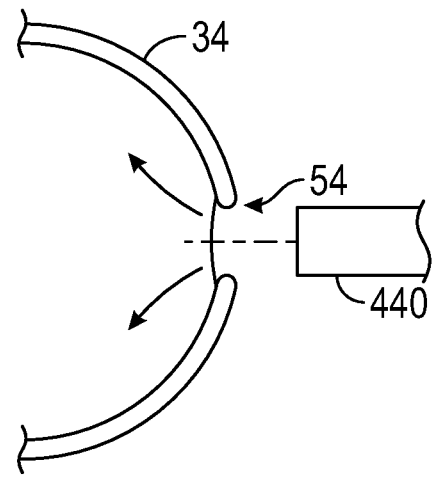
Figure 45A:
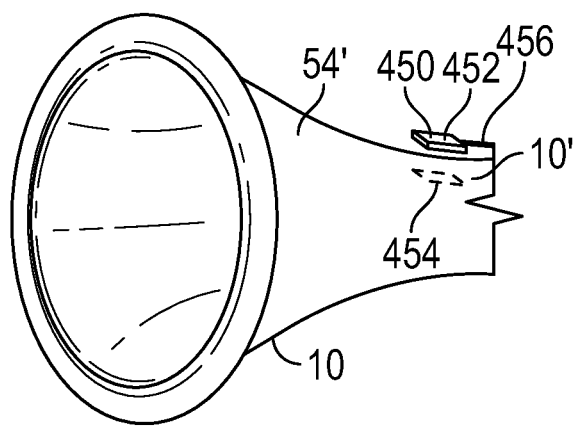
FIG. 45A illustrates a pressure sensor that can be used in a breast pump system according to another embodiment of the present disclosure.
Figure 45B:
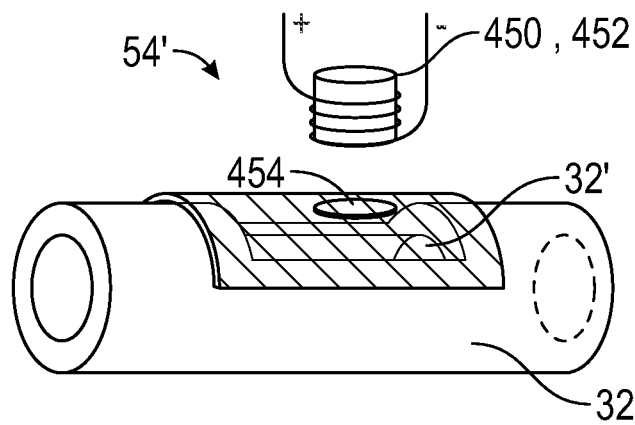
FIGS. 45B-45C illustrate additional views of the pressure sensor of FIG. 45A and its operation.

FIGS. 44A-44B illustrate operation of the pressure sensor 54 to detect pressure within the system. FIG. 44A shows pressure sensor 54 in an undeflected state at a known pressure. The pressure may be, for example, atmospheric pressure, or the minimum suction/vacuum level to be sustained (e.g., −60 mm Hg or −50 mm Hg or some other predetermined minimum suction/vacuum level), or some other known pressure. As suction/vacuum increases within the breast adapter 10, pressure sensor 54 flexes inwardly, as illustrated in FIG. 44B. The position/amount of deflection of the pressure sensor window 54 can be optically monitored by an optical monitor 440, which may include, but is not limited to: a light source, one or more fiber optic fibers, or the like. Alternatively, a metal/magnetic proximity sensor can be used, such as described with regard to FIGS. 45A-45C. The amount of window deflection of the sensor 54 correlates to the pressure (suction/vacuum) within the breast adapter 10. The controller 52 receives optical signals (or electric signals converted from the optical signals of optical monitor 400), calculates the amount of deflection of sensor 54 indicated by the signals, and calculates a pressure reading from the amount of deflection calculated.

Figure 45C:
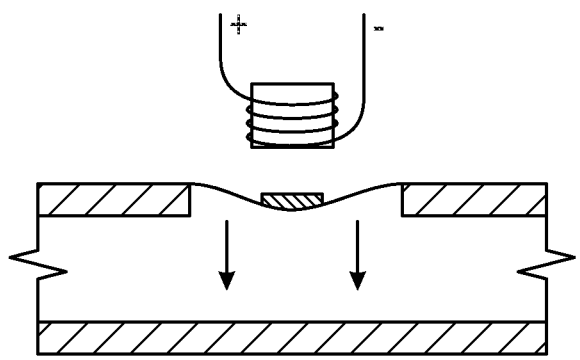

An alternative type of pressure sensor 54' that could be used is a Non-Contact DVRT®, available from Lord Microstrain Sensing Systems (Cary, North Carolina). This type of pressure sensor uses two coils 450, 452, one for sensing and the other for temperature compensation, see FIG. 45A. A metallic and/or magnetic target 454 is embedded in the material of the breast adapter 10, (or portion of tube 32, see FIGS. 45B-45C) in a region 10', 32' that is relatively more flexible than the portions of the breast adapter 10/tube 32 that surround the region 10', 32', respectively. The region 10', 32' may be in any of the locations described above with regard to sensor 54. The flexible region 10', 32' can formed as a part of the breast adapter 10/tube 32, such as by molding it to be thinner and more flexible than the surrounding areas. Alternatively, the flexible region 10', 32' can be grafted onto the breast adapter 10/tube 32, such as by forming a cutout region and then bonding (vulcanizing, or the like) a more flexible component over the cutout region. As the pressure in the breast adapter 10/tube 32 varies, the distance between the magnetic target 454 and the coils 450,452 varies, as illustrated in FIG. 45C due to the deflection of the flexible region 10', 32'. The coils 450, 452 sense displacement of the target 454. as the change in distance changes the field of inductance and results in a measurable change of either current or voltage. The change in voltage or current, is received as a signal from the sensor 54' by controller 52. The signal can be calibrated and correlated to changes in pressure within the breast adapter 10/tube 32. Signals representative of the pressure change are sent by sensor 54' to controller 52 via electrical line 456 (or, alternatively, wirelessly), where controller 52 can calculate displacement and pressure based on the signals received. Other alternative pressure sensors that could be employed include, but are not limited to: strain gauges, piezoelectric devices, or other pressure sensors currently available that can measure the pressure levels induced by the present system.

Figure 46:
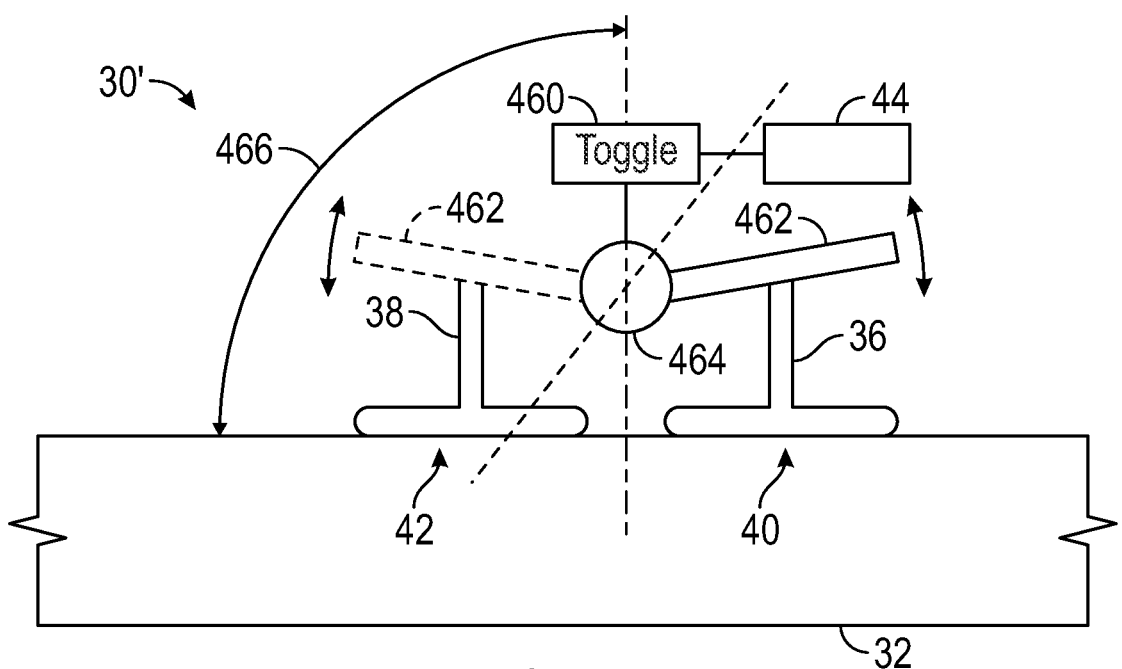
FIG. 46 is a schematic representation of a pump region that may be used in any of the breast pump systems described herein, according to another embodiment of the present disclosure.

FIG. 46 is a schematic representation of a pump region 30' that may be used in any of the breast pump systems described herein, according to another embodiment of the present disclosure. Pump region 30' uses only one servo motor (or a DC motor with gearing) 44 to actuate both compression elements 36, 38. Motor 44 is mechanically connected to a drive arm 462 that rotates to drive compression elements 36, 38 alternatively. In the initial actuation of motor 44 the drive arm 462 is swept via rotation about 464 (counter-clockwise in FIG. 46) to release compression element 36 to enable tube 32 to rebound, upon complete retraction, a toggle 462 is actuated, so that the next operation of motor 44 rotates the drive arm 46 in the opposite direction (clockwise in FIG. 46) to drive the compression element 36 to compress region 40 of tube 32. The toggle 460 is again actuated at the end of this operation and the next operation of motor 44 actuates the drive arm 460 to retract compression element 38 to create the high level suction/vacuum (e.g., −200 mm Hg) in the tube 32). The motor 44 controls the drive arm 460 to halt or reverse direction when the targeted high level suction/vacuum is reached. Additionally, the entrance and exit of the drive arm into and from the zone 466 actuates toggle 460 to cause the next motion of drive arm 464 to be in the opposite direction.

Figure 47:
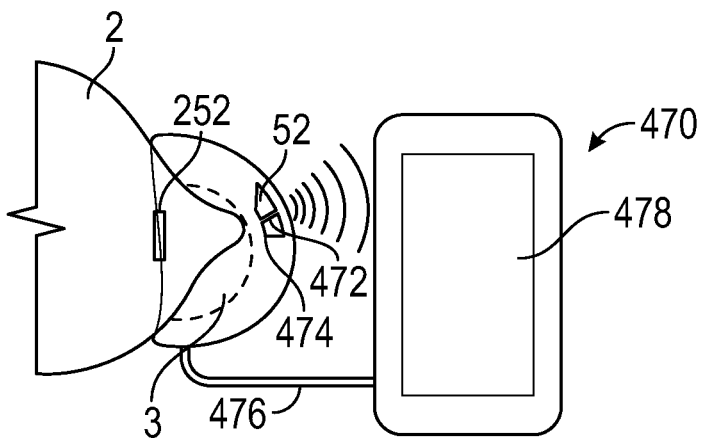
FIG. 47 is a schematic representation of transfer of data wirelessly from a controller of the system to a smartphone, according to an embodiment of the present disclosure.

The breast pump systems according to the present disclosure may optionally be designed with the capability of communicating to an external computer which may be, but is not limited to: a smartphone, a tablet computer, a laptop computer, a notebook computer or a server. FIG. 47 is a schematic representation (not to scale) of transfer of data wirelessly from controller 52 to smartphone 470. Controller 52 may include a wireless transmitter 472 that can be actuated by the user via controls 252 to send data to the external device 470 at will, as long as the external device 470 is in range of the transmitter 472. Alternatively, or additionally, a hard wire connection may be provided to send the data over the hard wire to the external device 470. Further alternatively, controller 52 can be provided with a BLUETOOTH® transmitter, so that data is automatically transmitted to the external device 470 whenever the external device 470 in in range of the BLUETOOTH® transmitter. Still further, controller 52 can be configured to automatically upload data to a server in the cloud and/or upload data to the cloud when instructed to do so by the user using controls 252. The uploaded data can then be used or shared in group studies of the data. Further, the external device 470 may be capable of downloading other customized programs for use with the breast pump system, which could be updated by crowd sourcing results from other mothers, etc. The uploaded data could also be useful for insurance companies or other entities having permission under the Affordable Care Act (and/or the user's permission) to use the data.

The external device 470 can be provided with software to customize pump functions based on data received from the controller 52, to calculate volume of milk extracted, to track expression efficiency and monitor it over time (within a single extraction session, as well as over multiple extraction sessions), keep track of inventory of previous expression sessions, dates of the sessions, and the specific containers 60 used in each individual session. This tracking can be useful for reminders to use the containers of milk 60 with a specified time, and can organize order in which the containers are to be used (e.g., first-in, first-out, or other scheme). Pump functions can be customized by varying suction levels, altering suction waveforms (amplitude and duration of application of suction), phases of extraction or feeding times, rest programming, heating temperatures and times, vibration frequency and duration, etc. Also the battery level can be monitored and a warning provided when the battery reaches a predetermined low level of charge. The external device may also use the display 478 to display one or more photos of the mother's baby during an extraction session to increase the emotional and physical reinforcement to simulate what is provided when the baby is actually feeding.

The extraction and expulsion phases of the cycle can be repeated continuously from the beginning to ending of a extraction session. Alternatively, controller 52 can be programmed to intermittently go through a rest phase during which all suction/vacuum is removed and the breast is exposed to atmospheric pressure. In the rest phase, the breast adapter 10 can be maintained sealed against the breast 2 by the support of the system 100 by bra 130 and, optionally, with an adhesive applied to the breast adapter 10 where it contacts the breast. The rest phase can be instituted to simulate the feeding baby "taking a break" from feeding, even though the feeding session has not yet ended. Additionally, such rest phases may help prevent edema, mastitis, or other problems that might occur without them. A rest phase can be commenced after a predetermined number of extraction and expulsion phases have been carried out or after a predetermined time of carrying out extraction and expulsion phases. The rest phase may be carried out for a predetermined time (a few seconds or more) after which suction/vacuum is re-established and the extraction and expulsion phases are again carried out. Further optionally, a rest phase may be commenced upon sensing via pressure sensor 54 that milk flow has fallen below a predetermined flow rate or has fallen to zero. The rest phase can also be initiated by user at the user's discretion, as various users may want to pump for relatively longer or shorter periods between rest phases.

Figure 48:
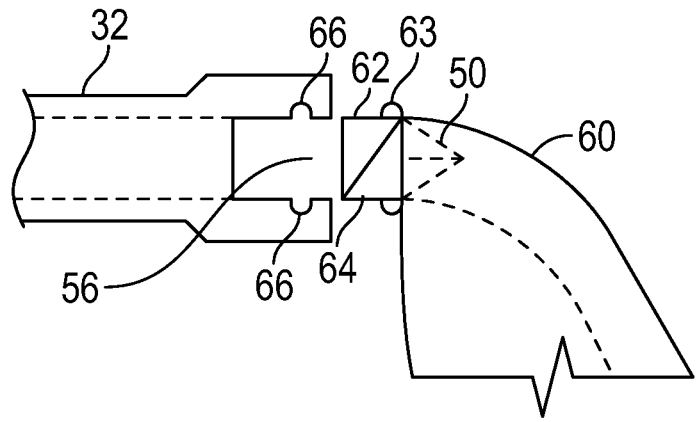
FIG. 48 illustrates configuration of the connection between the container and tube of the system for monitoring to ensure that the connection remains throughout an extraction and expulsion session, so that milk is not lost or wasted, according to an embodiment of the present disclosure.

The connection between the container 60 and tube 32 may be monitored to ensure that the connection remains throughout an extraction and expulsion session so that milk is not lost or wasted. One way of monitoring is to make components 66 and 63 metallic (see FIG. 48) or provide tube end 56 and connector 64 with other metallic contacts that are joined to make electrically contact when container 60 is properly connected to tube 32. The metallic connection is electrically connected to controller 52 which monitors the circuit to ensure that conductivity is maintained. If the container 60 should become dislodged or removed from the system such that conductivity is broken, the controller 52 immediately senses the disruption in conductivity and shuts down the pumping region 30.

Figure 49:
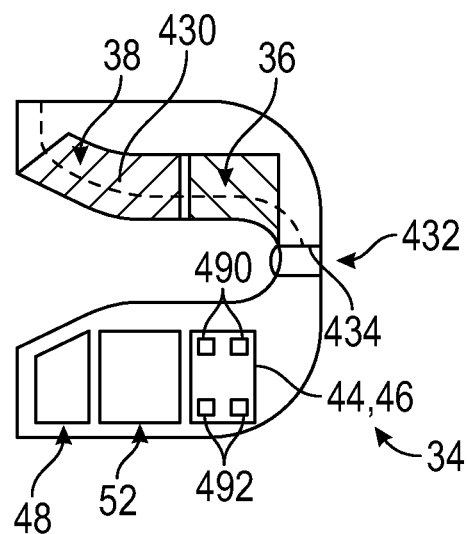
FIG. 49 illustrates that the motors of the system may be provided with heat sensors and/or motion sensors to provide feedback to the controller as to the operating temperatures of the motors and/or movement and/or rate of movement of the motors, according to an embodiment of the present disclosure.

Likewise, motors 44, 46 may be provided with heat sensor 490 and/or motion sensors 492 (e.g., tachometer or other motion sensor) to provide feedback to controller 52 as to the operating temperatures of the motors and/or movement and/or rate of movement of the motors, as illustrated in FIG. 49. This feedback can be used by the controller to shut down or slow down one or more motors if it overheats or fails to move properly when activation signals are applied.

Figure 50:
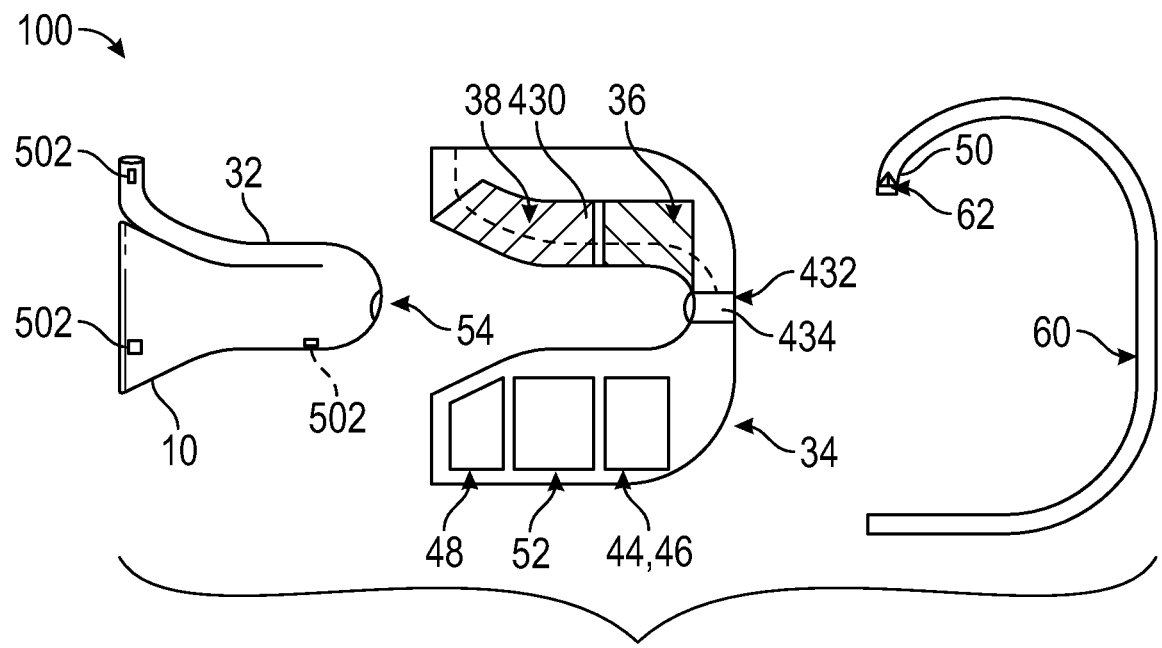
FIG. 50 illustrates a pressure relief member placed in the breast adapter, and also shows alternative, or additional locations for pressure relief members, according to an embodiment of the present disclosure.

A breast pump system according to the present disclosure may optionally be provided with a pressure relief mechanism to prevent generating too great a suction/vacuum within the system. FIG. 50 illustrates a pressure relief member 502 placed in the breast adapter 10, and also shows alternative, or additional locations for pressure relief members 502 in phantom. Pressure relief member 502 may comprises a pressure relief valve that automatically opens when a predetermined pressure that the valve is designed for is exceeded. For example, valve 502 may automatically open when the suction/vacuum pressure drops below −250 mm Hg or some other predetermined suction/vacuum level. Optionally, pressure relief member 502 may be in electrical communication with controller 52, such that controller 52 could automatically activate pressure relief member based on monitoring conditions indicating that the suction/vacuum is too great, or for rapidly initiating a rest phase, or is some other problem with the system is sensed. Still further, a user can control the controller 52 manually via controls 252 to manually initiate the pressure relief valve 52. A further alternative pressure relief member 52 is a lever arm or plunger than can be electrically activated by a coil to physically break the seal between the breast adapter 10 and the breast.

Figure 51:
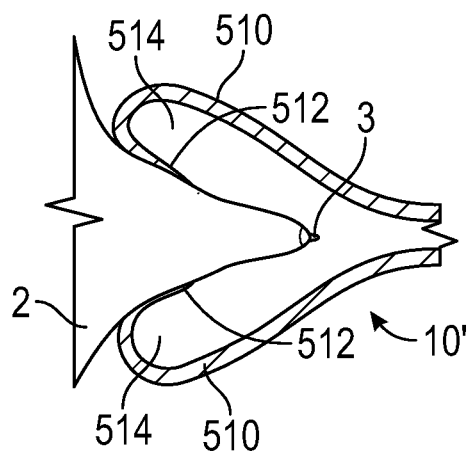
FIG. 51 shows a longitudinal sectional view of a breast adapter that may be used in any of the breast pump systems described herein, according to another embodiment of the present disclosure.

FIG. 51 shows a longitudinal sectional view of a breast adapter 10' that may be used in any of the breast pump systems described herein, according to another embodiment of the present disclosure. In addition to the primary flange 510 provided for receiving a portion of the breast 2 therein, adapter 10' includes a second flange 512 that loops or folds inwardly from the primary flange 510 and contacts the breast 2 when the breast is inserted into the system for carrying out an extraction session. Secondary flange 512 is designed to remain in contact with the breast 2 at all times during wearing of the system and preferably forms a seal with the breast. When the system has no suction/vacuum applied and up to a suction/vacuum level of the maximum suction/vacuum level applied during expulsion (e.g., 50 mm Hg or 60 mm Hg), a gap 514 exists between the secondary flange 514 and the primary flange 510. This is advantageous in that if the system should become disconnected from the breast 2 for any reason, any milk in the breast adapter will be captured between the flanges 510 and 512 in the gap 514, so that no milk spillage will occur. During the extraction phase, when the higher suction/vacuum is applied (e.g., −180 mm Hg, −200 mm Hg or −220 mm Hg), the stronger suction/vacuum collapses the gap 514 and the resulting contact between the secondary flange 512 and primary flange 510 drives out any milk that may have been present in the gap 514 and into the tube 32. The collection of milk in gap 514 will occur even if the breast moves away from the flange 512 momentarily during an extraction phase, as this results in a loss of suction/vacuum and the gap 514 immediately reopens.

Figure 52A:
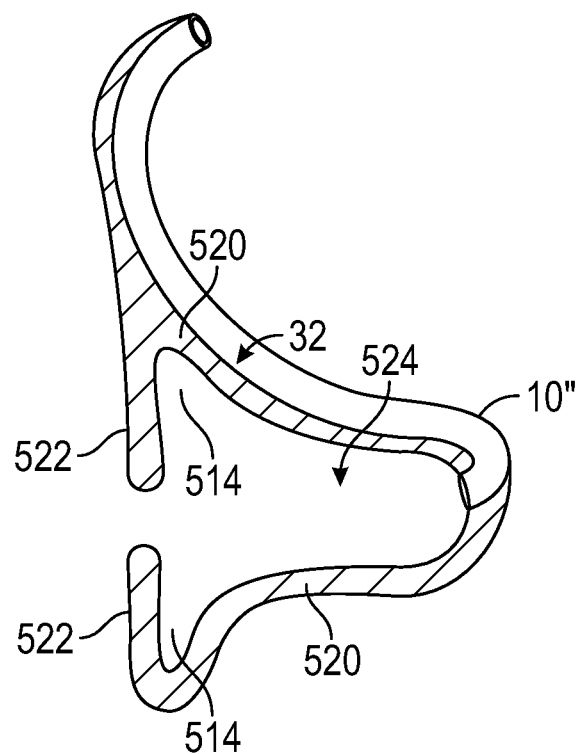
FIG. 52A shows a longitudinal sectional view of a breast adapter that that may be used in any of the breast pump systems described herein, and which is a variation of the breast adapter shown in FIG. 51.
Figure 52B:
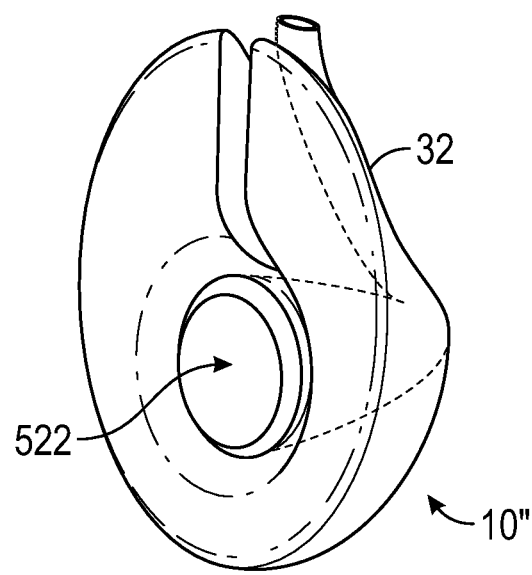
FIG. 52B is a rear perspective view of the breast adapter and tube of FIG. 52A.
Figure 52C:
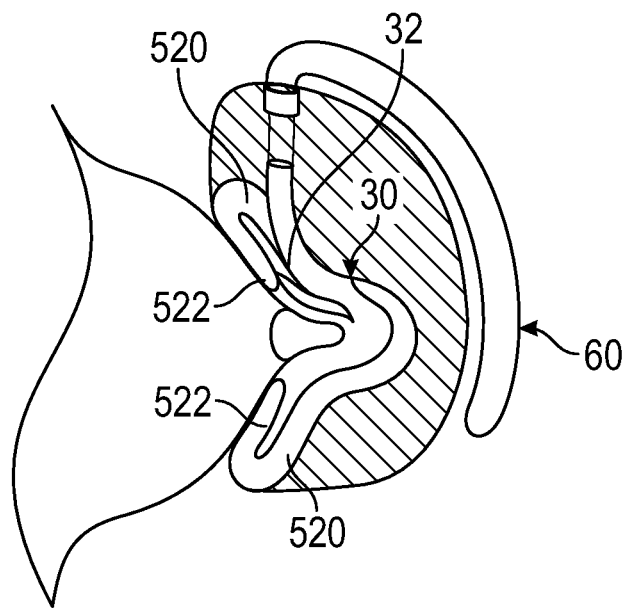
FIG. 52C illustrates that when the breast is engaged with the system, the lip of the system is deflected further inwardly by the breast contact, thereby reducing or eliminating the gap and driving milk from the gap towards the nipple housing/nipple receiving cavity, according to an embodiment of the present disclosure.

FIG. 52A shows a longitudinal sectional view of a breast adapter 10" that that may be used in any of the breast pump systems described herein, and which is a variation of the breast adapter 10' shown in FIG. 51. In addition to the primary flange 520 provided for receiving a portion of the breast 2 therein, adapter 10" includes a second flange 522 in the form of a flexible lip that extends radially inwardly from the primary flange 520 and contacts the breast 2 when the breast is inserted into the system for carrying out an extraction session. FIG. 52B is a rear perspective view of breast adapter 10" and tube 32 showing the surface of the flexible lip 522 in its unbiased configuration, where it extends radially inwardly and, together with flange 520, forms gap 514. Deflectable lip 522 is designed to remain in contact with the breast 2 at all times during wearing of the system and preferably forms a seal with the breast. When the breast 2 is engaged with the system, the lip 522 is deflected further inwardly by the breast contact (see FIG. 52C), thereby reducing or eliminating the gap 514 and driving milk from the gap 514 towards the nipple housing space 524. When the system breaks contact with the breast, the deflectable lip resiliently returns to the unbiased position shown in FIGS. 52A-52B and captures any excess milk left in the nipple housing space, preventing it from spilling out of the breast adapter 10".

Figure 53A:
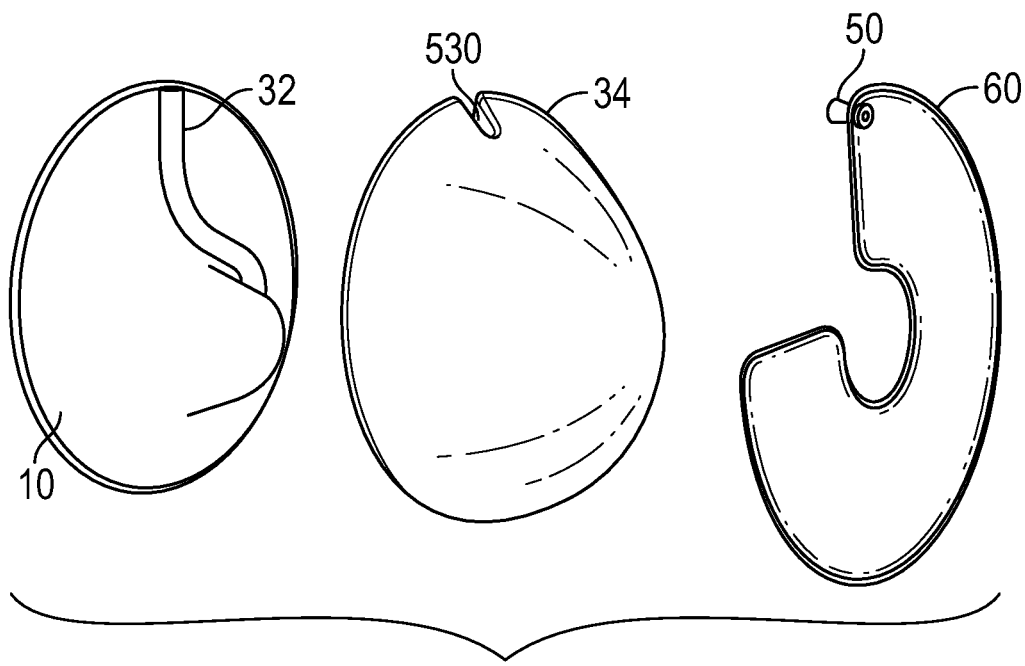
FIG. 53A is a front, exploded view illustrating a breast adapter and tube, main housing 34 and milk container 60 according to an embodiment of the present disclosure.

FIG. 53A is a front, exploded view illustrating the breast adapter 10 and tube 32, main housing 34 and milk container 60 according to an embodiment of the present disclosure. The main body/housing is smoothly contoured on its distal surface, so as to form a visual impression of the breast 2 when received in bra 130. A notch 530 is provided at the top of the main body 34 that is configured and dimensioned to receive the one-way valve 50 of container 60 for connection to tube 32.

Figure 53B:
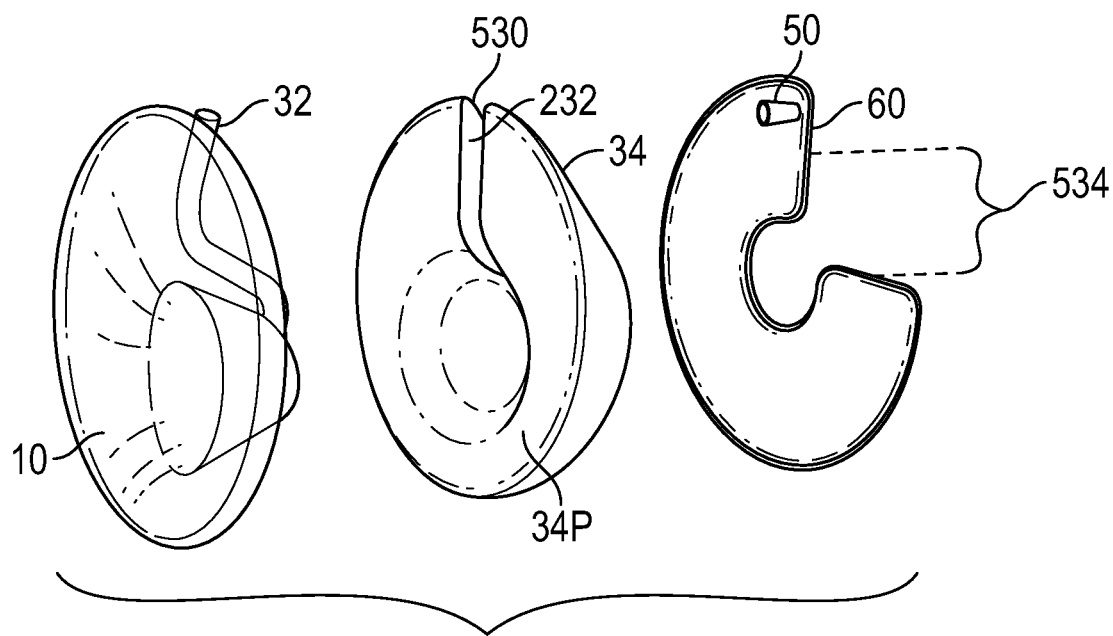
FIG. 53B is a rear, exploded view of the components illustrated in FIG. 53A.

FIG. 53B is a rear, exploded view of the components illustrated in FIG. 53A. This perspective better shows the contours of the main body 34, illustrating its "egg-shape" or "pear-shape" front profile. Also shown is the location of the nipple cavity 532 that is below the center of the main body 34. The proximal (rear) surface 34P of the main body 34 is concavely contoured and the breast adapter 10 follows this contour so as to cup the breast 2 as it is received and provide comfort and low profile.

Figure 53C:
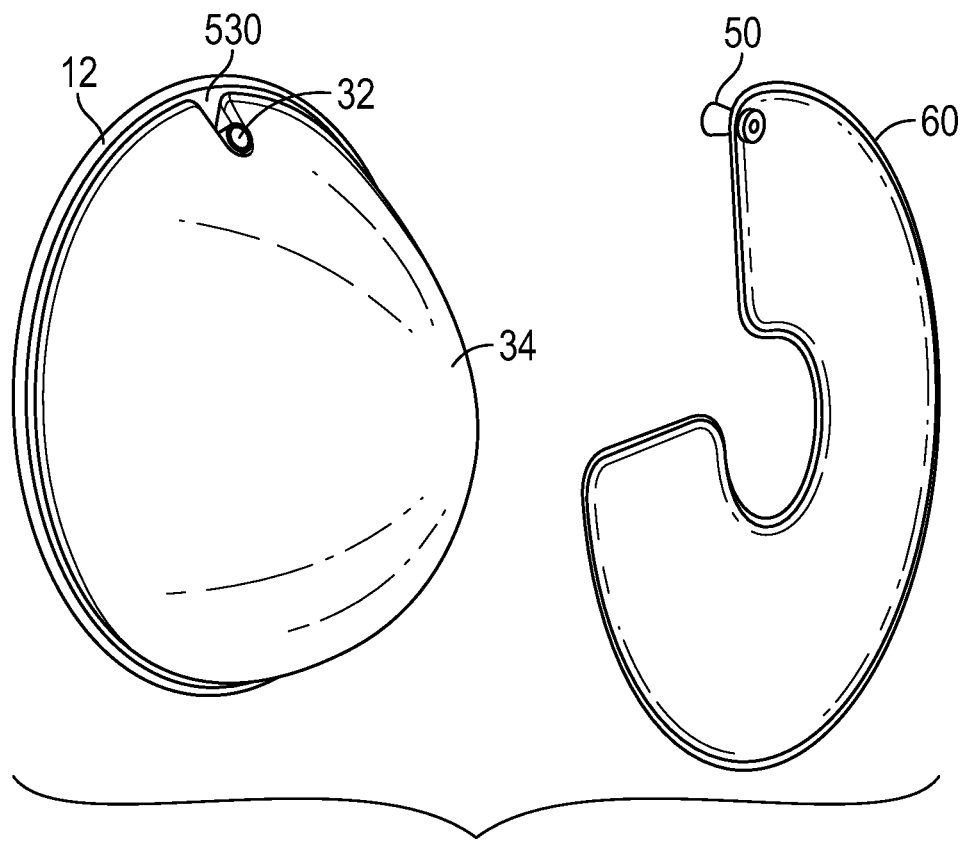
FIG. 53C is a front, perspective view illustrating the breast adapter and tube of FIG. 53A having been installed in the main body.
Figure 53D:
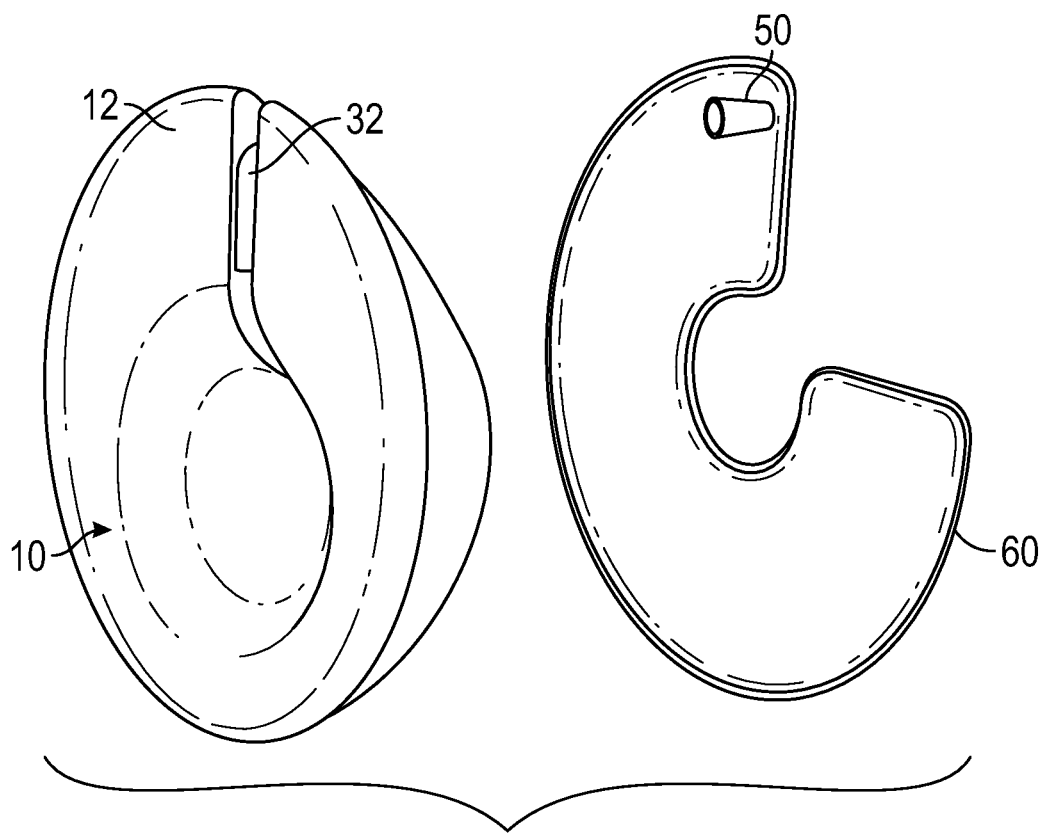
FIG. 53D is a rear, perspective view of the components shown in FIG. 53C.

FIG. 53C is a front view illustrating the breast adapter 10 and tube 32 having been installed in the main body 34. The compliant region 12 of breast adapter 10 overlies the edge of main housing 34 so that no seams or edges are present when the breast adapter is in contact with the skin of the breast 2. The proximal end of tube 32 is shown located within the notch 530, in preparation for connection of the container 60 thereto via one-way valve 50. FIG. 53D is a rear view of the components shown in FIG. 53C. The smooth interface provided by the compliant region overlapping the edge of the main body 34 can be seen, and tube 32 can be seen extending up to the notch 530.

Figure 53E:
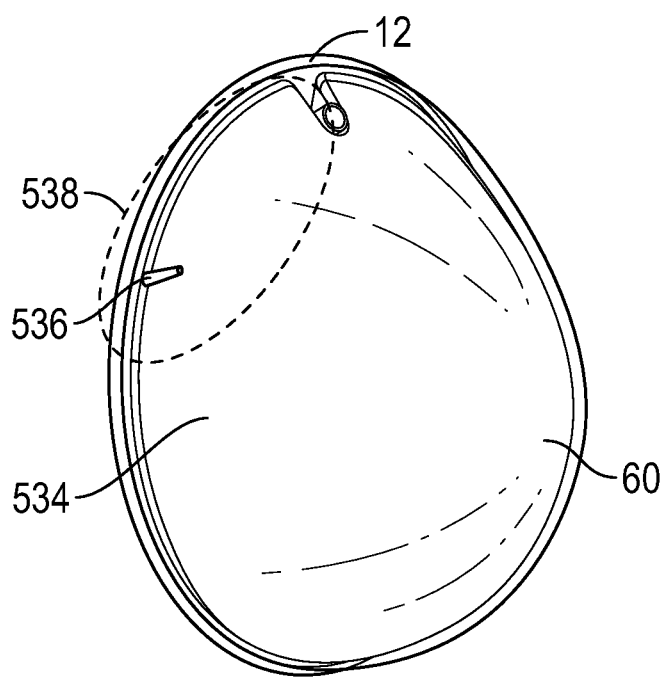
FIG. 53E illustrates a front, perspective view after attaching the container to the main body of the embodiment illustrated in FIGS. 53A-53D.
Figure 53F:
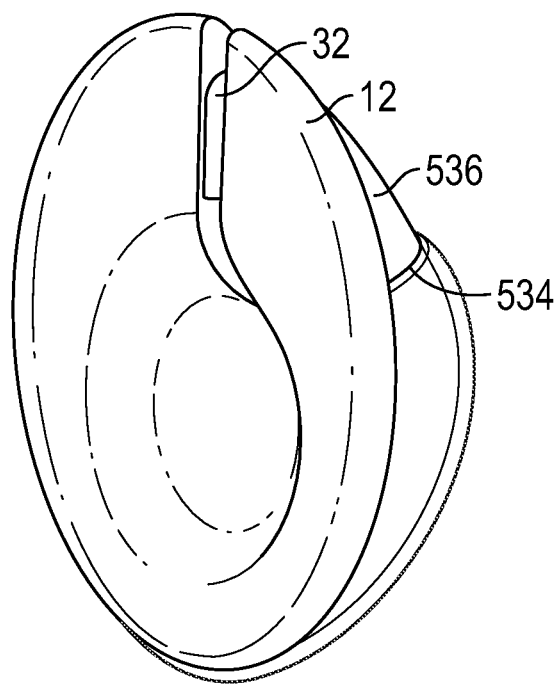
FIG. 53F is a rear, perspective view of the system shown in FIG. 53E.
Figure 53G:
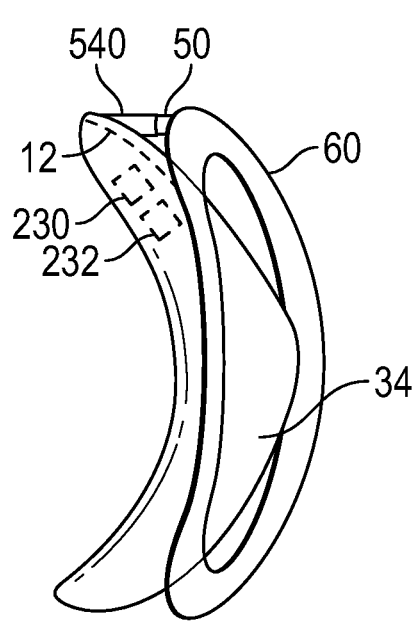
FIG. 53G illustrates a breast pump system using a full ring-shaped container, according to another embodiment of the present disclosure.

FIG. 53E illustrates a front view after attaching the container 60 to the main body 34. The container 60 in this embodiment defines a cut-out region 534 that is a spaced formed where the container is absent, such that it does not form a full ring. This cut out region 534 as shown spans about ninety degrees of the ring space, but may be as low as about forty—five degrees or as large as about one hundred thirty five degrees, or spans a region anywhere in between 45-135 degrees. The region 536 (emphasized by dotted ellipse 538 in FIG. 53E) that is not covered by the container 60 when container 60 is mounted on main body 34, better allows the container 60 to conform to the shape/contours of the main body 34 and also provides an open area where the controls 252 and/or display 250 can be provided on the main body. FIG. 53F is a rear view of the assembly shown in FIG. 53E. Alternatively, container 60 may be provided as a full ring, as illustrated in FIG. 53G, or other container configurations, such as those described herein may be used. In FIG. 53G, container 60 is attached to main body 34 by a short tab or tubular extension 540 that interconnects tube 32 and one-way valve 50. The extension 540 positions container 60 so that a portion of main body 34 is visible on either side of the extension, so that controls 232 and/or display 230 can be positioned for viewing by the user. Extension 540 also provides an even hanging/balance to the container as it fills up with milk.

Figure 54:
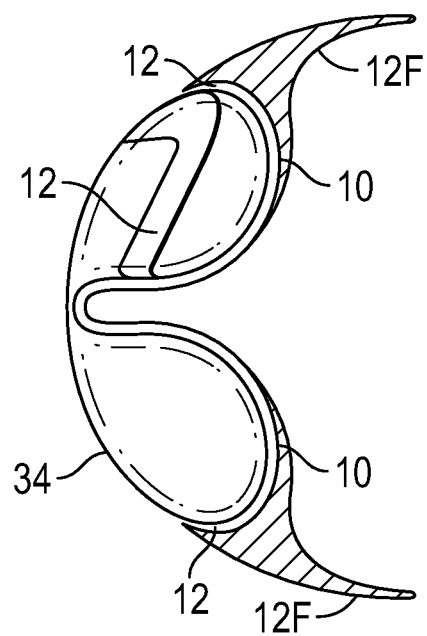
FIG. 54 illustrates an assembly of the breast adapter and tube in the main body according to another embodiment of the present disclosure.

FIG. 54 illustrates an assembly of the breast adapter 10 and tube 12 in the main body 34 according to another embodiment of the present disclosure. In this embodiment, flanges 12F are provided to extend distally from the overlap of compliant region 12 on the edge of main body 34. The flanges 12F also taper distally to form a smoother transition with the breast 2 when the system 100 is mounted on the breast 2, thereby making the system 100 less visible or noticeable when worn by a user. The tapered, thin flexible flange 12F extends distally from the outer edge of the compliant region 12 that snaps around the circumference of the main body 34 of system 100. Flexible flange 12F is preferably, but not necessarily integrally formed with the compliant region 12 and breast adapter 10.

FIGS. 55A-55E illustrate the interaction between compression elements 36, 38 and resilient tubing 32 and a pumping sequence according to another embodiment of the present disclosure. In this embodiment, compression element 36 comprise a short length compression effector 36A (in this case, compression effector 36A has the same length or diameter of the shaft of the compression element 36 and may optionally be simply the free end of the shaft), to reduce the amount of force necessary to function as a shut off valve by sealing the region 40. The compression element 38 in this embodiment moves horizontally (in the Figs, but could be a different direction depending upon the orientation of the system) along the length direction of the tube 32. Thus rather than moving against the tubing 32 radially inwardly or retracting away from the tubing 32, compression element 38 rolls or slides along the tube to change the suction/vacuum levels in the system.

Figure 55A:
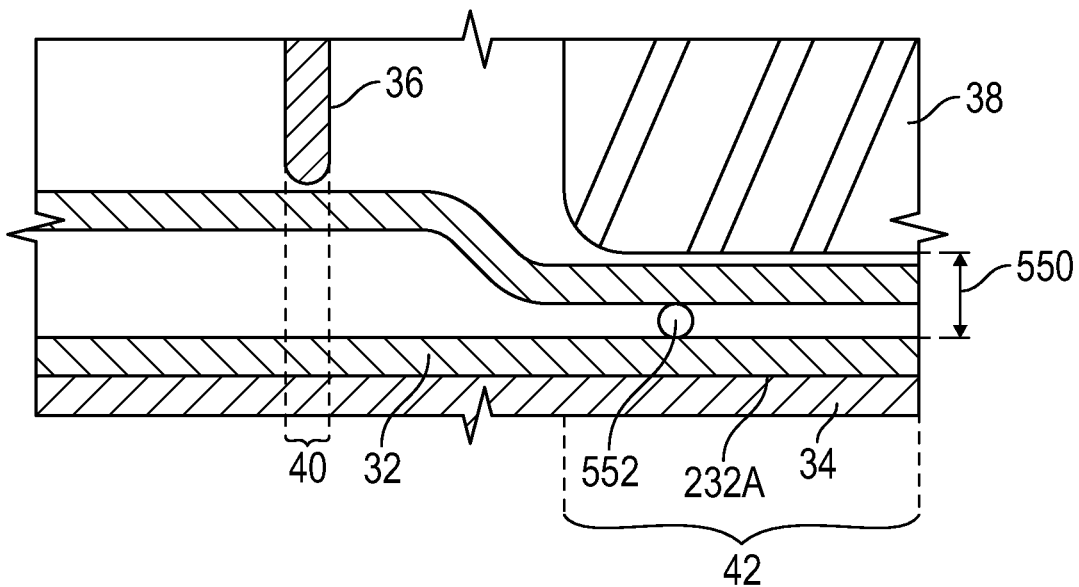
FIGS. 55A-55E illustrate the interaction between compression elements and resilient tubing, and a pumping sequence, according to another embodiment of the present disclosure.

The compression surface of the compression element 38 maintains a constant distance 550 from the anvil surface 232A of the channel 232 that the tube is positioned in. This maintains the tube 32 in an unsealed configuration, such that the tube portion that is between the compression element 38 and anvil surface 232A is maintained in a collapsed, but not sealed condition, see 552. FIG. 55A shows an orientation in which the minimum suction/vacuum (e.g., −60 mmHg or −50 mm Hg, or some other predetermined minimum) is maintained against the breast. The compression element 36 is fully retracted away from the tube, so that the tube is not compressed in region 40. In this phase, the majority of the tubing region 42 is compressed, but not sealed off.

Figure 55B:
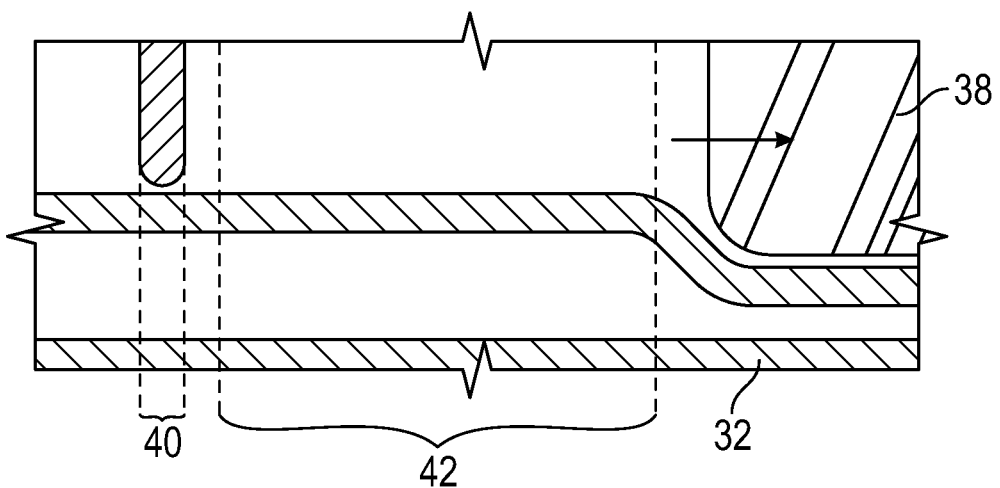
Figure 55C:
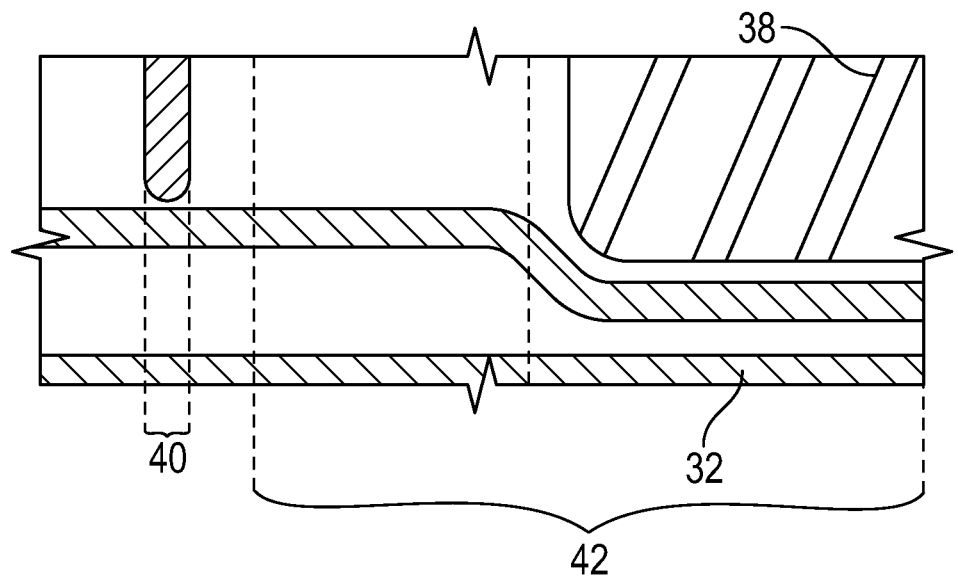

To move the system to an active suction phase, where the maximum predetermined suction/vacuum is generated (e.g., −200 mm Hg, −220 mm Hg or some other predetermined maximum suction/vacuum level) the compression element 36 maintains it position and the compression element 38 is slid or rolled in a direction away from the breast to enable tubing region 42 to return to its uncompressed configuration and generate suction/vacuum, see FIG. 55B. The compression element 38 can be continuously controlled by controller 52 using feedback from pressure sensing the suction/vacuum space, to move toward or away from the breast in order to maintain the predetermined maximum suction/vacuum level, which can be programmed into the controller for use in the feedback loop used to maintain the maximum suction/ vacuum. Movement toward the breast decreases the suction/vacuum while, conversely, movement away from the breast increases the suction/vacuum. FIG. 55C shows the compression element 38 having been returned to the position shown in FIG. 55A to re-establish the predetermined minimum suction/vacuum, in this case, −60 mm Hg. The change in volume within the tubing between the distal end of compression element 38 and the breast 2 when moving from the position of element 38 in FIG. 55B to the position in FIG. 55C is the volume of milk expressed during that cycle, assuming no air leaks to the system. Thus by knowing the inside diameter of tube 32 and the relative positions of compression element 38 (as tracked by controller 52), an estimate of the volume of milk that is moved proximally of the compression element 38 can be calculated by the controller 52. Further, the calculated estimates of volume can be displayed on the system display 230, wirelessly outputted to an external computing device such as a smartphone or other computer, and/or uploaded to the Internet, such as to a web-based cloud server.

Figure 55D:
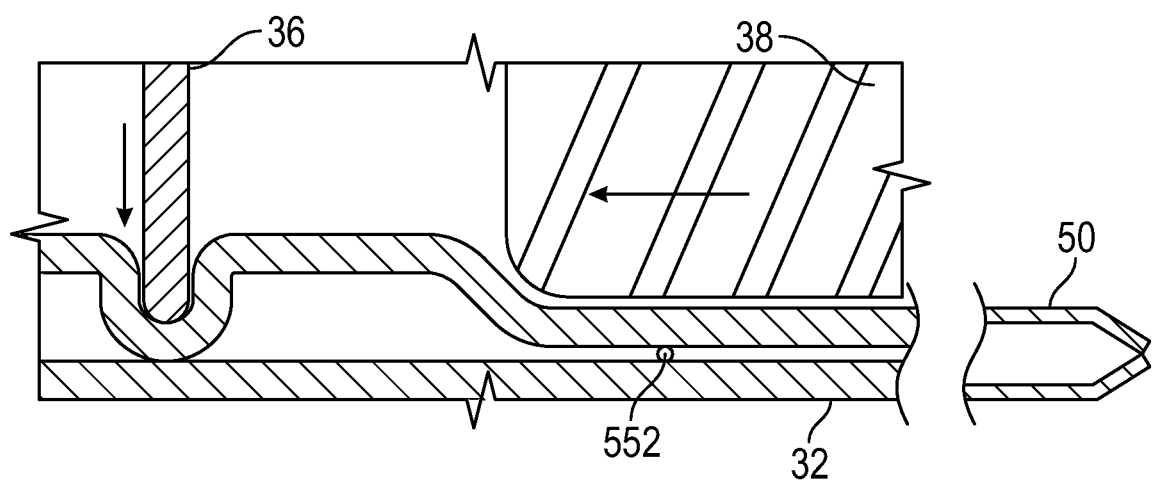
Figure 55E:
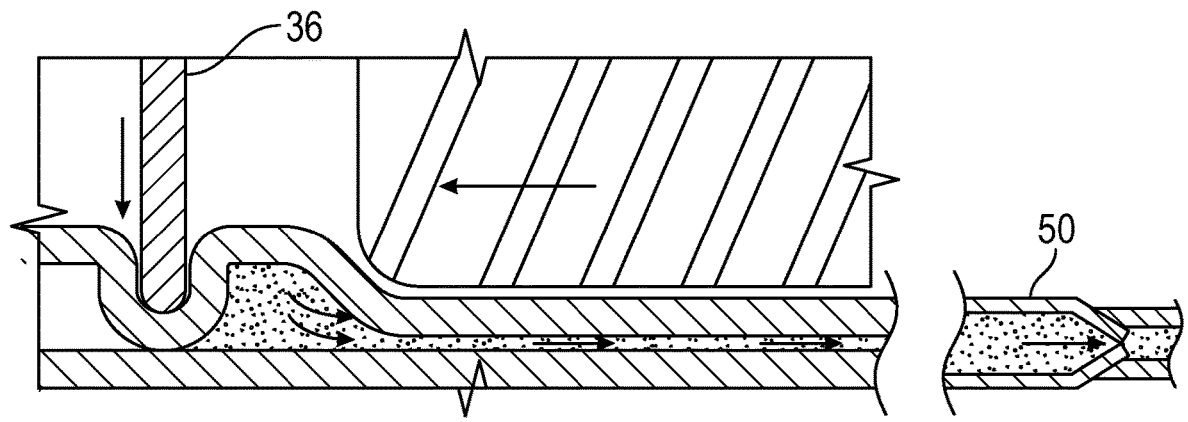

As the predetermined minimum suction/vacuum level is reached, the compression element 36 is actuated and driven to seal off the tubing in region 40, as shown in FIG. 55D. Note that the tubing 32 in contact with element 38 is not sealed off, see 552. Once the tube 32 is sealed off by element 36 so that the minimum suction/vacuum level is maintained against the breast 2, compression element 38 is rolled or slid toward the breast (and toward element 36) to transfer the volume of milk located between the elements 36 and 38 distally of element 38 and out through one-way valve 50 into the collection container 60, as illustrated in FIG. 55E. The movement of element 38 toward element 36 generates a positive pressure in the space between elements 36 and 38 that drives the milk out through the partially opened tube 552, 32 and proximally of the element 38. After completing the expulsion phase illustrated in FIG. 55E, the compression element 36 is retracted while maintaining at least the minimum suction/vacuum level against the breast by adjusting the element 38 as needed as the cycle returns to FIG. 55A in preparation for another extraction phase.

Figure 12:
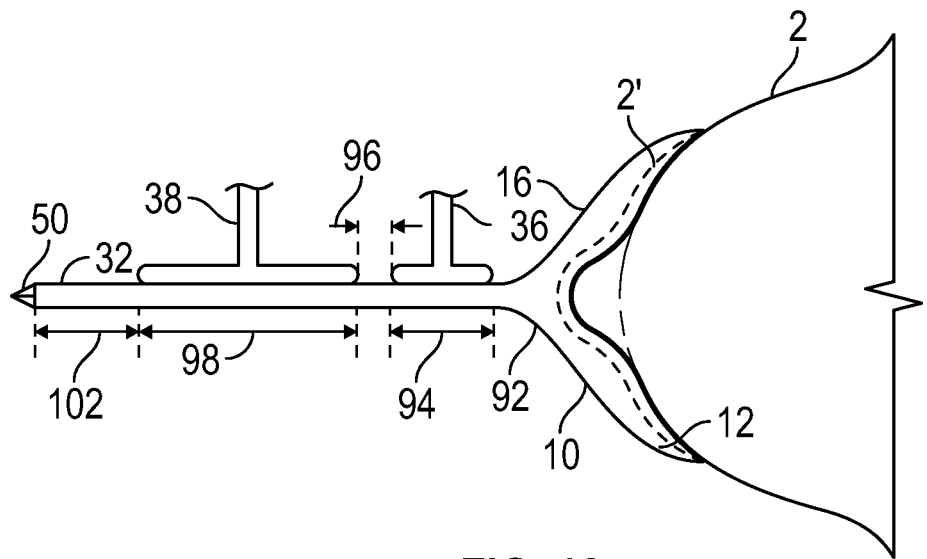
FIG. 12 schematically illustrates various sections of the tube extending from the breast to the proximal end of the tube, according to an embodiment of the present disclosure.

The amount of dead space in the system, e.g., the summation of spaces 92 and 96 in FIG. 12, impacts the size and characteristics of the tubing 32 needed to generate sufficient suction/vacuum levels. A relatively larger dead space requires a relatively larger inside diameter of tube 32 and/or active tubing length (i.e., the length of tube 32 that is compressed and released to generate suction/vacuum, such as the region 42 in FIGS. 55A-55E). Additionally, the dead space will change as the suction/vacuum level is increased and the nipple 3 is sucked further into the nipple reception cavity of the breast adapter 10, thereby reducing the volume of the dead space somewhat. Expression of milk decreases the active suction/vacuum level applied. This decrease in suction/vacuum can be measured to estimate the volume of milk having been expressed. Further, the pressure sensor used for suction/vacuum level measurement can be used in an active feedback loop by the controller 52 to adjust the compression element 38 (or, in other embodiments, both elements 36 and 38) to maintain the desired, predetermined maximum suction/vacuum level. The maximum suction/vacuum level that the system is capable of generating is governed by the properties of the tube 32, including inside diameter, wall thickness, material and durometer of the tube 32. In the embodiment of FIGS. 55A-55E, the tubing 34 is configured with a capacity to generate a suction/vacuum that exceeds the predetermined maximum suction/vacuum level.

When there is no flow of milk in the tube 32, the pumping region 32 may lose the ability to cycle through the full range of predetermined suction/vacuum pressures, and will maintain a lower mean suction/vacuum pressure. For example, when flow discontinues, the system may not be able to cycle up to −60 mm Hg, but, instead alternates between −200 mm Hg and −90 mm Hg. Controller 52 can be programmed to review pressure readings from a predetermined number of previous cycles and evaluate at least one of: the pressure peaks of the waveforms of the predetermined number of previous cycles; or calculate and compare the mean suction/vacuum pressure levels of the predetermined number of previous cycles. If the pressure has not reached the predetermined minimum suction/vacuum level (e.g., −60 mm Hg) during the predetermined number of previous cycles, this indicates that the milk expression and expulsion session has ended, as there is no more flow in the tube 34. When such an event is reached, the controller 52 may be programmed to automatically shut off the system 100. This routine would not be active during the letdown phase, e.g., during the first four minutes (or other predetermined time period measured from commencement) of the pumping cycle as the user is in the letdown phase and is not expressing milk. When the system automatically shuts off the controller can indicate on display 250 the pumping session has ended and/or send an alert to an external computer such as a smartphone or other device to indicate that the pumping session has ended. Additionally, the estimate volume of milk pumped during the session can be displayed on the display 250 and/or sent to an external computer.

Figure 56:
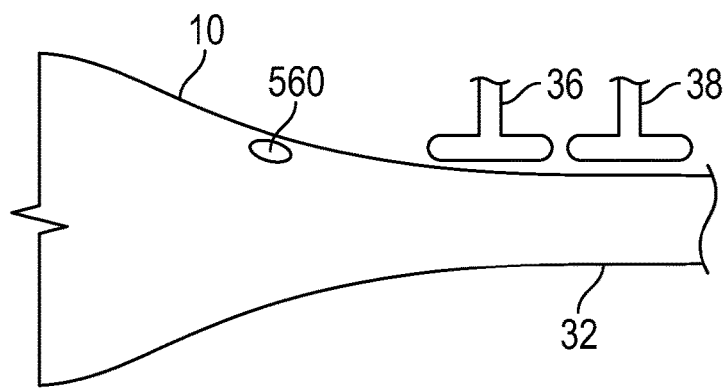
FIG. 56 illustrates a flow sensor provided in a breast pump system to enable the user to check in real time how much milk has been pumped, according to another embodiment of the present disclosure.

Alternatively a flow sensor 560 may be provided in the system (see FIG. 56) to enable the user to check in real time how much milk has been pumped, as a real time real running total of milk volume can be estimated and displayed on display 250 and/or sent to be displayed on a smartphone or other external computer. The controller 52 can be programmed such that, when monitoring the flow sensor 560, it will automatically shut off the system after a predetermined time period (e.g., two minutes, four minutes, or some other predetermined time period) has passed during which there has been no milk flow.

In addition to sensing when milk expression stops or when collection vessel 60 is full, the system 100 can also auto detect when full let down occurs. The pump region 30 may start with a preprogrammed cycle that is intended to assist in letdown. This cycle is typically faster in frequency and shallower in vacuum amplitude than that of the expression cycle. The initial let down cycle may be modified by a user to fit the user's personal preferences via a "learning" or "program" mode in the controller 52 of system 100. While the system is going through its initial "letdown" cycle, it can track the pressure changes in the breast area. Once milk flows, it will affect the pressure positively. Upon such a change—with appropriate delays, checks, confirmation, the program can automatically switch to a deeper, fuller expression mode where the cycle typically slows down and pressure (vacuum) amplitude increases. Additionally, while in expression mode, the system can monitor pressure changes. Knowing compression elements 36, 38 positions, speed, power, and pressure generated (immediate, history, expected) the system can monitor and calculate milk expression flow or some corollary measure that is relative to flow. The system can then optimize its action (frequency, pressure profile, etc.) to optimize milk expression.

The controller 52 of the system 100 can optionally be programmed to "overshoot" some meaningful amount of pressure or frequency to help "push" the demand experienced by the mother and help enhance the breast's mechanism to increase supply.

Figure 57:
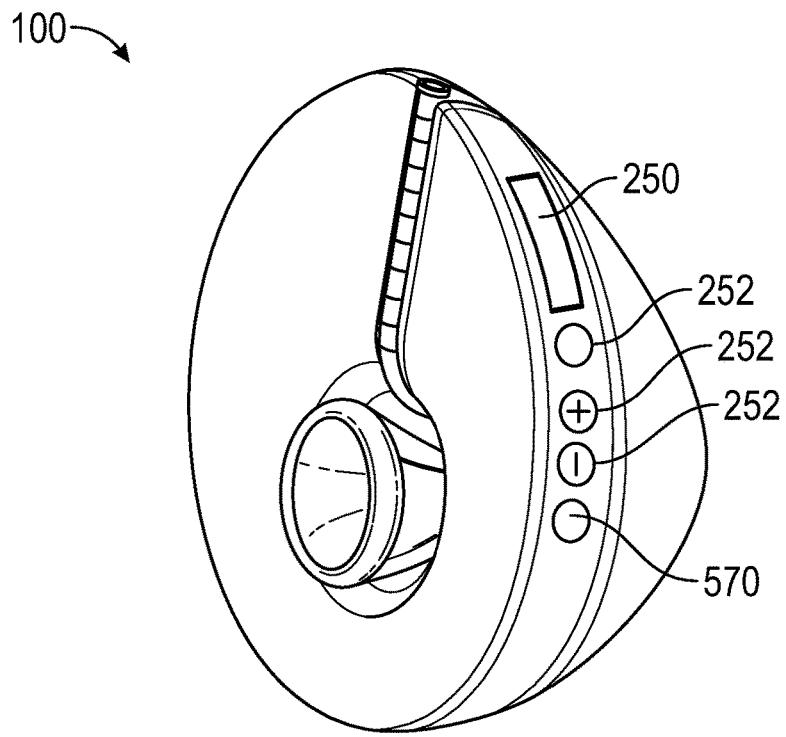
FIG. 57 illustrates a breast pump system provided with an indicator light, according to an embodiment of the present disclosure.

By providing a tube 32 designed to create a maximum value that exceeds the predetermined maximum operating suction/vacuum, this enables the system to have enough reserve capacity so that, after the pumping region 30 has finished cycling (either because the user manually shuts it off or the cycles were stopped automatically though feedback because there was no more milk expressed), the compression elements 36, 38 have reserve travel remaining so that they can be further operated to further compress the tube 32 in order to return the suction/vacuum pressure of the system to zero so that the user doesn't feel the feeling of removing a suction cup from the breast 2, but rather the system readily detaches or falls off, without any remaining suction resisting removal. This operation to return the suction/vacuum to zero can be automatically carried out as part of the shutdown process of the system. The system 100 can be provided with an indicator, such as an indicator light, audible indicator, or other indicator readily interpreted by the user to indicate to the user when the suction/vacuum has been removed after shutdown. FIG. 57 illustrates an embodiment of system 100 according to the present disclosure which has been provided with an indicator light 570. When the system 100 is manually shut down by the user, the indicator light changes from a green color to a red color, for example, and after a predetermined time (e.g., two seconds or some other predetermined time) the red light stays on while the system operates the pumping region 30 to return the pressure level to zero. Once the pressure returns to zero, the indicator light turns off, indicating to the user that it is okay to remove the system 100 from the breast 2.

Figure 58A:
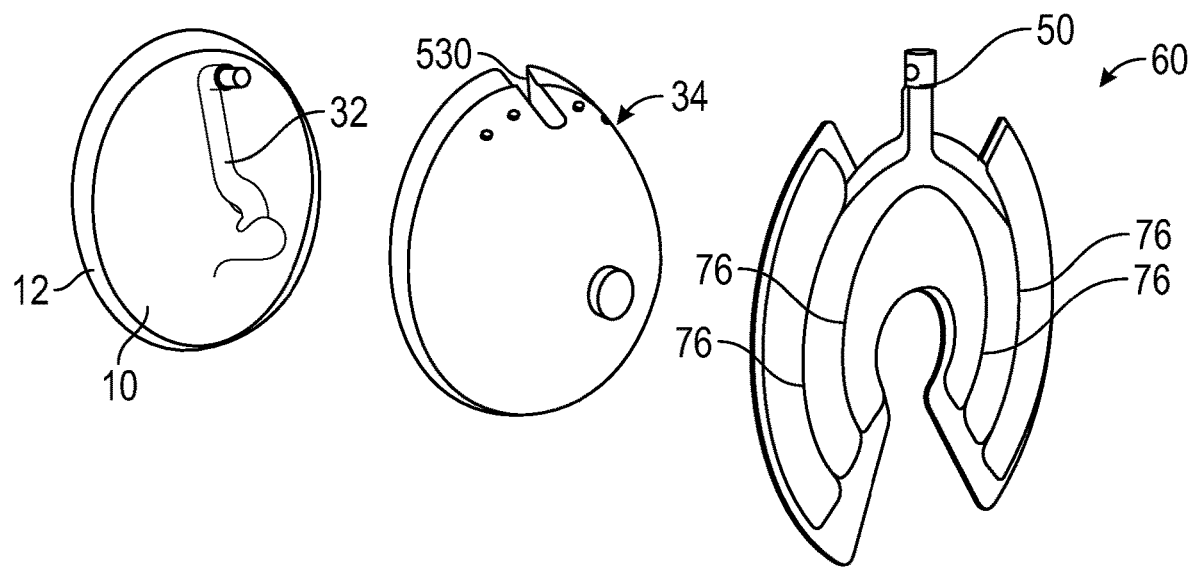
FIG. 58A is a front, exploded view of a breast pump system according to another embodiment of the present disclosure.

FIG. 58A is a front, exploded view of system 100 according to another embodiment of the present disclosure, illustrating breast adapter 10 and tube 32, main housing 34 and milk container 60 according to an embodiment of the present disclosure. The main body/housing is smoothly contoured on its distal surface, so as to form a visual impression of the breast 2 when received in bra 130. A notch 530 is provided at the top of the main body 34 that is configured and dimensioned to receive the one-way valve 50 of container 60 for connection to tube 32. Container 60 is provided with baffles 76 to help maintain the shape of the container 60 to conform to the main body 34 as it fills with milk.

Figure 58B:
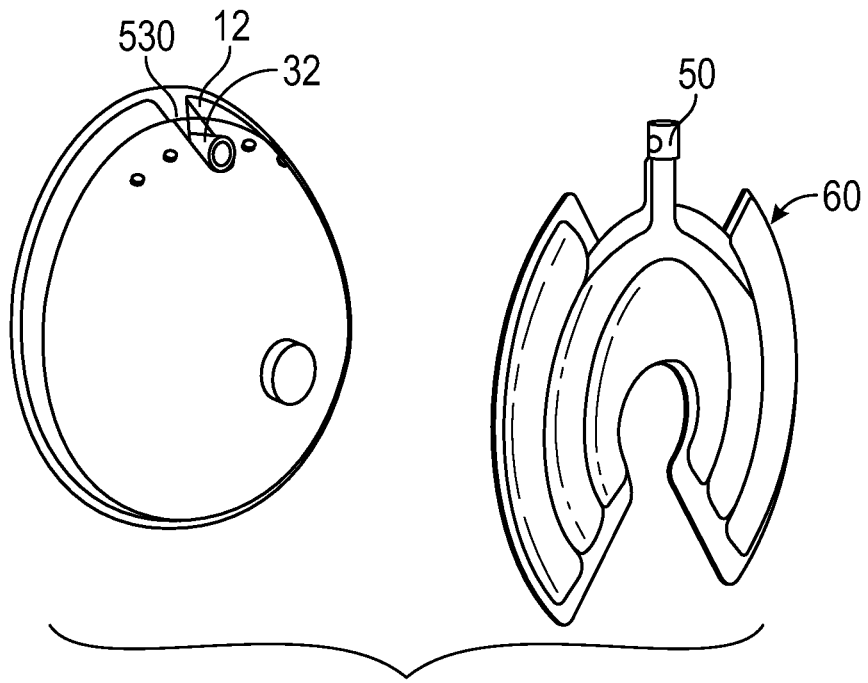
FIG. 58B is a front view illustrating the breast adapter and tube having been installed in the main body.

FIG. 58B is a front view illustrating the breast adapter 10 and tube 32 having been installed in the main body 34. The compliant region 12 of breast adapter 10 overlies the edge of main housing 34 so that no seams or edges are present when the breast adapter is in contact with the skin of the breast 2. The proximal end of tube 32 is shown located within the notch 530, in preparation for connection of the container 60 thereto via one-way valve 50.

Figure 58C:
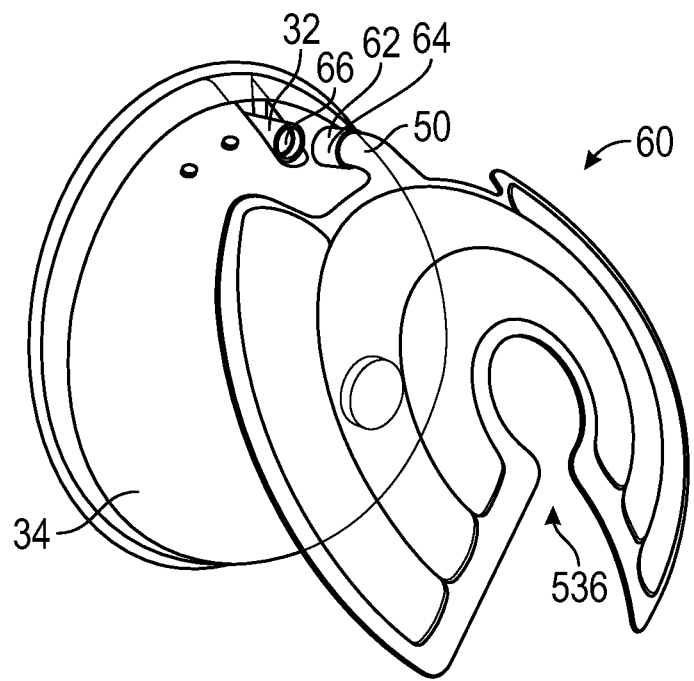
FIG. 58C illustrates the process of attaching the container to the system.

FIG. 58C illustrates the process of attaching the container 60 to the system. As the extension 62 is inserted into the distal end 66 of tube 32 so that detents 64 are received in mating receptacles in the distal end 32 to connect (with optional inclusion of one or more seals such as O-rings, or the like) the container 60 and tube 32 with a liquid-tight, airtight connection, the container 60 is fitted over the main body 34, so it conforms closely to the shape of the front surface of the main body, so as to be well-concealed within a bra. Container 60 in this embodiment is not continuously concentric, but forms a cutout region 536 (at the bottom portion of the container in this embodiment) to allow the container 60 to assume a curved concave surface to follow the convex surface of main body 24 without wrinkling or buckling. The cutout region may be wedge-shaped, as shown and span about 25 to 45 degrees of the circular shape of the container 60 when it is laid flat.

Figure 58D:
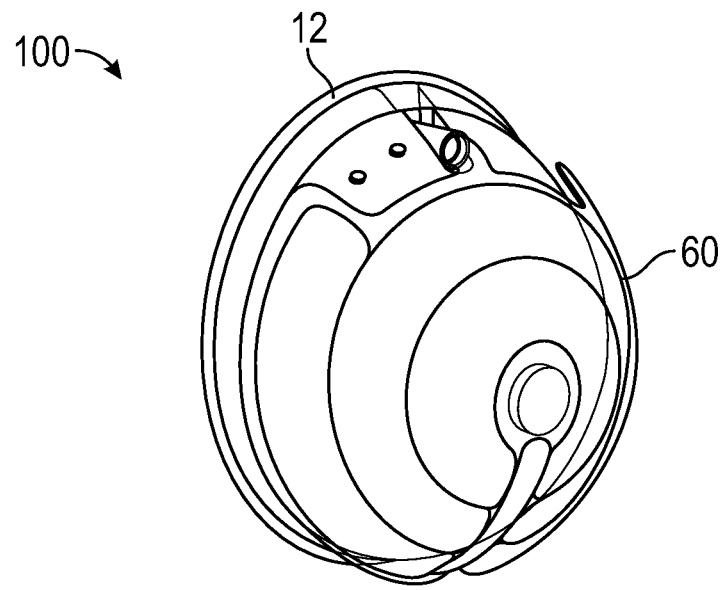
FIG. 58D illustrates the assembled system, with the container having been connected and fitted over the main body to conform to the contour thereof.
Figure 58E:
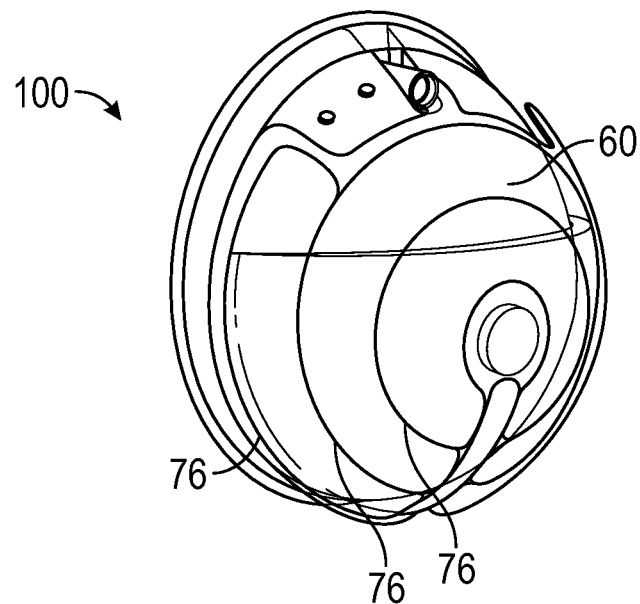
FIG. 58E shows the system of FIGS. 58A-58D with the container having been partially filled with milk.

FIG. 58D illustrates the assembled system 100, with the container having been connected and fitted over the main body 34 to conform to the contour thereof. FIG. 58E shows the system 100 with the container 60 having been partially filled with milk 4. The baffles 76 are illustrated as facilitating the even distribution of milk 4 in the container 60 as the container maintains its original configuration following the contours of the front surface of main body 34.

Figure 59A:
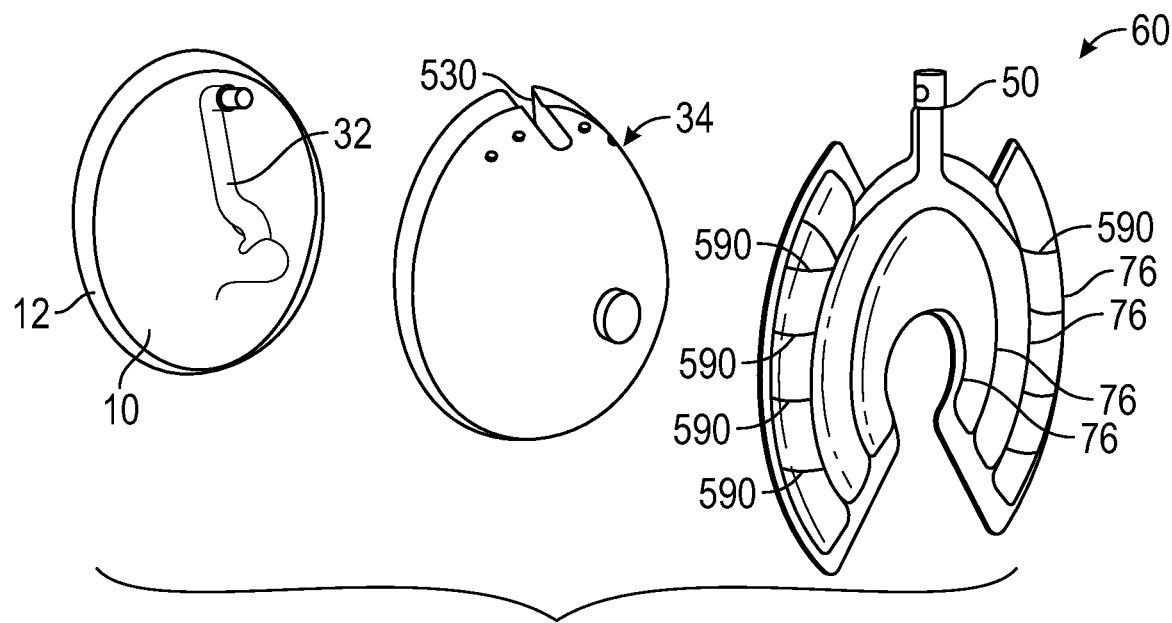
FIG. 59A is a front, exploded view of a breast pump system according to another embodiment of the present disclosure.

FIG. 59A is a front, exploded view of system 100 according to another embodiment of the present disclosure, illustrating breast adapter 10 and tube 32, main housing 34 and milk container 60 according to an embodiment of the present disclosure. This embodiment is essentially the same as the embodiment of FIGS. 58A-58E, except that container 60 is provided with graduation markings 590 configured to accurately measure the amount of milk collected. In the embodiment shown, the graduation markers 590 indicate 1 oz., 2 oz., 3 oz. and 4 oz., respectively. The markers 590 may, of course, be varied to indicate different volume levels, if desired.

Figure 59B:
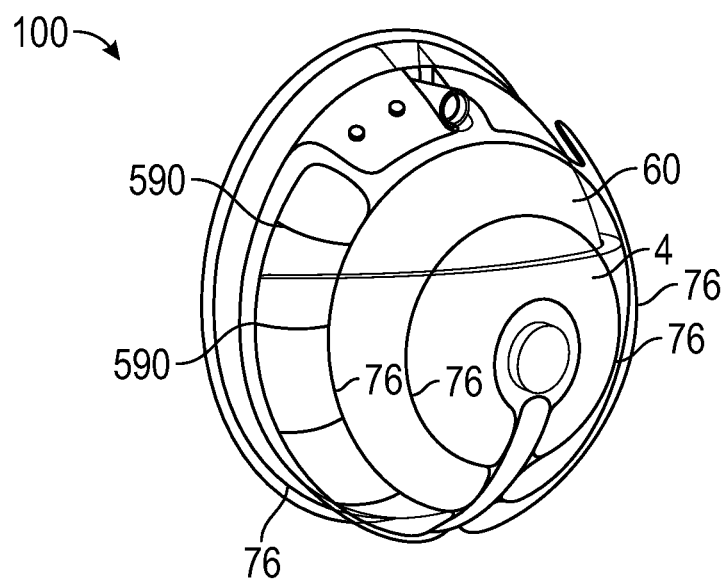
FIG. 59B is a front view illustrating the assembled system, with the container having been connected and fitted over the main body to conform to the contour thereof.

FIG. 59B is a front view illustrating the assembled system 100, with the container 60 having been connected and fitted over the main body 34 to conform to the contour thereof. The container 60 is further shown as having been partially filled with milk 4, with the graduation markers being viewable to estimate that the volume of milk 4 collected is about three and a half ounces. The baffles 76 are illustrated as facilitating the even distribution of milk 4 in the container 60 as the container maintains its original configuration following the contours of the front surface of main body 34.

Figure 59C:
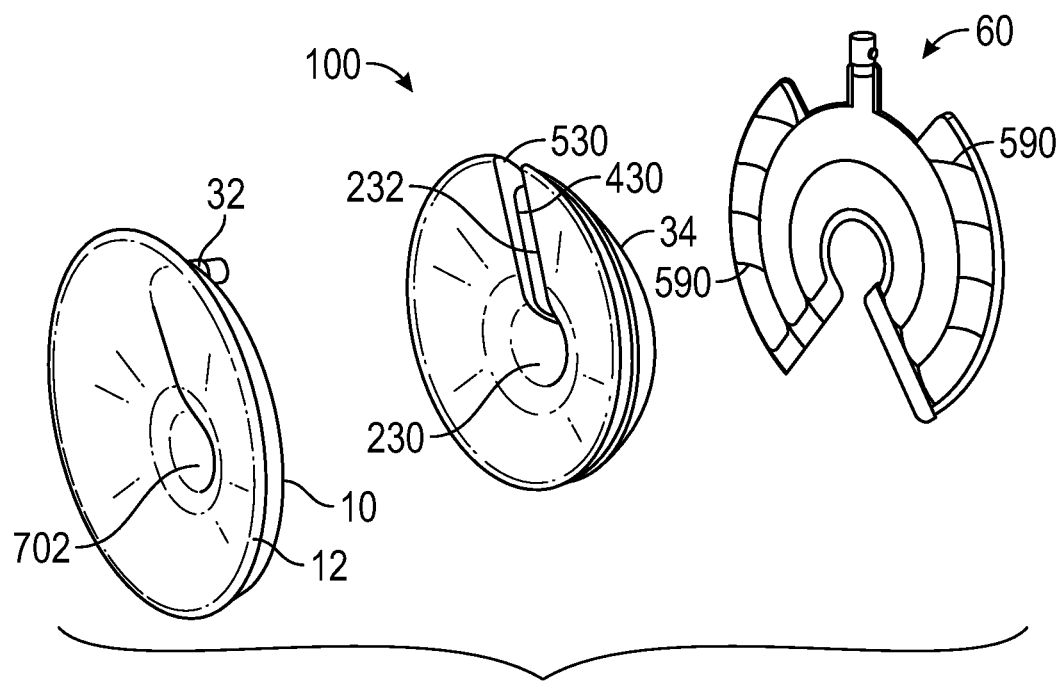
FIG. 59C is a rear, exploded view of the system of FIGS. 59A-59B.

FIG. 59C is a rear, exploded view of system 100 of FIGS. 59A-59B, illustrating the nipple receiving cavity 702 of breast adapter 10 that is configured to receive the nipple 3 while leaving a vacuum-suction space between the nipple 3 and the breast adapter. Also visible from this rear view is the channel 430 in main body 34 that is configured and dimensioned to receive tube 32. The graduation markers 590 on container 60 are also visible from the rear view. The exploded view of FIG. 59C illustrates how the components of the system 100 can be assembled and disassembled. In the embodiment shown, breast adapter 10 is formed integrally with tube/conduit 32 as a single unit. As noted previously, adapter 10 and tube 32 could be formed separately and then joined to form an airtight, liquid-tight connection. In addition to containing the pumping mechanism 30, housing 34 includes a receptacle 230 configured and dimension to receive the breast adapter 10 and snugly hold it in the operable position shown in FIG. 1. Housing 34 also includes a channel 232 configured and dimensioned to receive tube 32 and hold it in proper position so that it can be acted upon by compression elements 36, 38 as intended. Tube 32 can be received in channel 232 with a snap or friction fit, for example, so that it is held in alignment with the compression elements 36, 38, with the closest surface to the compression elements 36, 38 being positioned for movement under compression and resilient return to an uncompressed state, while the opposite surface is held stationary against a surface of the channel 232.

Figure 59D:
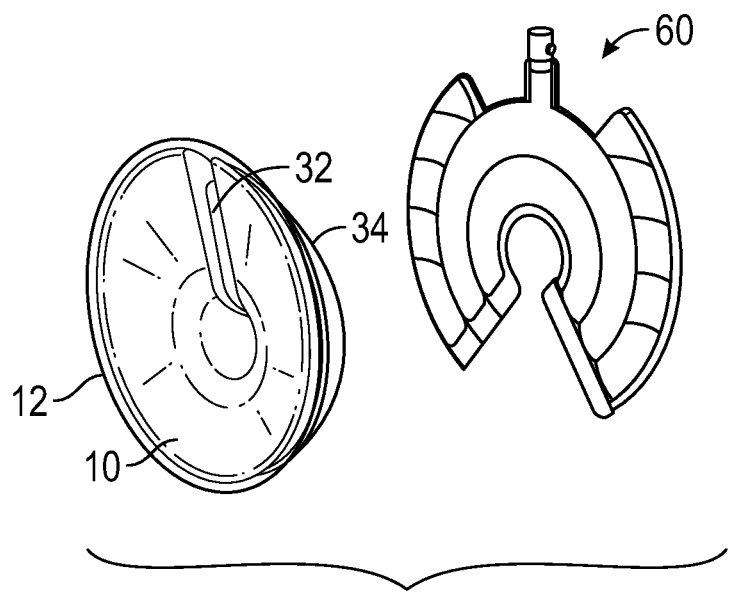
FIG. 59D is a partially exploded rear view of the system of FIG. 59A, showing the breast adapter and tube having been installed in the main body.

FIG. 59D is a partially exploded rear view of the system 100 of FIG. 59A, showing the breast adapter 10 and tube 32 having been installed in the main body 34. The compliant region 12 of breast adapter 10 overlies the edge of main housing 34 so that no seams or edges are present when the breast adapter is in contact with the skin of the breast 2.

Figure 59E:
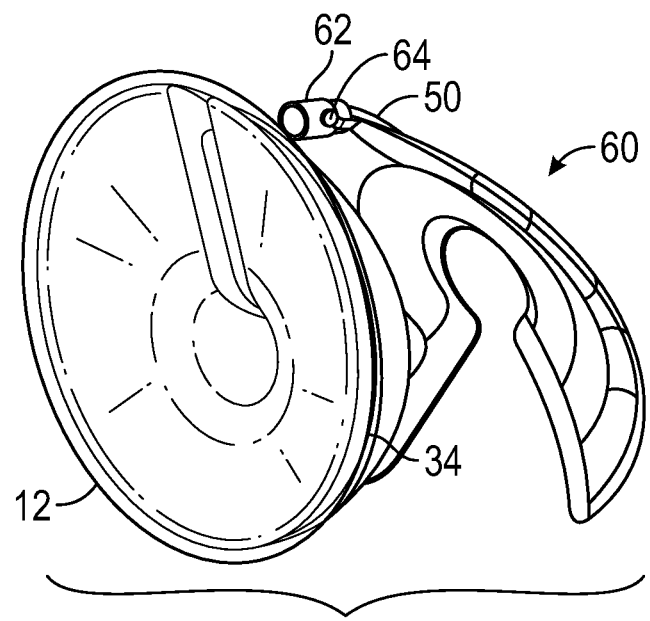
FIG. 59E illustrates the process of attaching the container to the tube and main body.

FIG. 59E illustrates the process of attaching the container 60 to the tube 32 and main body 34. Note that the distal end of the tube 32 is not visible from this view. As the extension 62 is inserted into the distal end 66 of tube 32 so that detents 64 are received in mating receptacles in the distal end 32 to connect (with optional inclusion of one or more seals such as O-rings, or the like) the container 60 and tube 32 with a liquid-tight, airtight connection, the container 60 is fitted over the main body 34, so it conforms closely to the shape of the front surface of the main body, so as to be well-concealed within a bra. Container 60 in this embodiment is not continuously concentric, but forms a cutout region 536 (at the bottom portion of the container in this embodiment) to allow the container 60 to assume a curved concave surface to follow the convex surface of main body 24 without wrinkling or buckling. The cutout region may be wedge-shaped, as shown and span about 25 to 45 degrees of the circular shape of the container 60 when it is laid flat.

Figure 59F:
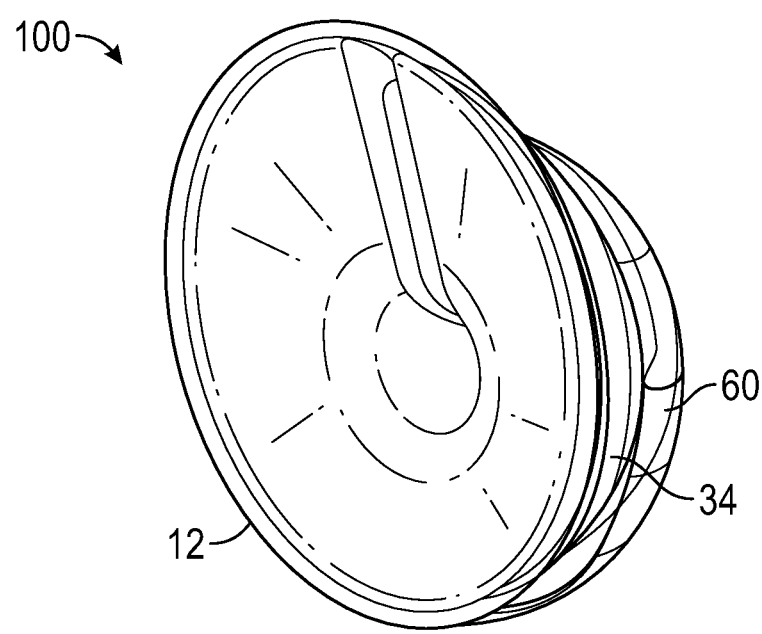
FIG. 59F is a rear, perspective view of the system of FIG. 59A after having been assembled.
Figure 59G:
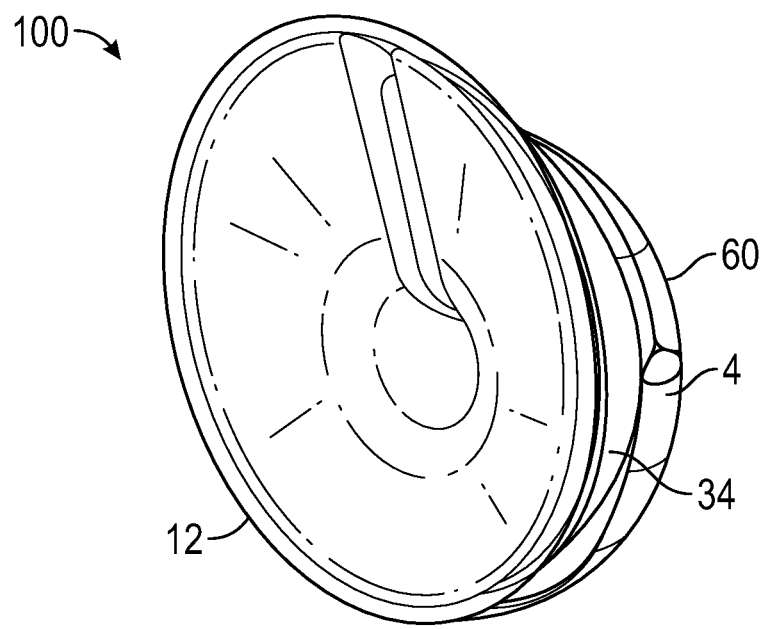
FIG. 59G is a rear view of the system of FIG. 59F after having collected milk in the container.

FIG. 59F is a rear view of the system 100 of FIG. 59A after having been assembled. This rear view shows another perspective of how the container 60 closely conforms to the curvature of the front surface of the main body 34. FIG. 59G is a rear view of the system 100 of FIG. 59F after having collected milk 4 in the container 60. This rear view shows another perspective of how, even after collecting milk to near full capacity, the container 60 continues to closely conform to the curvature of the front surface of the main body 34.

Figure 60:
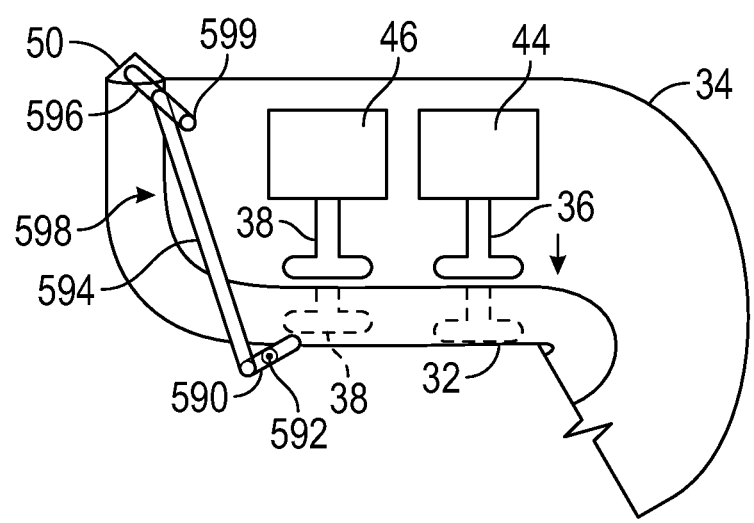
FIG. 60 illustrates a pressure (vacuum) release feature that may be provided on any of the systems described herein, according to an embodiment of the present disclosure.

FIG. 60 illustrates a valve feature that may be provided on any of the systems described herein, according to an embodiment of the present disclosure. As the compression element 38 moves from the position shown in solid lines to the position shown in phantom lines to reduce the vacuum from the high operating vacuum level for extraction (e.g., 200 mm Hg or the like) to the low vacuum level (e.g., 60 mm Hg or the like) to be maintained against the breast 2 during the pumping (expulsion) phase, a controlled valve may be provided in order to facilitate the flow, working together with the compression elements 36, 38. In the embodiment shown in FIG. 60, a valve mechanism 590 is provided to operate the one-way valve 50 to reduce the resistance to flow of the breast milk. In this embodiment, when the compression element 38 nears the end of its compression stroke (as shown in phantom in FIG. 60), it contacts pivot arm 592, forcing the contacted portion down and pivoting the opposite, non-contacted portion about pivot joint 592 to drive pushrod 594 upwardly. Pushrod 594 in turn pushes against lever arm 596 which rotates about pivot joint 599 forcing the free end of lever arm 596 against one-way valve to temporarily open it. The valve 50 closes when the compression element 38 retracts. The compression element 38 retracts in response to the pumping mechanism operating in its desired range of 60 mm Hg to 220 mm.

Figure 61:
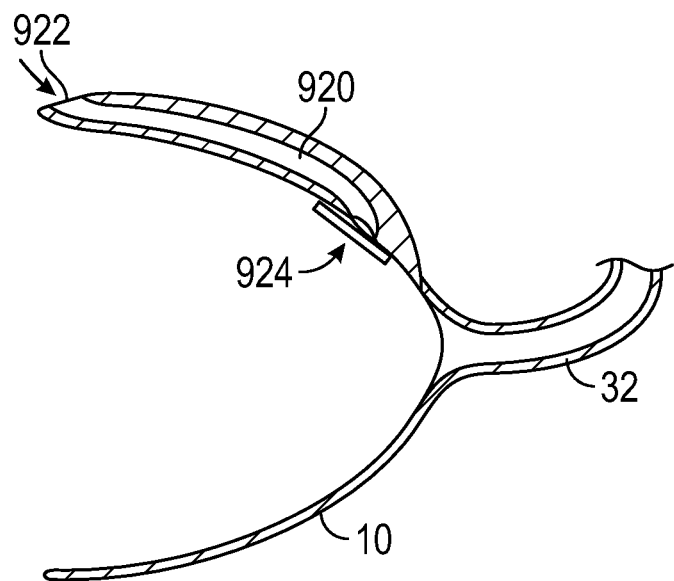
FIG. 61 is a longitudinal sectional view of a breast adapter and a portion of a tube illustrating a pressure relief valve according to an embodiment of the present disclosure.

FIG. 61 is a longitudinal sectional view of breast adapter 10 and a portion of tube 32 illustrating a pressure relief valve according to an embodiment of the present disclosure. In this embodiment one or more channels 920 may are provided in the wall of the breast adapter 10 to provide fluid communication between an external vent 922 and a valve 924, that together, form the pressure relief valve. Valve 924 as shown is in the form of a flap that can deflect. Flap 924 has a predetermined spring constant that keeps it in the closed configuration shown until a predetermined maximum suction value has been reached, such as −200 mm Hg, −220 mm Hg, or some other predetermined maximum suction level. Once the maximum suction level is exceeded, flap 924 opens to release vacuum from within the breast adapter 10 as outside air is ported through the vent 922 and channel(s) 922. Flap 924 closes automatically once the suction level drops back down to less than the predetermined maximum suction level.

Figure 62:
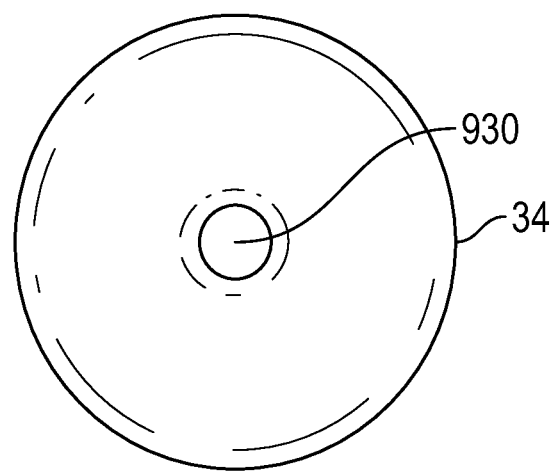
FIG. 62 illustrates a main body of the system having a see through window to ensure proper placement of the nipple, according to an embodiment of the present disclosure.

Optionally, the nipple receiving portion of the main body 34 may be configured for visualization therethrough so that a user, or a second person can confirm proper placement and alignment of the nipple 3' centrally within the breast adapter 10. The breast adapter portion receiving the nipple is also made visually clear, like that of the main body, to facilitate this visualization. Milk flow may also be visible through this clear window 930, see FIG. 62. Additionally, milk flow can be observed through the tube 32 and or container 60, which are also see through.

In some embodiments, breast adapter 10 has features to prevent the breast from becoming sweaty or too hot, for example, a large portion of the non-sealing portion of the breast adapter can be a breathable fabric, have vent holes, or be made of a cooling gel. The main body 34 in some embodiments has features that also prevent the breast from becoming sweaty or too hot, for example, vent holes in the main body release heat from the main body, a cooling fan provides a flow of air to cool the main body or the breast, or has a cavity in which a replaceable cooling pack is placed.

Figure 63:
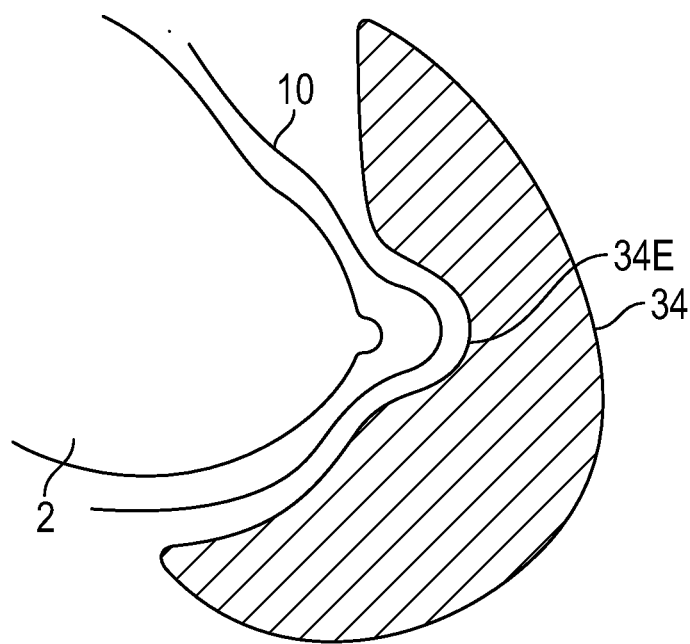
FIG. 63 illustrates a main body that can be at least partially peeled away which maintaining a seal of the breast adapter against the breast, according to an embodiment of the present disclosure.

FIG. 63 is a schematic representation of a portion of a system 100 that includes a main body 34 that can be peeled back or partially separated from the breast adapter 10 to allow the user or another person to see through the breast adapter 10, while maintaining the seal of the breast adapter 10 against the breast 2. The rear edge portion 34E of the main body may be made flexible to allow the peel back action.

Figure 64:
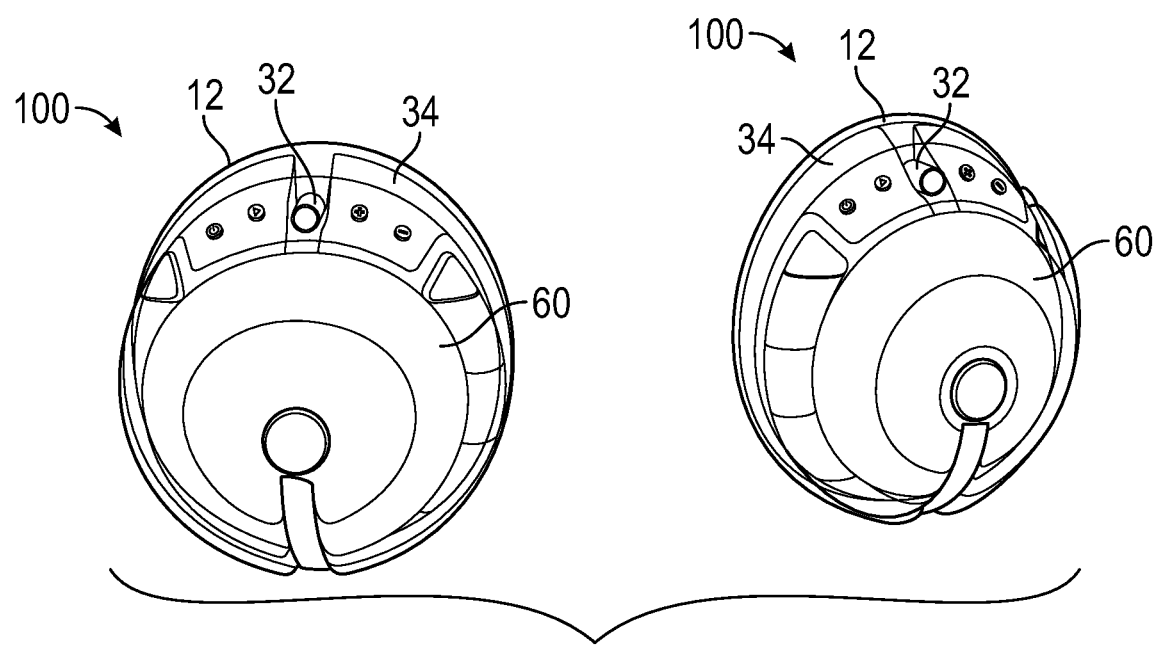
FIG. 64 illustrates a pair of breast pump systems that can be installed on both breasts of a user, according to an embodiment of the present disclosure.

The breast pump systems 100 of the present disclosure may be paired and used in parallel (or serially) when mounted to both breasts 2 of a user. As can be appreciated from the figures, the system can define a natural breast profile. The natural breast profile is contemplated to fit comfortably and conveniently into a bra of a user and to present a natural look. As such, the profile is characterized by having a non-circular base unlike that embodied in a generally dome-shaped configuration. Extending from the base are curved surfaces having asymmetric patterns. Moreover, like natural breasts, the profile of the device or system is contemplated to define one or more asymmetric curves and off-center inertial centers. Various natural breast shapes can be provided to choose from to the tastes and needs of a user. FIG. 64 is a perspective view showing a pair of breast pump systems 100, according to an embodiment of the present disclosure.

Figure 65:
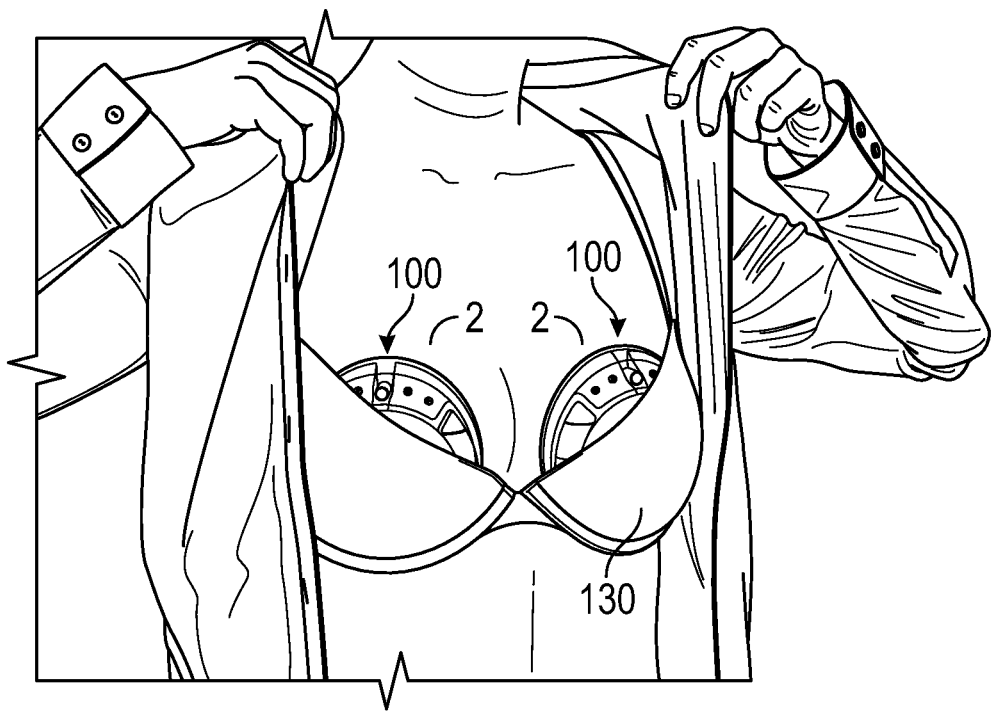
FIG. 65 illustrates a pair of breast pump systems installed on the breasts of a user and supported by a bra, according to an embodiment of the present disclosure.
Figure 66:
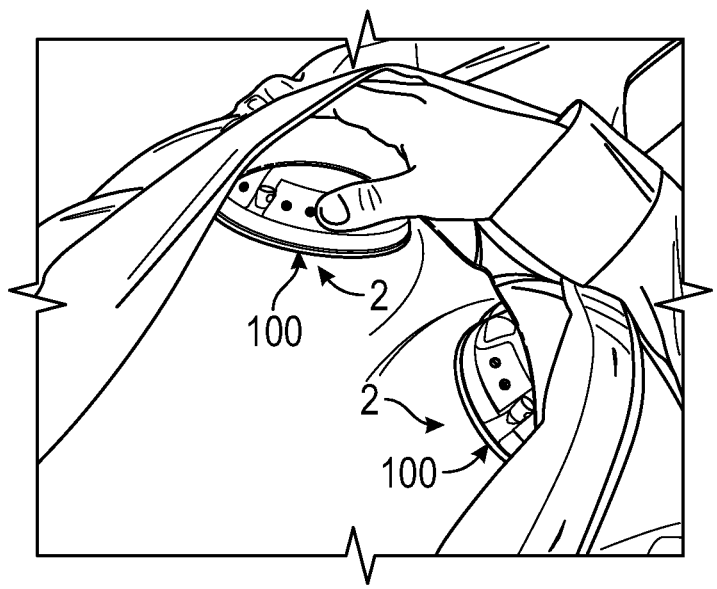
FIG. 66 illustrates the user of FIG. 65 using the breast pump systems while in a supine position, according to an embodiment of the present disclosure.
Figure 67:
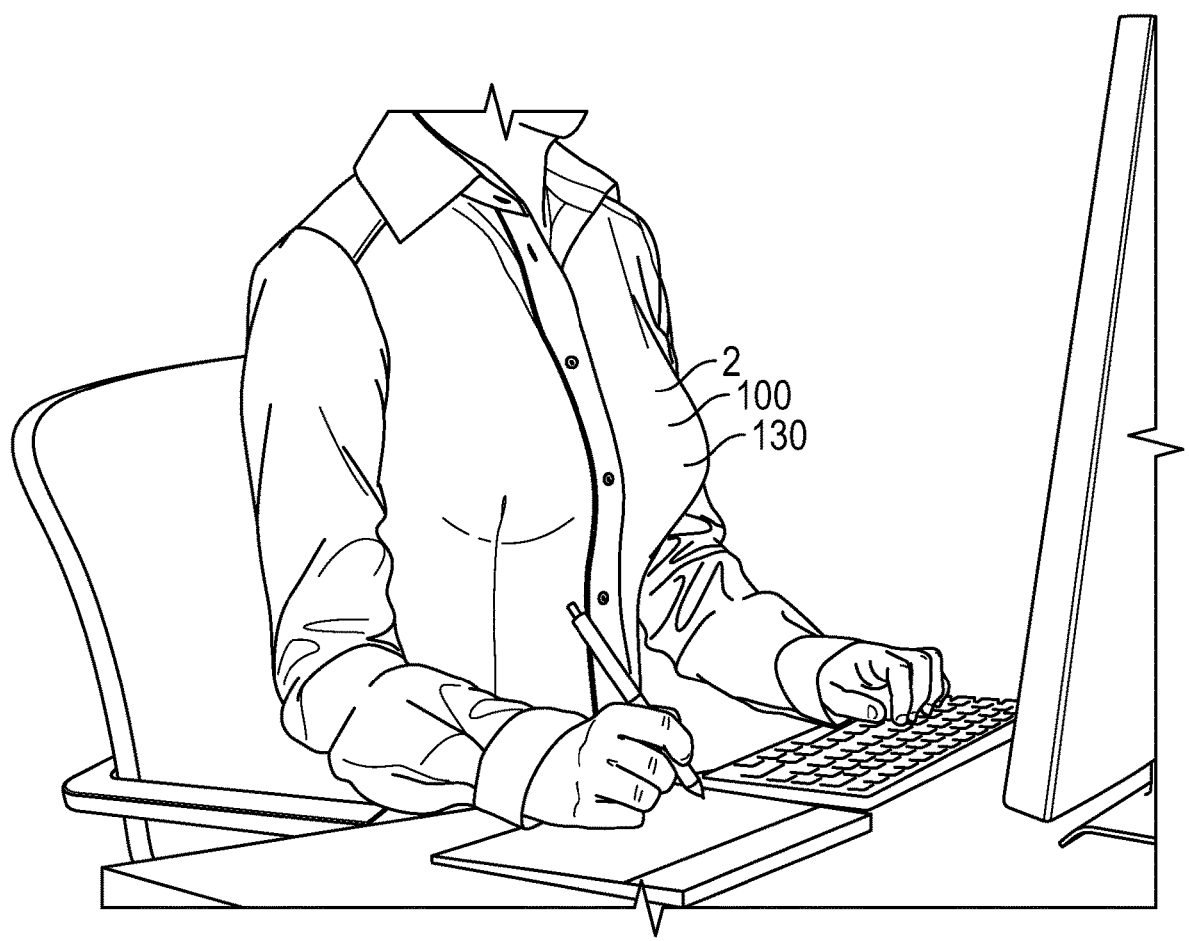
FIG. 67 illustrates the user of FIG. 65, with a blouse worn over the breast pump systems, using the breast pump systems while working at a work station, according to an embodiment of the present disclosure.
Figure 68:
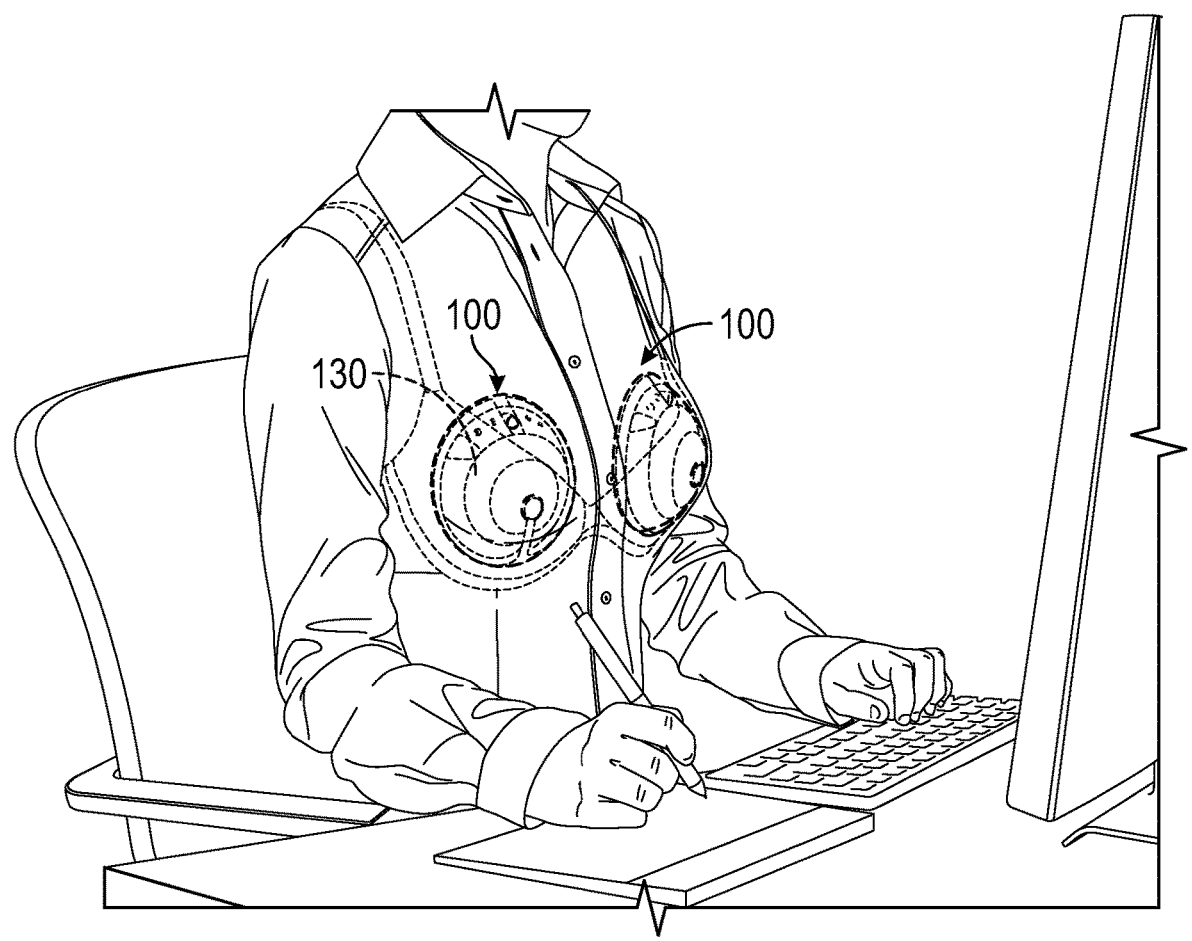
FIG. 68 shows the user of FIG. 67, with the blouse shown partially in phantom to better shown the underlying breast pump systems and bra, according to an embodiment of the present disclosure.

FIG. 65 shows a user wearing two breast pump systems 100 on breasts 2, the systems being supported by a bra 130. FIG. 66 shows the ability of the systems 100 to be used by the user while reclined or lying in a supine position. FIG. 67 shows the user wearing a blouse over the breast pump systems 100 and bra 130, demonstrating the degree to which the present system can be concealed, as the systems are barely noticeable, giving an elegant, natural look. FIG. 68 is the view of FIG. 67 with a portion of the blouse shown in phantom to show the systems 100 and bra 130.

While the present disclosure has been described with reference to the specific embodiments thereof, it should be understood by those skilled in the art that various changes may be made and equivalents may be substituted without departing from the true spirit and scope of the disclosure. In addition, many modifications may be made to adapt a particular situation, material, composition of matter, process, process step or steps, to the objective, spirit and scope of the present disclosure. All such modifications are intended to be within the scope of the present disclosure as described herein.

That which is claimed is:

1. A wearable, portable self-powered breast pump system shaped to fit within a bra, the breast pump system comprising:
   a housing, the housing including a receptacle formed therein;
   a breast adapter configured to contact and form a seal with a breast, the breast adapter including a nipple receiving portion formed integrally therewith, and a bottom portion below the nipple receiving portion, the breast adapter sized and shaped to be received within the receptacle;
   a pump contained within the housing, the pump positioned above the nipple receiving portion;
   a milk collection container defined by walls that are separate and distinct from the breast adapter and configured to contact the breast, the milk collection container being transparent and including graduation markers;
   an indicator light;
   a controller contained within the housing that changes application of a suction force on the breast through the nipple receiving portion by the pump from a letdown phase to an expression mode; and
   a battery electrically connected to the controller;
   wherein the pump is associated with the nipple receiving portion and the pump creates the suction force in the nipple receiving portion, the suction force and at least a portion of a pumped milk being directed generally upward relative to the bottom portion of the breast adapter;
   wherein the receptacle is positioned below a center of the housing so that the breast pump system rides in a higher position relative to the breast.

2. The wearable, portable self-powered breast pump system of claim 1, wherein the breast adapter is visually clear.

3. The wearable, portable self-powered breast pump system of claim 1, wherein the letdown phase lasts for a pre-determined time period.

4. The wearable, portable self-powered breast pump system of claim 1, wherein the expression mode continues for a pre-determined time period.

5. The wearable, portable self-powered breast pump system of claim 1, wherein the breast adapter is a breast shield.

6. The wearable, portable self-powered breast pump system of claim 1, wherein the breast pump system defines a generally breast shaped profile.

7. The wearable, portable self-powered breast pump system of claim 6, wherein the milk collection container forms part of the generally breast shaped profile.

8. The wearable, portable self-powered breast pump system of claim 1, further comprising a cap for the milk collection container after the milk collection container has been removed from the breast pump system.

9. The wearable, portable self-powered breast pump system of claim 1, wherein the breast adapter is a flange.

10. The wearable, portable self-powered breast pump system of claim 1, wherein the pump is configured to be positioned less than 2.5 cm from a nipple in the nipple receiving portion.

11. The wearable, portable self-powered breast pump system of claim 1, wherein the milk collection container is detachable from the breast pump system.

12. The wearable, portable self-powered breast pump system of claim 11, wherein the milk collection container is attachable to the breast pump system by turning the milk collection container.

13. The wearable, portable self-powered breast pump system of claim 1, further comprising a conduit attached to the nipple receiving portion of the breast adapter, the conduit configured to provide the suction force within the nipple receiving portion.

14. The wearable, portable self-powered breast pump system of claim 13, wherein the housing includes a channel configured and dimensioned to receive the conduit with a snap or friction fit and hold the conduit in a proper position.

15. The wearable, portable self-powered breast pump system of claim 1, further comprising a motor, wherein the nipple receiving portion integrally formed with the breast adapter extends within the housing beyond the motor thereby reducing an overall profile of the breast pump system.

* * * * *